(12) United States Patent
Phipps et al.

(10) Patent No.: US 10,919,073 B2
(45) Date of Patent: Feb. 16, 2021

(54) METERING DISPENSER FOR FLOWABLE COMPOSITIONS

(71) Applicant: DoseLogix, LLC, Woodstock, GA (US)

(72) Inventors: Timothy Gayle Phipps, Woodstock, GA (US); Daniel Lee DeYoung, Woodstock, GA (US); Dale Melton Coker, Woodstock, GA (US); Craig Jay Cochran, Atlanta, GA (US); John Britton S. Mockridge, Roswell, GA (US); Nicholas H. Reaves, Marietta, GA (US); Ellen Y. Brown, Marietta, GA (US)

(73) Assignee: DOSELOGIX, LLC, Woodstock, GA (US)

(*) Notice: Subject to any disclaimer, the term of this patent is extended or adjusted under 35 U.S.C. 154(b) by 50 days.

(21) Appl. No.: 16/399,978

(22) Filed: Apr. 30, 2019

(65) Prior Publication Data

US 2019/0255560 A1    Aug. 22, 2019

Related U.S. Application Data

(63) Continuation of application No. 15/328,401, filed as application No. PCT/US2015/055814 on Oct. 15, 2015, now Pat. No. 10,322,433.
(Continued)

(51) Int. Cl.
*A45D 34/04* (2006.01)
*B05C 17/01* (2006.01)
(Continued)

(52) U.S. Cl.
CPC .......... *B05C 17/0133* (2013.01); *A45D 34/04* (2013.01); *A45D 40/26* (2013.01);
(Continued)

(58) Field of Classification Search
CPC ............ B65D 83/0005; B65D 83/0011; B65D 41/02; B65D 2215/00; B65D 50/00;
(Continued)

(56) References Cited

U.S. PATENT DOCUMENTS

| D19,586 S | 1/1890 | Smith |
| D21,197 S | 12/1891 | Hess et al. |

(Continued)

FOREIGN PATENT DOCUMENTS

| EP | 0858271 | 3/2000 |
| WO | 9716088 | 5/1997 |
| WO | 2012131320 | 10/2012 |

OTHER PUBLICATIONS

Estee Lauder Golden Seashell Compact, Terapeak, Available online at: http://www.terapeak.com/worth/estee-lauder-golden-seashell-compact/191672034924/, Dec. 23, 2015, 3 pages.
(Continued)

*Primary Examiner* — Patrick M. Buechner
(74) *Attorney, Agent, or Firm* — Kilpatrick Townsend & Stockton LLP

(57) ABSTRACT

Described are metering dispensers having a body configured to hold a flowable composition in a chamber, a drive screw coupled to the body, and a plunger threadingly coupled to the drive screw. The plunger includes at least two annular lips that form a fluid seal with the chamber as the plunger travels along the drive screw through the chamber. A base is rotationally coupled to the body with a cam that contacts at least one tab extending externally from the body so that the tab enters at least one low point on the cam by traveling over a trailing edge of the low point, and the trailing edge then prevents the tab from exiting the low point in the direction of the trailing edge.

19 Claims, 49 Drawing Sheets

Related U.S. Application Data

(60) Provisional application No. 62/064,259, filed on Oct. 15, 2014.

(51) Int. Cl.
*A61M 35/00* (2006.01)
*B65D 83/00* (2006.01)
*A45D 40/26* (2006.01)
*B05C 17/005* (2006.01)
*B65D 41/02* (2006.01)
*B65D 47/00* (2006.01)
*B65D 50/00* (2006.01)

(52) U.S. Cl.
CPC ..... *A61M 35/003* (2013.01); *B05C 17/00513* (2013.01); *B05C 17/00516* (2013.01); *B05C 17/00576* (2013.01); *B65D 41/02* (2013.01); *B65D 47/00* (2013.01); *B65D 50/00* (2013.01); *B65D 83/0011* (2013.01); *A45D 2200/055* (2013.01)

(58) Field of Classification Search
CPC ................ B65D 47/00; B05C 17/0133; B05C 17/00576; B05C 17/00513; B05C 17/00516; A61M 35/003; A45D 40/04; A45D 40/12; A45D 2200/055; A45D 40/26; A45D 34/04; G01F 11/025; G01F 11/027
See application file for complete search history.

(56) References Cited

U.S. PATENT DOCUMENTS

| | | | |
|---|---|---|---|
| 835,446 A | 11/1906 | Lesueur | |
| 1,342,450 A * | 6/1920 | Kost | B05C 17/0133 |
| | | | 222/340 |
| 1,701,663 A * | 2/1929 | Clark | B65D 83/0011 |
| | | | 222/80 |
| D79,445 S | 9/1929 | Solon | |
| D93,591 S | 10/1934 | Wewetzer | |
| D115,881 S | 7/1939 | Lewis | |
| D166,238 S | 3/1952 | Bedinger | |
| D175,832 S | 10/1955 | Gerson | |
| D178,225 S | 7/1956 | Du Pree | |
| 2,812,763 A | 11/1957 | Ferguson | |
| 2,869,546 A | 1/1959 | Cantor | |
| 3,026,872 A | 3/1962 | Prater, Jr. | |
| 3,156,387 A * | 11/1964 | Harwood | B65D 83/0011 |
| | | | 222/390 |
| 3,227,161 A | 1/1966 | Lorenzo | |
| 3,306,252 A | 2/1967 | Knight et al. | |
| D212,992 S | 12/1968 | Scaler, Jr. | |
| 3,424,158 A | 1/1969 | Silver | |
| 3,581,399 A | 6/1971 | Dragan | |
| 3,656,480 A | 4/1972 | Rubricius | |
| 3,910,442 A | 10/1975 | Gargano | |
| D243,430 S | 2/1977 | Thrush | |
| D248,217 S | 6/1978 | Allen et al. | |
| 4,139,127 A * | 2/1979 | Gentile | B65D 83/0011 |
| | | | 222/390 |
| D253,514 S | 11/1979 | Etelson | |
| D255,096 S | 5/1980 | Etelson | |
| 4,298,036 A | 11/1981 | Horvath | |
| D267,546 S | 1/1983 | Manlove | |
| D270,386 S | 8/1983 | Lee | |
| 4,421,504 A | 12/1983 | Kline | |
| D281,042 S | 10/1985 | Antoni et al. | |
| 4,545,696 A * | 10/1985 | Carluccio | A45D 40/04 |
| | | | 401/175 |
| D281,350 S | 11/1985 | Heier | |
| 4,645,098 A | 2/1987 | Hoffmann | |
| D300,510 S | 4/1989 | Mason, Jr. | |
| D303,724 S | 9/1989 | Horng et al. | |
| D308,021 S | 5/1990 | Natori | |
| D314,842 S | 2/1991 | Fleming | |
| 5,347,265 A | 9/1994 | Shimura | |
| 5,374,263 A | 12/1994 | Weiler | |
| 5,425,580 A | 6/1995 | Beller | |
| 5,460,782 A | 10/1995 | Coleman et al. | |
| D371,743 S | 7/1996 | Wacker | |
| D373,931 S | 9/1996 | Whitehead | |
| 5,725,133 A * | 3/1998 | Iaia | A45D 40/04 |
| | | | 222/390 |
| 5,800,169 A | 9/1998 | Muhlbauer | |
| 6,027,471 A | 2/2000 | Fallon et al. | |
| 6,234,698 B1 * | 5/2001 | De Laforcade | A45D 40/04 |
| | | | 401/175 |
| 6,398,763 B1 | 6/2002 | Richardson et al. | |
| 6,474,369 B2 | 11/2002 | Castellano | |
| D501,188 S | 1/2005 | Zhu | |
| 6,981,618 B2 | 1/2006 | Reisinger | |
| D543,456 S | 5/2007 | Muhlemann | |
| 7,213,994 B2 | 5/2007 | Phipps et al. | |
| D557,605 S | 12/2007 | Reber, II et al. | |
| 7,442,179 B1 | 10/2008 | Just | |
| 7,503,905 B2 | 3/2009 | Jessop et al. | |
| D610,678 S | 2/2010 | Kawamura | |
| 8,308,678 B2 | 11/2012 | Swick | |
| D679,195 S | 4/2013 | Markham | |
| D681,459 S | 5/2013 | Ramsey et al. | |
| D688,830 S | 8/2013 | Friedman | |
| 8,544,684 B2 | 10/2013 | Perez | |
| D693,220 S | 11/2013 | Luo | |
| D710,699 S | 8/2014 | Phelps | |
| 8,801,675 B2 | 8/2014 | Janish et al. | |
| 9,022,258 B2 | 5/2015 | Nehren et al. | |
| D760,077 S | 6/2016 | Rye et al. | |
| D763,096 S | 8/2016 | Jerez Quintana | |
| D772,066 S | 11/2016 | Phipps et al. | |
| D823,116 S | 7/2018 | Phipps et al. | |
| 10,086,146 B2 | 10/2018 | Phipps et al. | |
| 10,308,418 B1 * | 6/2019 | Dakolios | A45D 40/04 |
| 10,322,433 B2 | 6/2019 | Phipps et al. | |
| 10,702,654 B2 | 7/2020 | Phipps et al. | |
| 2002/0049405 A1 | 4/2002 | Deslauriers et al. | |
| 2004/0127846 A1 | 7/2004 | Dunn et al. | |
| 2005/0054991 A1 | 3/2005 | Tobyn et al. | |
| 2007/0000946 A1 | 1/2007 | Phipps et al. | |
| 2009/0317168 A1 | 12/2009 | Theroude | |
| 2009/0326479 A1 | 12/2009 | Janish et al. | |
| 2009/0326506 A1 | 12/2009 | Hasegawa et al. | |
| 2010/0001026 A1 | 1/2010 | Springhorn et al. | |
| 2012/0035556 A1 | 2/2012 | Nordsiek et al. | |
| 2012/0205393 A1 | 8/2012 | Perez | |
| 2013/0165853 A1 | 6/2013 | Kawamura | |
| 2014/0031323 A1 | 1/2014 | Perez | |
| 2017/0348196 A1 | 12/2017 | Yuki et al. | |
| 2018/0086541 A1 * | 3/2018 | Ellsworth | A45D 34/04 |
| 2020/0148462 A1 * | 5/2020 | Brugger | B65D 83/0011 |

OTHER PUBLICATIONS

Real Seashell Ring Box Take 2, Paul Pape Designs, YouTube, Available online at: https://www.youtube.com/watch?v=389UvZ36X6c, Jun. 9, 2013, 1 page.
U.S. Appl. No. 15/172,876, Final Office Action dated Dec. 4, 2017, 10 pages.
U.S. Appl. No. 15/172,876, Non-Final Office Action dated Mar. 27, 2018, 9 pages.
U.S. Appl. No. 15/172,876, Non-Final Office Action dated Sep. 5, 2017, 9 pages.
U.S. Appl. No. 29/529,088, Notice of Allowance dated Jul. 12, 2016, 11 pages.
U.S. Appl. No. 29/582,813, Notice of Allowance dated Mar. 13, 2018, 9 pages.
International Application No. PCT/US2015/055814, International Search Report and Written Opinion dated Mar. 15, 2016, 28 pages.
International Application No. PCT/US2015/055814, Invitation to Pay Additional Fees and, Where Applicable, Protest Fee dated Jan. 14, 2016, 8 pages.

(56) References Cited

OTHER PUBLICATIONS

U.S. Appl. No. 16/031,746, Non-Final Office Action dated Oct. 25, 2019, 7 pages.

* cited by examiner

METERING DISPENSER FOR FLOWABLE COMPOSITIONS

CROSS-REFERENCE TO RELATED APPLICATIONS

This application is a continuation of U.S. application Ser. No. 15/328,401, filed on Jan. 23, 2017 and titled METERING DISPENSER FOR FLOWABLE COMPOSITIONS, which is the U.S. National Stage of International Application No. PCT/US2015/055814, filed on Oct. 15, 2015 and titled METERING DISPENSER FOR FLOWABLE COMPOSITIONS, which claims the benefit of U.S. Provisional Application No. 62/064,259, filed Oct. 15, 2014 and titled METERING DISPENSER FOR FLOWABLE COMPOSITIONS, all of which are herein incorporated herein by reference in their entireties.

FIELD OF THE INVENTION

The field of the invention relates to dispensers for flowable compositions, and more particularly, to a dispenser having a rotatable housing which causes a floor member to rise and urge a predetermined amount of flowable composition through an opening in a cap.

BACKGROUND

Traditionally, topically administered medicine was often formulated as liquids. Applying a liquid to a skin surface often resulted in a portion of the dose spreading beyond the target area. Cream-based formulations were developed as viscous liquids to prevent the unintended application of the medicine to an unaffected area. More recently, pharmacists have been taking traditional medicines and "compounding" them in a cream base.

Administering the cream-based medicines is a challenge because providing an accurate measured dose is not easy. One common form of a dispenser is a traditional hypodermic syringe, without the needle. The user can depress the plunger to force an amount of cream out of the barrel as indicated by markings on the side of the barrel. For older patients, it is not always easy to measure out 0.1 ml or so of medicine, as this may require more dexterity than is available.

Recent improvements have been made to develop a more accurate method of metering creams, such as is described in U.S. Pat. No. 7,213,994. Specifically, the improvements comprise a metering system that uses a plunger to express an accurate dosage from a chamber by relying on a specified number of turns of a drive screw to advance the plunger and deliver a known amount of medicine. The metering system provides an audible sound when a unit or "click" has been delivered.

To ensure that the dispenser provides an accurate dosage, the patient should be consistently alerted to stop rotation of the drive screw at the appropriate location, and the amount of medicine that is pushed through a dispensing end should not vary due to leaks or fluctuation in the movement of the plunger.

In certain cases, particularly when there is not a perfectly tight fit between the plunger and the walls of the chamber, the plunger may turn slightly within the chamber when the drive screw turns, which may allow small gaps to form between the plunger and the chamber. As a result, the cream may squeeze down through the small gaps rather than exiting through the dispensing end of the chamber, which could result in metering inaccuracies. Because of the potential for possible leaks with cream-based medicines, this design may not be practical for use with certain liquids or fluids that would have a higher tendency to leak or spill.

In some embodiments, the coupling between the drive screw and the chamber may have some elasticity when the drive screw is retained within the chamber through the use of internally directed tapering fingers, which allows the chamber to be pushed up slightly relative to the drive screw when the base is rotated. This slight shift may cause less than the full dosage to be dispensed, which could also lead to metering inaccuracies.

Also, in many cases, the patient is relying on an audible sound to confirm that the dosage is complete. In certain instances, the click mechanism may lose elasticity if left in a "mid-click" position. In those cases, it may take some time for the click mechanism to regain its elasticity and until it does, there may not be an audible click response, which could also potentially lead to metering inaccuracies.

As a result, it may be desirable to provide a metered dispenser that forms a fluid seal for a variety of compositions, including viscous liquids or other fluids with a positive viscosity, which also includes a click mechanism that is not affected when the dispenser is left in a "mid-click" position.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the present invention, a metering dispenser comprises a body comprising an inner wall, a first end, and a second end, wherein the inner wall defines a chamber having a cross-sectional shape that varies along a longitudinal draft and configured to hold a flowable composition, a drive screw coupled to the second end of the body, wherein the drive screw comprises an elongated shaft having at least one external thread, wherein the elongated shaft is arranged to extend substantially along a length of the chamber, and a plunger comprising a plunger cross-sectional shape, wherein the plunger is positioned within the chamber and is coupled to the elongated shaft of the drive screw so that the plunger travels along the elongated shaft through the chamber when the drive screw is rotated, wherein the plunger comprises at least two annular lips for contact with the inner wall, wherein at least one annular lip of the at least two annular lips is configured to flex in a direction toward the first end of the body so that the plunger forms a fluid seal with the inner wall of the chamber as the plunger travels along the elongated shaft through the chamber.

In certain embodiments, the plunger cross-sectional shape is not round and/or the plunger cross-sectional shape is oval.

The second annular lip of the at least two annular lips may be configured to flex in a direction toward the second end of the body. In some embodiments, an O-ring is mounted on the plunger for contact with the inner wall.

In certain embodiments, the at least two annular lips are configured to maintain the fluid seal over variations of 0.01% to 25% in cross-sectional area along the longitudinal draft of the chamber.

The at least two annular lips may be configured to maintain the fluid seal for any composition having a positive viscosity. In some embodiments, a third annular lip of the at least two annular lips is positioned between a first annular lip and a second annular lip the at least two annular lips, wherein the third annular lip is configured to be arranged substantially perpendicular to the inner wall of the chamber as the plunger travels along the elongated shaft through the chamber.

In some embodiments, at least one anchor is positioned to prevent radial movement of the plunger relative to the inner wall of the chamber.

In certain embodiments, the metering dispense further comprises a base and at least one projection on one of the base or the body for engagement with a contact surface on the other of the body and base to cause the rotational forces necessary to rotate the base relative to the body to vary depending on the relative rotational position of the base relative to the body. The engagement between the projection and contact surface may result in home positions at predetermined angular positions. The engagement between the projection and contact surface may further resist rotation in a first direction and facilitates rotation in an opposite direction.

In some embodiments, the metering dispenser further comprises a base rotationally coupled to the second end of the body, wherein the force required to rotate the base and body relative to each other varies to provide tactile feedback to a user.

In some embodiments, the metering dispenser further comprises a base rotationally coupled to the second end of the body, wherein rotation of the base and body relative to each other provides audible feedback when at least one relative position is reached.

According to certain embodiments, a base is rotationally coupled to the second end of the body, wherein one of the base and the second end of the body comprises a cam comprising at least one low point having a trailing edge. The cam may be asymmetrical around a longitudinal axis of the metering dispenser. In some embodiments, the base comprises the cam.

In these embodiments, the cam is configured to contact at least one tab extending from the other of the cam and the second end of the body so that the at least one tab enters the at least one low point by traveling over the trailing edge, wherein the trailing edge is configured to prevent the at least one tab from exiting the at least one low point in the direction of the trailing edge. The at least one tab may extend from the second end of the body.

The cam may further comprise at least one cam lobe configured to induce radial bending of the at least one tab when the at least one tab travels over the at least one cam lobe. In these embodiments, the at least one tab may produce an audible sound when the at least one tab travels from the at least one cam lobe to the at least one low point on the cam.

In various embodiments, the metering dispenser may further comprise a child resistant receptacle. The child resistant receptacle may comprise a sidewall that substantially surrounds the metering dispenser and a pair of lips that extend below the metering dispenser. The child resistant receptacle may be positionable proximate the base to make rotation of the base at least difficult. The child resistant receptacle may be difficult for a typical child to remove. The child resistant receptacle may surround the base and require compression at a predetermined position to release the child resistant receptacle from the base. The child resistant receptacle may comprise a sidewall that substantially surrounds the base and at least a portion of a cap on the body, thereby resisting (1) rotation of the base relative to the body and (2) removal of the base.

According to certain embodiments of the present invention, a metering dispenser comprises a body comprising an inner wall, a first end, and a second end comprising a body plate, wherein the inner wall defines a chamber, and a drive screw comprising an elongated shaft extending from a first side of a screw plate and a cog positioned at a second end of the coupling body, wherein the drive screw is positioned within the chamber so that the elongated shaft is arranged to extend substantially through the chamber and the second side of the screw plate is positioned adjacent an inner side of the body plate, wherein the coupling body and the cog extend from the second side of the screw plate through an aperture in the body plate, wherein a plurality of tapering fingers are positioned around a lip of the aperture in the body plate and arranged so that at least one of the plurality of tapering fingers is arranged along the coupling body so that a tip of the at least one of the plurality of tapering fingers contacts a lip of the cog, and wherein the positioning of the screw plate adjacent the inner side of the body plate prevents further movement of the drive screw in a direction of the second end of the body.

In certain embodiments, the radial engagement structure comprises at least one tapering finger positioned to contact an annular lip on the drive screw. The at least one tapering finger may comprise a plurality of tapering fingers positioned to extend generally along the drive screw to contact the lip of the drive screw. The metering dispenser may further comprise a coupler for rotational engagement with the base, which comprises at least one spline for engagement with at least one groove in the base.

In some embodiments, the plurality of tapering fingers provide resistance to further movement of the drive screw in a direction of the first end of the body.

According to certain embodiments, a base is rotationally coupled to the second end of the body, wherein the base comprises a bushing circumferentially coupled to the cog of the drive screw. The bushing may be configured to longitudinally travel along a length of the cog. In some embodiments, a cam is arranged around a circumferential outer surface of the bushing, wherein the cam comprises at least one low point having a trailing edge. In certain embodiments, the cam is configured to contact at least one tab extending from an external side of the body plate.

In some embodiments, the cam further comprises at least one cam lobe configured to induce radial bending of the at least one tab when the at least one tab travels over the at least one cam lobe. In these embodiments, the contact between at least one tab and cam may produce an audible sound when the at least one tab travels from the at least one cam lobe to the at least one low point on the cam.

In various embodiments, the metering dispenser may further comprise a child resistant lock comprising a sidewall that substantially surrounds the metering dispenser and a pair of lips that extend below the metering dispenser.

According to certain embodiments of the present invention, a metering dispenser comprises a body comprising a first end and a second end comprising a body plate, the body plate comprising at least one tab and at least one projection, and a base rotationally coupled to the second end of the body, wherein the base comprises a cam and at least one protrusion, the cam comprising at least one low point having a trailing edge, wherein the at least one low point on the cam and the at least one protrusion are arranged so that the at least one protrusion contacts the at least one projection producing an audible sound when the protrusion passes over the at least one projection, and wherein the cam is configured to contact the at least one tab so that the at least one tab enters the at least one low point by traveling over the trailing edge, wherein the trailing edge is configured to prevent the at least one tab from exiting the at least one low point in the direction of the trailing edge.

In certain embodiments, the cam further comprises at least one cam lobe configured to induce radial bending of the at least one tab when the at least one tab travels over the at least one cam lobe. In these embodiments, the at least one tab may produce an additional audible sound when the at least one tab travels from the at least one cam lobe to the at least one low point on the cam.

In various embodiments, the metering dispenser may further comprise a child resistant lock comprising a sidewall that substantially surrounds the metering dispenser and a pair of lips that extend below the metering dispenser.

According to certain embodiments of the present invention, a metering dispenser comprises a body comprising an inner wall, a first end, and a second end, wherein the inner wall defines a chamber configured to hold a flowable composition, and wherein the first end of the body comprises an aperture that provides access to the chamber, an administering tool coupled to the first end of the body proximate the aperture, wherein the administering tool comprises at least one hole therethrough, and a plunger slidingly coupled to the inner wall of the chamber, wherein the plunger comprises a top surface arranged so as to mate with the reinforcing ribs when the plunger is positioned proximate the inner surface of the administering tool.

In some embodiments, the administering tool further comprises a threaded nozzle arranged proximate the at least one hole. The administering tool may also comprise a restrictor plate that is configured to reduce a size of the opening of the at least one hole. In some embodiments, a top surface of the administering tool further comprises a plurality of protrusions.

In various embodiments, the metering dispenser may further comprise a child resistant receptacle. The child resistant receptacle may comprise a sidewall that substantially surrounds portions of the metering dispenser and a pair of lips that extend below the metering dispenser. The child resistant receptacle may be configured, when positioned to substantially surround the body, to prevent removal of the metering dispenser from the child resistant receptacle. The child resistant receptacle may further comprise a pair of lips that extend below the base to resist removal of the child resistant receptacle. In certain embodiments, the child resistant receptacle comprises a lower portion having locking tabs that engage a cap to prevent removal of the cap.

In certain embodiments, the body comprises acetal resin, polypropylene, polycarbonate, polyethylene, acrylonitrile butadiene styrene, or a mixture thereof.

According to certain embodiments of the present invention, a metering dispenser comprises a body comprising an inner wall, a first end, and a second end comprising a body plate comprising engagement structure, wherein the inner wall defines a chamber, a plunger positionable in the chamber, a base, and a drive screw comprising an elongated threaded shaft threaded through the plunger, two ends, and on one of the two ends, a coupler for rotational engagement with the base, and radial engagement structure for engagement with the body plate to limit relative radial movement, wherein the drive screw is positionable within the chamber to drive the plunger through the chamber when the drive screw is rotated.

In certain embodiments, the drive screw comprises mechanically fused threads on an opposing one of the two ends.

DETAILED DESCRIPTION

Figure 1:
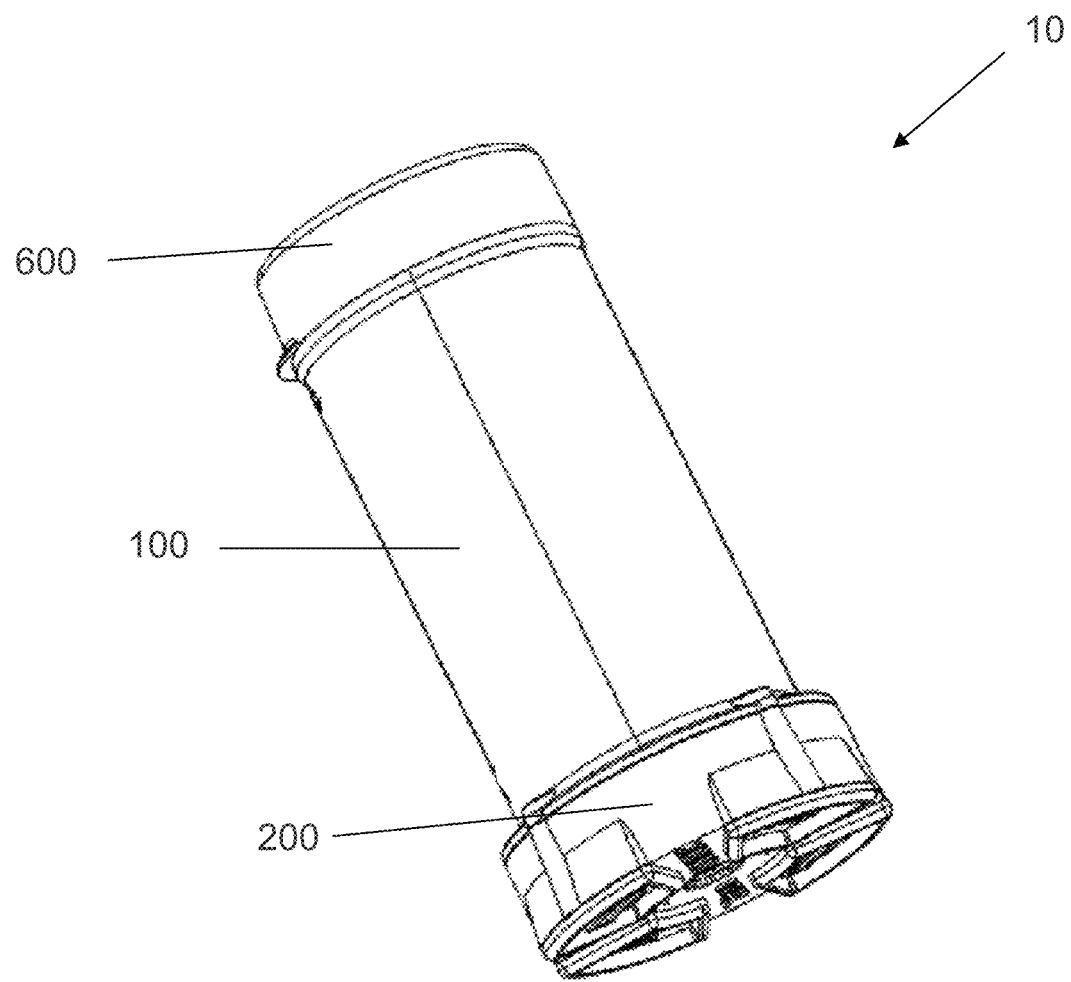
FIG. 1 is a perspective view of a metering dispenser, according to certain embodiments of the present invention.
Figure 2:
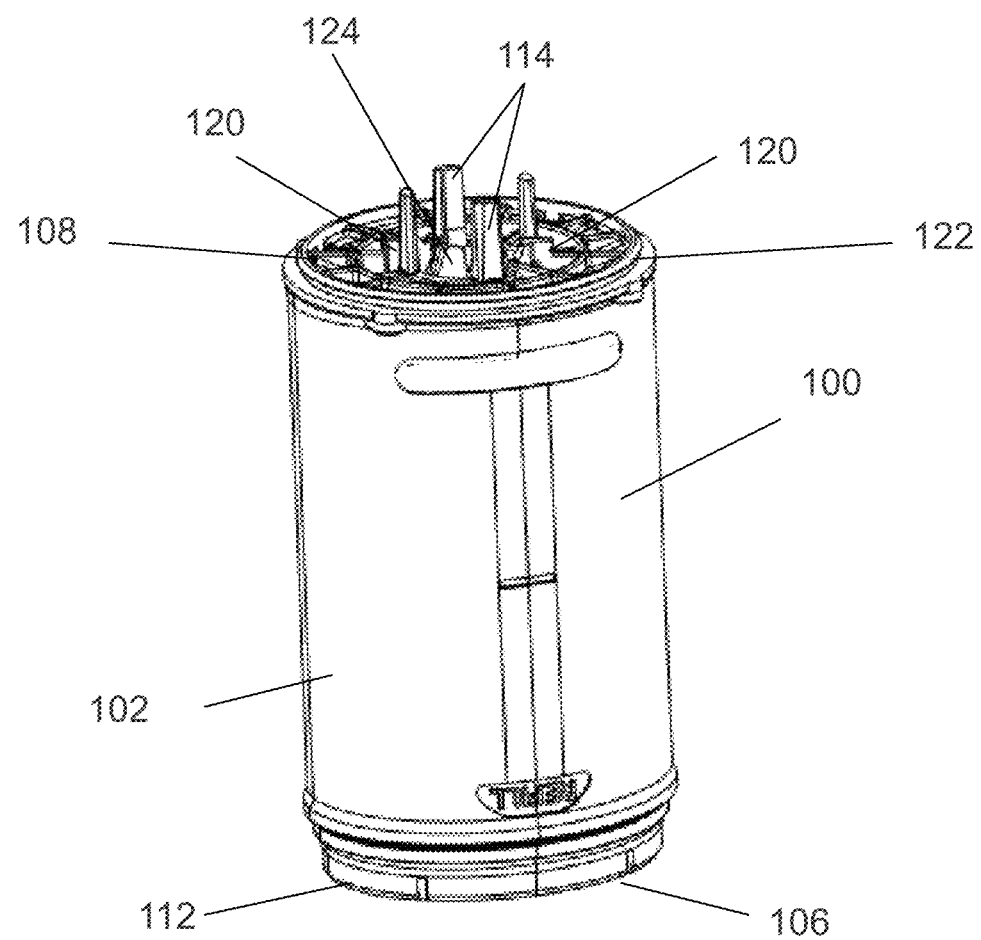
FIG. 2 is an inverted perspective view of a body of the metering dispenser of FIG. 1.
Figure 3:
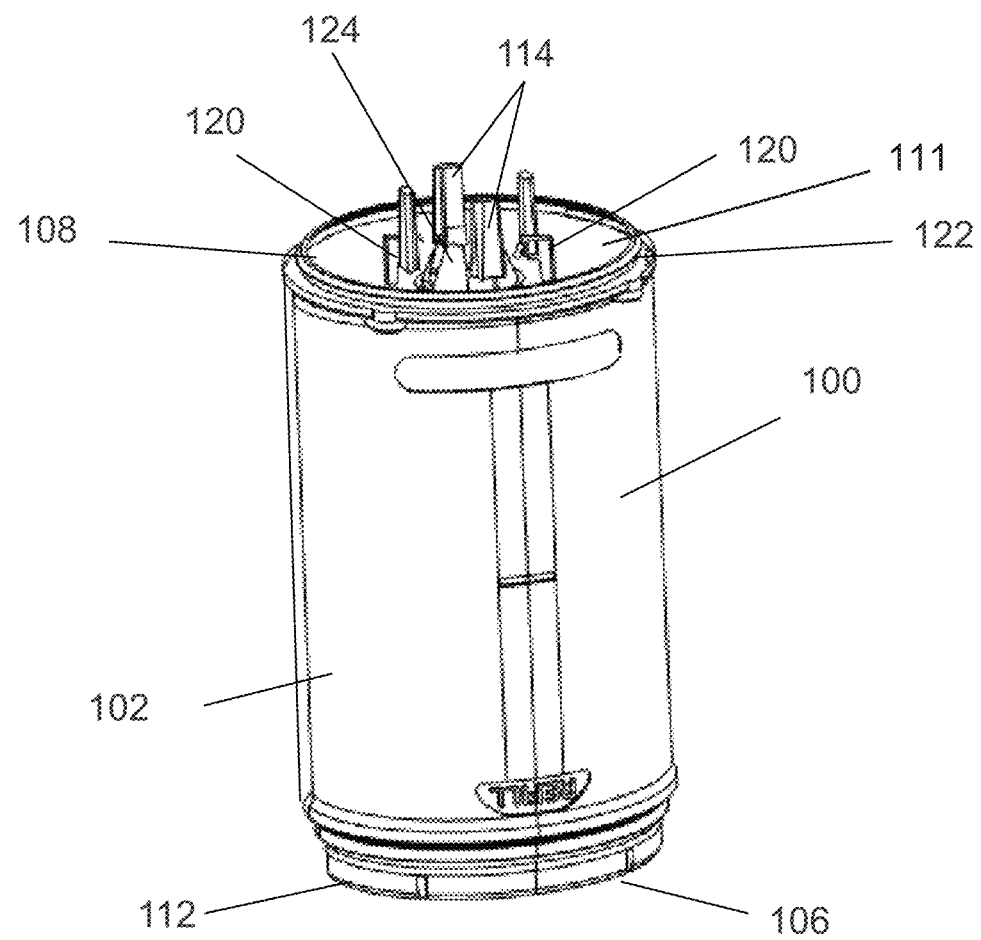
FIG. 3 is another perspective view of the body of FIG. 2 with certain details of a body plate removed for clarity.
Figure 4:
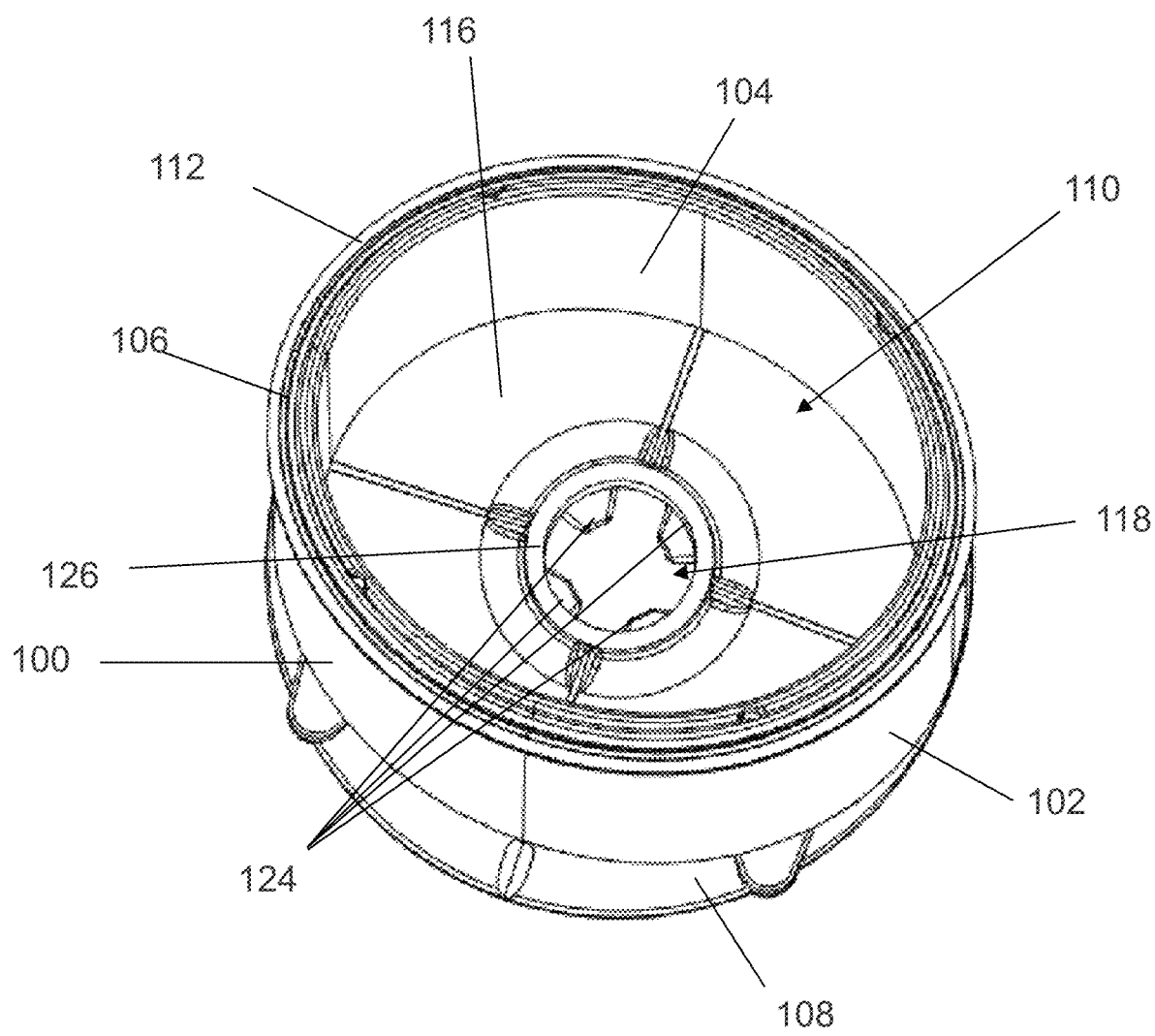
FIG. 4 is a perspective view of a chamber formed inside the body of FIG. 2.
Figure 5:
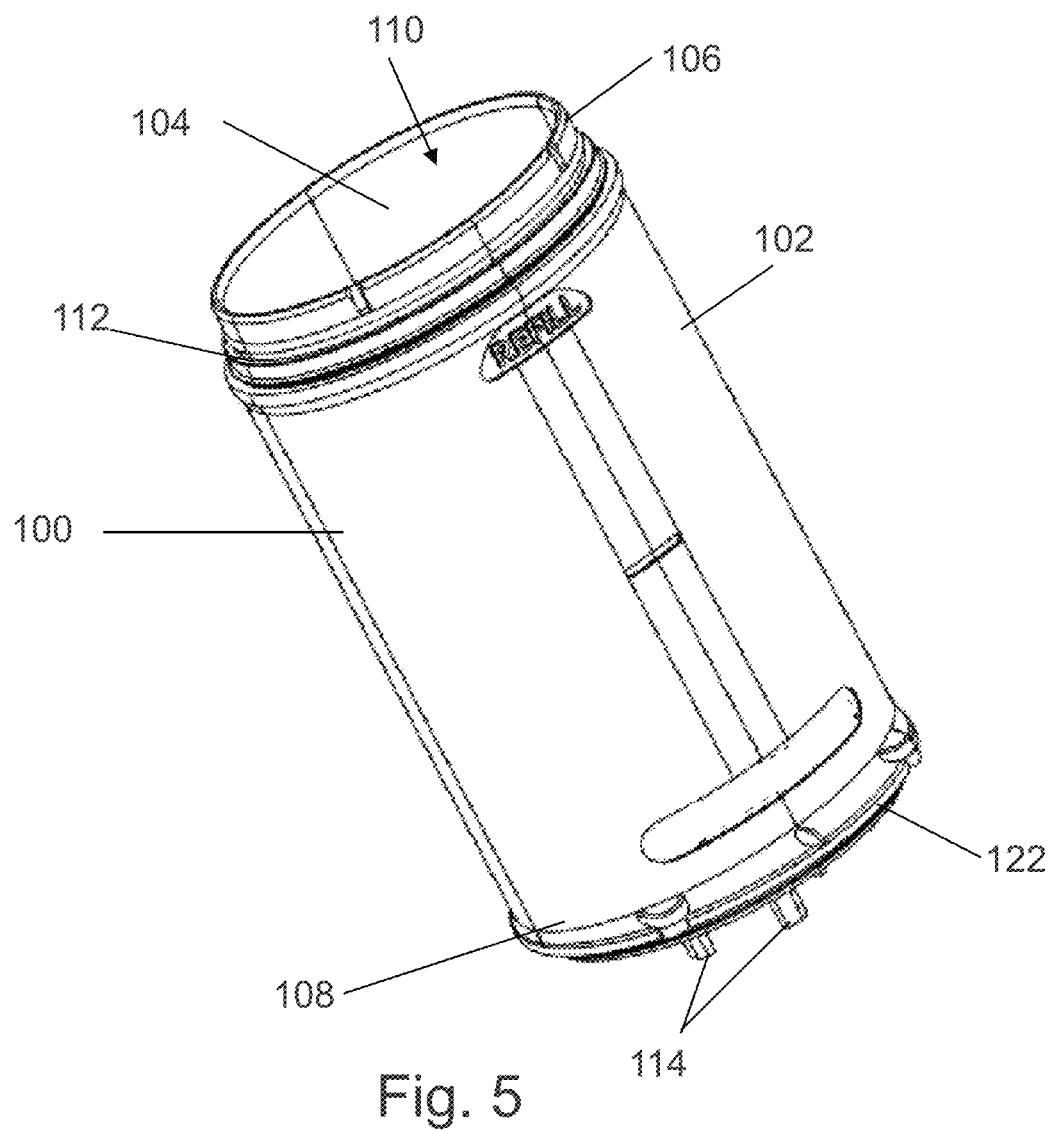
FIG. 5 is another perspective view of the body of FIG. 2.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

FIGS. 1-31 show certain embodiments of a metering dispenser 10 according to the present invention for dispensing a flowable composition 20. The flowable composition 20 may include but is not limited to creams or semi-solid emulsions such as oil-in-water creams and water-in-oil creams, gels, sols, colloids, suspensions, solutions, liquids with positive viscosity such as syrups, or other suitable flowable compositions or medicaments.

In certain embodiments, a dispenser 10 may have the following main components: a body 100, a base 200, a drive screw 300, a plunger 400 incorporating a fluid seal, an administering tool 500, and a cap 600. Some or all of the parts that comprise the dispenser 10 may be formed of materials including but not limited to polymer, plastic, composite, or other formable or moldable material.

In certain embodiments, as best illustrated in FIGS. 2-5 and 44-45, the body 100 comprises an outer wall 102, an inner wall 104, a first end 106, and a second end 108. The second end 108 may include an end wall 111. In certain embodiments, the body 100 may be formed of any suitable material including but not limited to acetal resin, polypropylene, polycarbonate, polyethylene, acrylonitrile butadiene styrene, other plastics, composites, or other suitable materials. The inner wall 104 defines a chamber 110 that may be configured to hold the flowable composition 20. In certain embodiments, the chamber 110 may have any suitable cross-sectional shape and the plunger 400 may have any suitable plunger cross-sectional shape that will allow the inner wall 104 of the chamber 110 and the plunger 400 to form a fluid seal and interlock with one another in a way that prevents the plunger 400 from freely rotating within the chamber 110, which is described in more detail below. For example, the chamber 110 and the plunger 400 may have any suitable interlocking shapes including but not limited to oval, elliptical, triangle, rectilinear, parabolic, hexagonal, other polygons, irregular circles, or any other interlocking shapes.

The first end 106 may include an external upper rim 112. The external upper rim 112 may be configured to couple to the administering tool 500, which is described in more detail below.

The second end 108 may include a plurality of tabs 114 projecting downward from a body plate 116. In certain embodiments, the tabs 114 are elongated strips that are configured to elastically bend and return to an unbent or relaxed position after an external force is removed. The plurality of tabs 114 may be concentrically arranged around an aperture 118 extending through a central location on the body plate 116.

The second end 108 may further comprise a plurality of projections 120 also projecting downward from the body plate 116. The projections 120 may also be concentrically arranged around the aperture 118 and may be positioned equidistant between two of the plurality of tabs 114 and/or may be positioned closer to one of the plurality of tabs 114. In certain embodiments, the projections 120 may also be spaced farther away from or closer to the aperture 118 than the tabs 114. There may be fewer, the same, or a greater number of tabs 114 than projections 120. In certain embodiments, the projections 120 may be shorter than the tabs 114, but may also be the same or similar height or taller than the tabs 114 as needed.

The second end 108 may further include an external lower rim 122. The external lower rim 122 may be configured to couple to the base 200, which is described in more detail below.

In certain embodiments, as best illustrated in FIGS. 6-8 and 46-47, the base 200 comprises a bottom portion 202, a sidewall 204, bushing 206, and a cam 208.

An upper edge 210 of the sidewall 204 may comprise a lip 212 that is configured to mate with the external lower rim 122 of the body 100. In certain embodiments, the lip 212 and the external lower rim 122 may be configured to couple via a snap-fit, screw, latch, or other suitable mechanical fastening design. In certain cases, the coupler for rotational engagement with the base 200 comprises at least one spline for engagement with at least one groove in the base 200.

The bushing 206 may extend upwardly from the bottom portion 202. An aperture 214 may extend through the bushing 206. A circumferential inner surface 216 of the bushing 206 may comprise a plurality of teeth that are configured to interlock with similarly shaped teeth on a cog 314 of the drive screw 300, which is discussed in more detail below.

Figure 7:
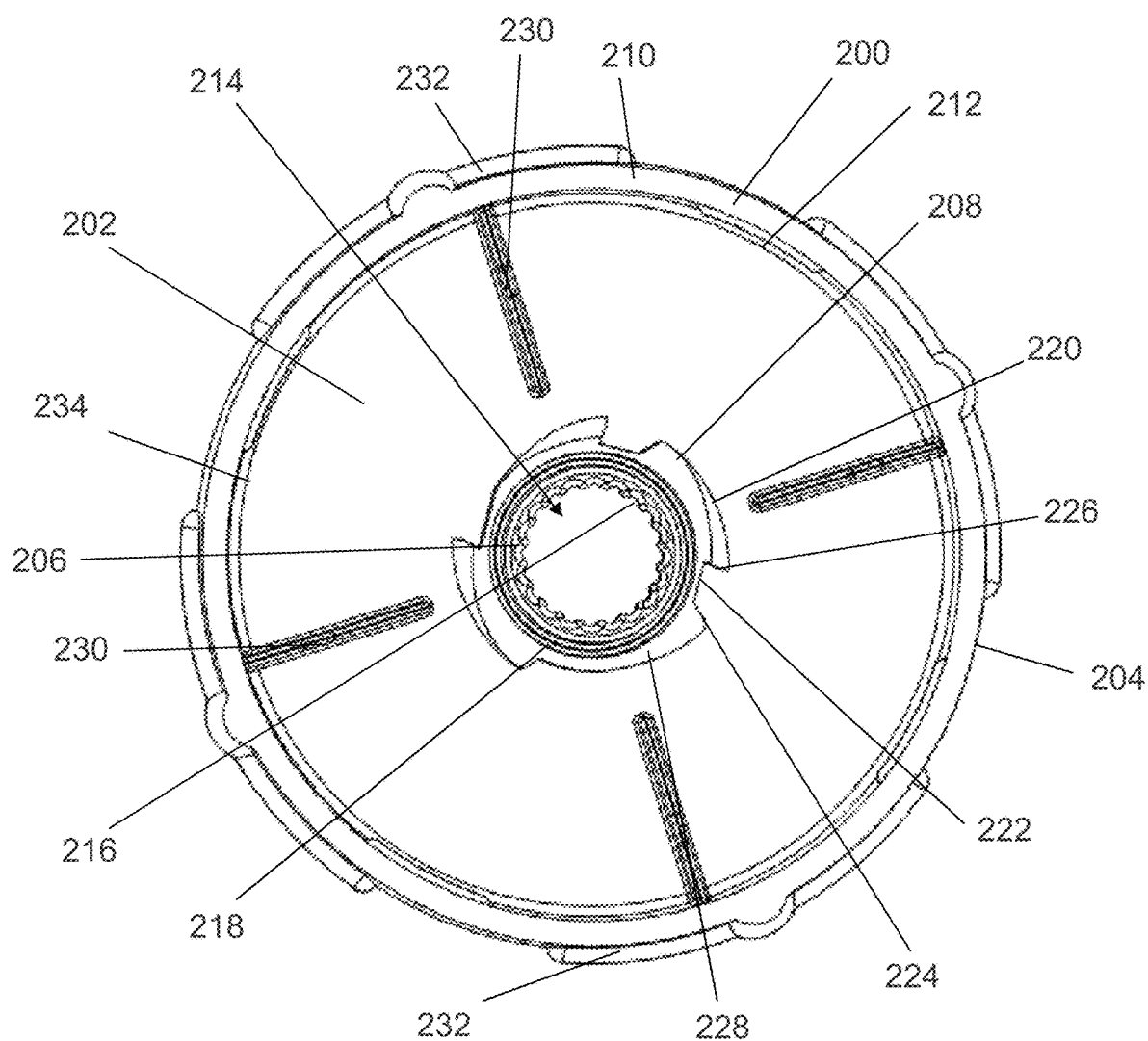
FIG. 7 is a top view of the base of FIG. 6.
Figure 47:
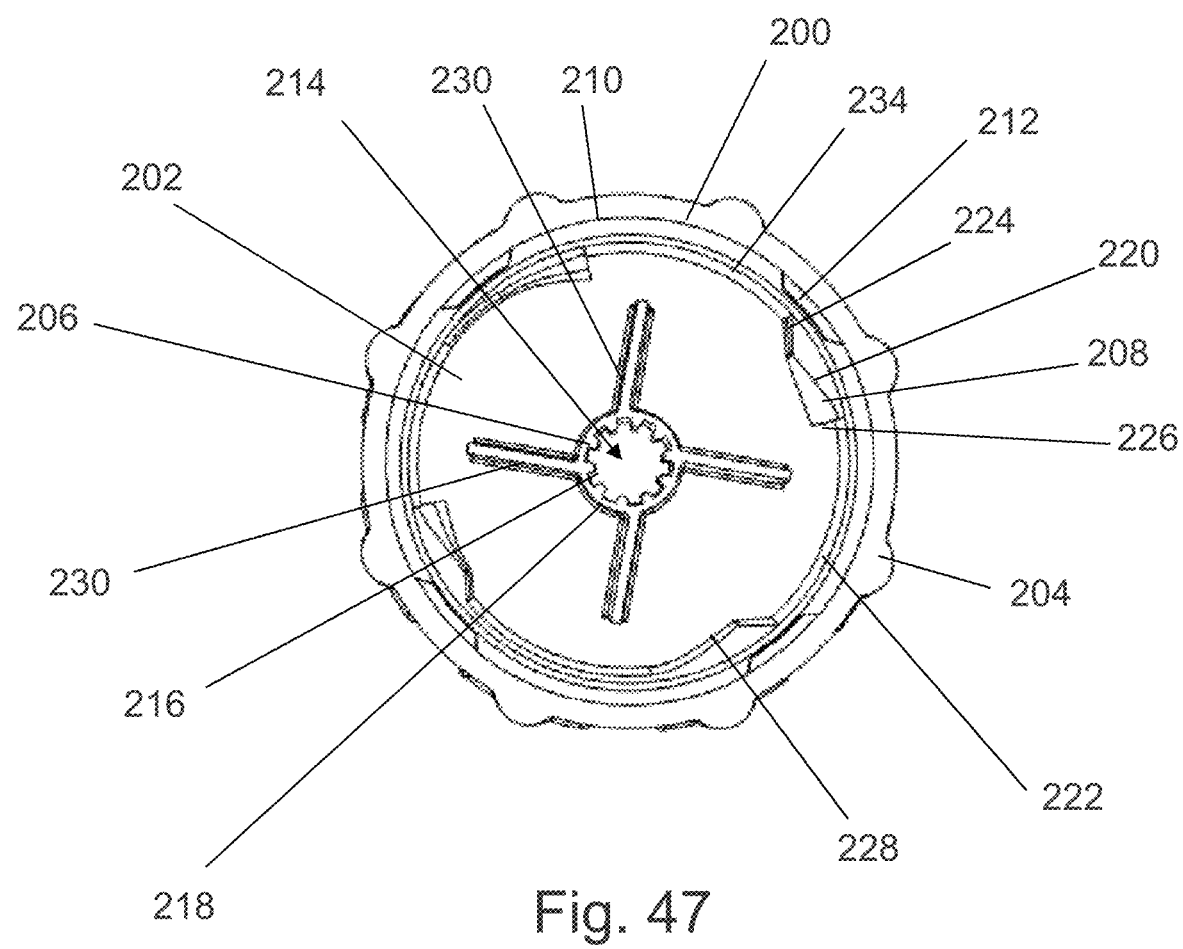
FIG. 47 is a top view of a base of the metering dispenser of FIG. 44.
Figure 48:
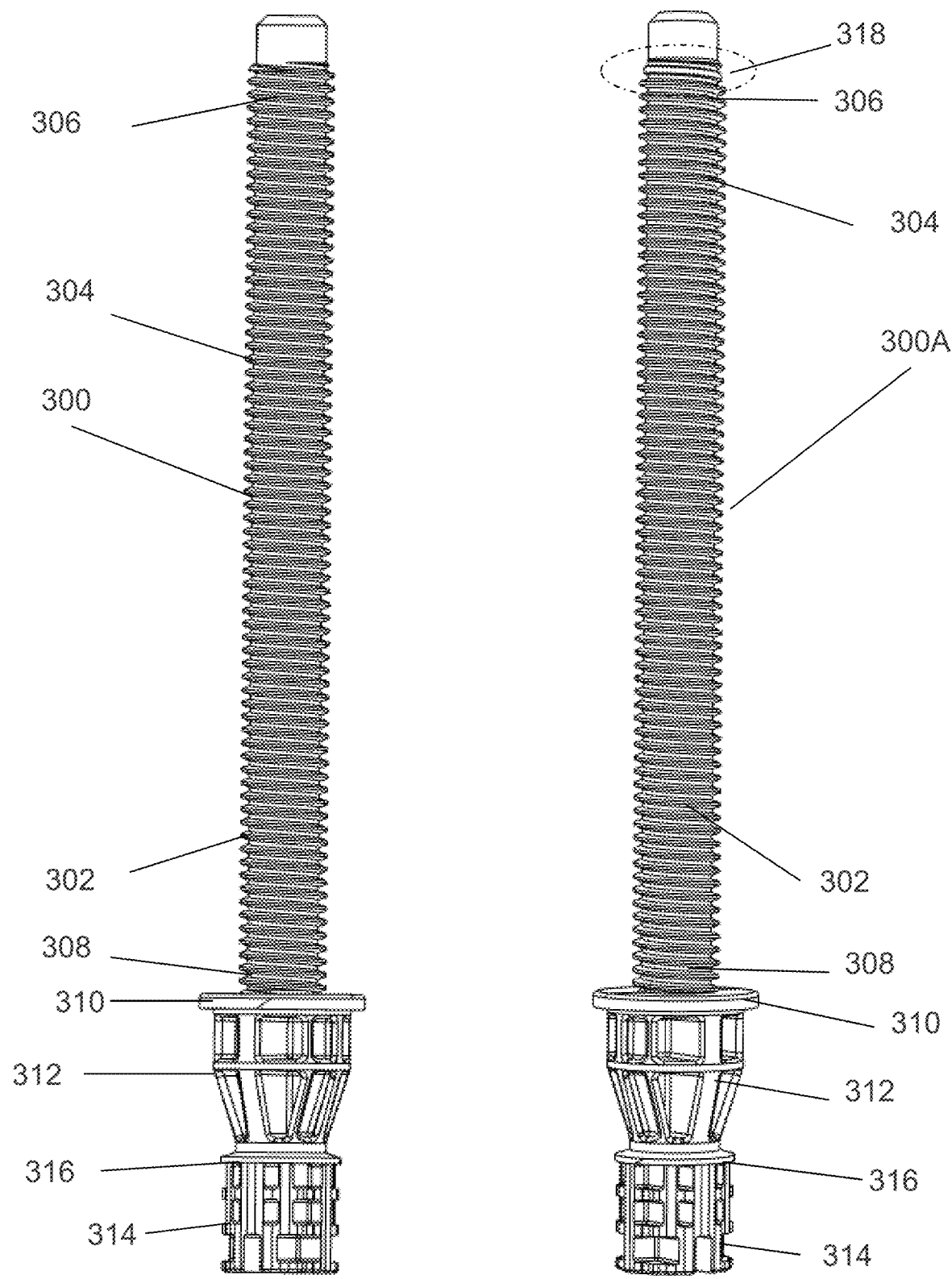
FIG. 48 includes side views of a drive screw without a blocked section, and a drive screw with a blocked section, according to certain embodiments of the present invention.

In certain embodiments, the cam 208 is arranged around a circumferential outer surface 218 of the bushing 206, as shown in FIG. 7, but in other embodiments, may be arranged around an inner perimeter 234 of the sidewall 204, as shown in FIG. 47. The cam 208 may comprise a plurality of ratchet steps 220 that may be configured to induce radial bending of at least one of the tabs 114 when the base 200 is coupled to the external lower rim 122 of the body 100 and rotated between home or "click" positions.

Figure 6:
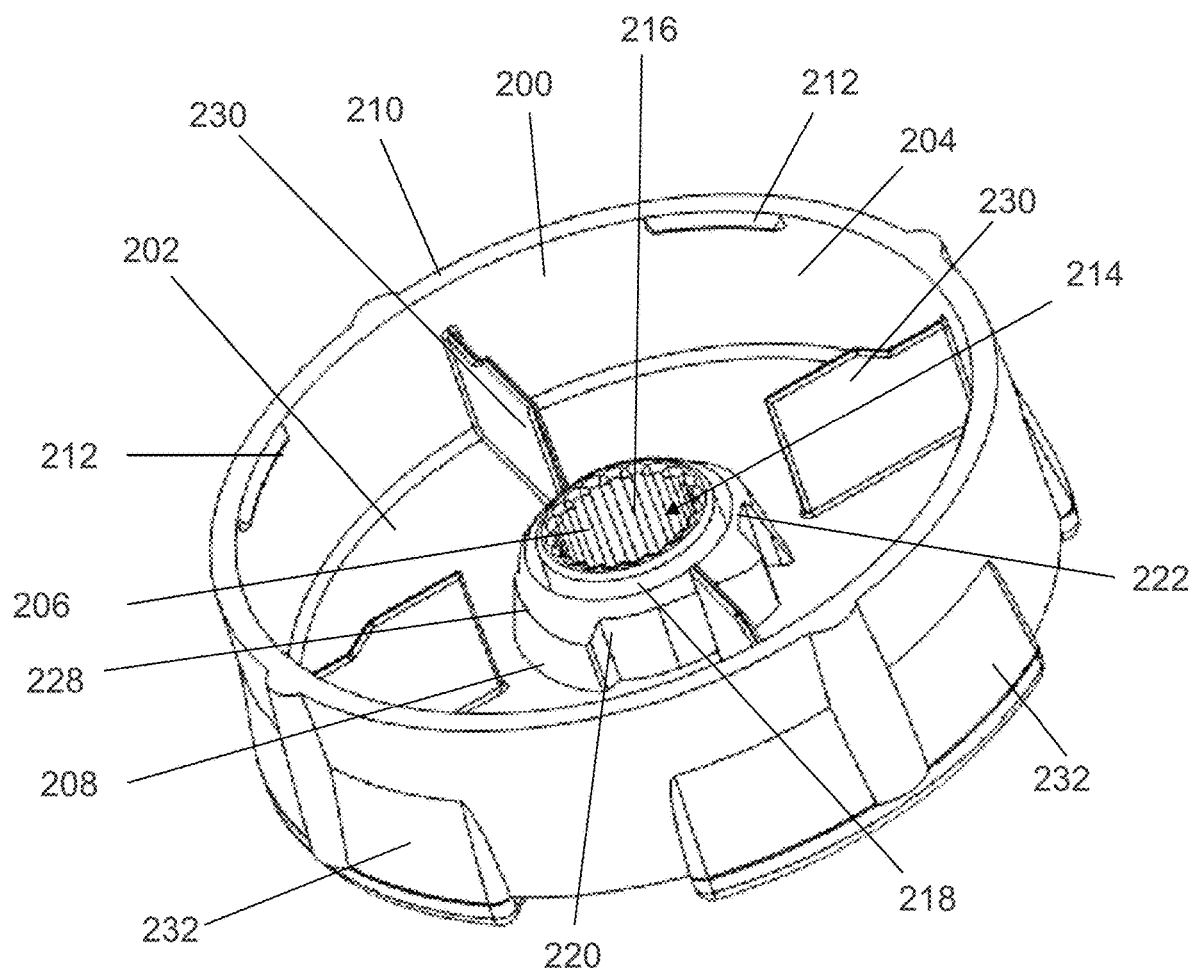
FIG. 6 is a perspective view of a base of the metering dispenser of FIG. 1.
Figure 8:
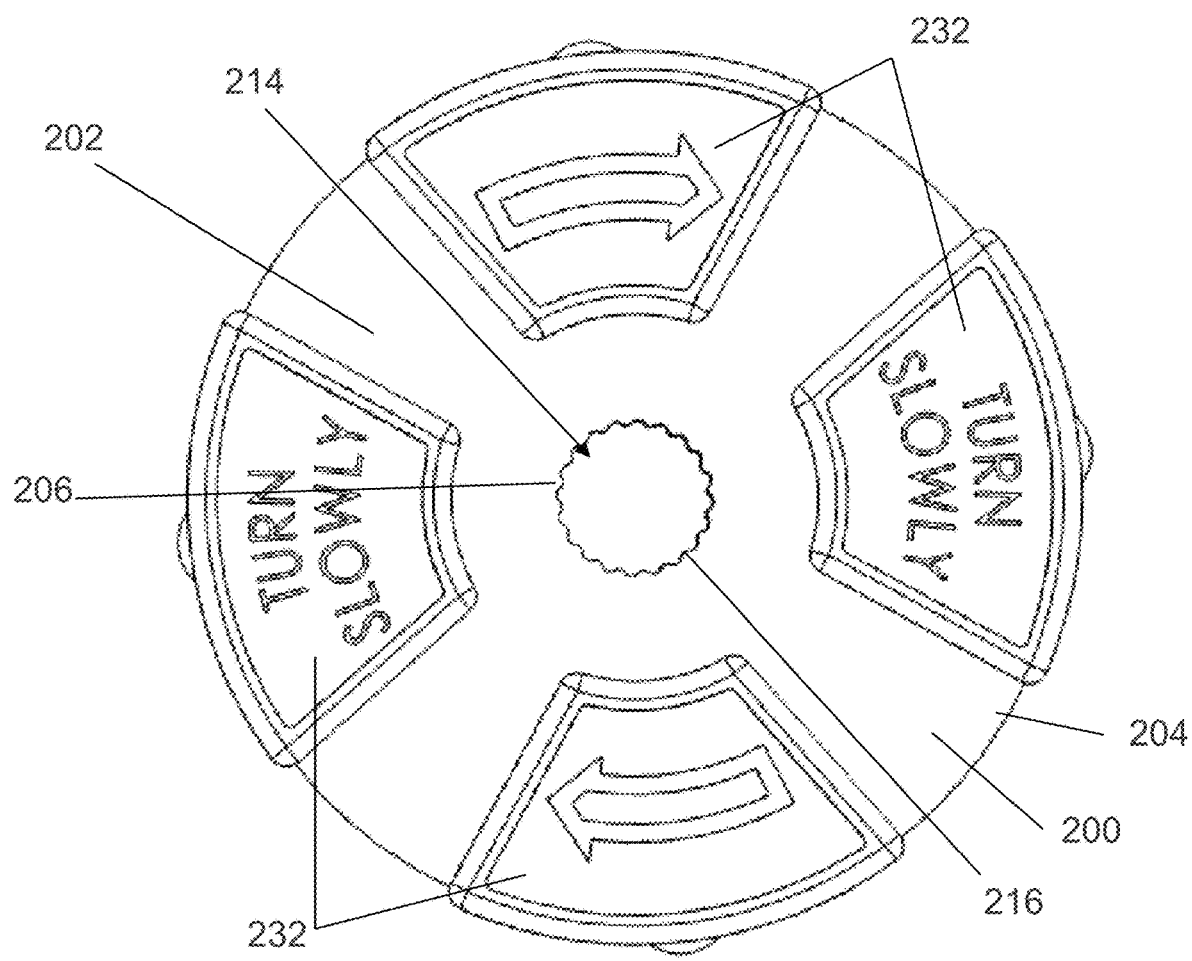
FIG. 8 is a bottom view of the base of FIG. 6.
Figure 9:
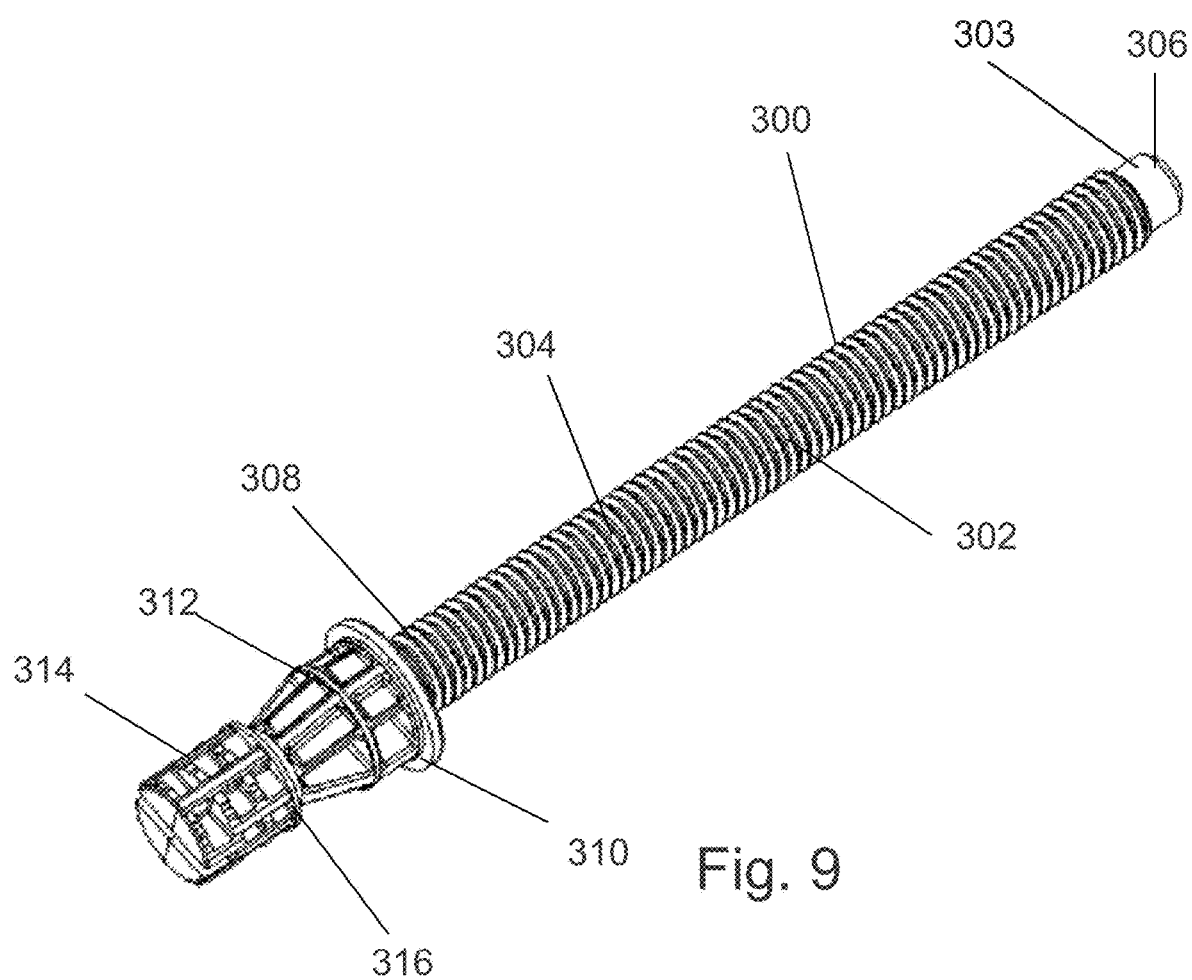
FIG. 9 is a perspective view of a drive screw of the metering dispenser of FIG. 1.
Figure 10:
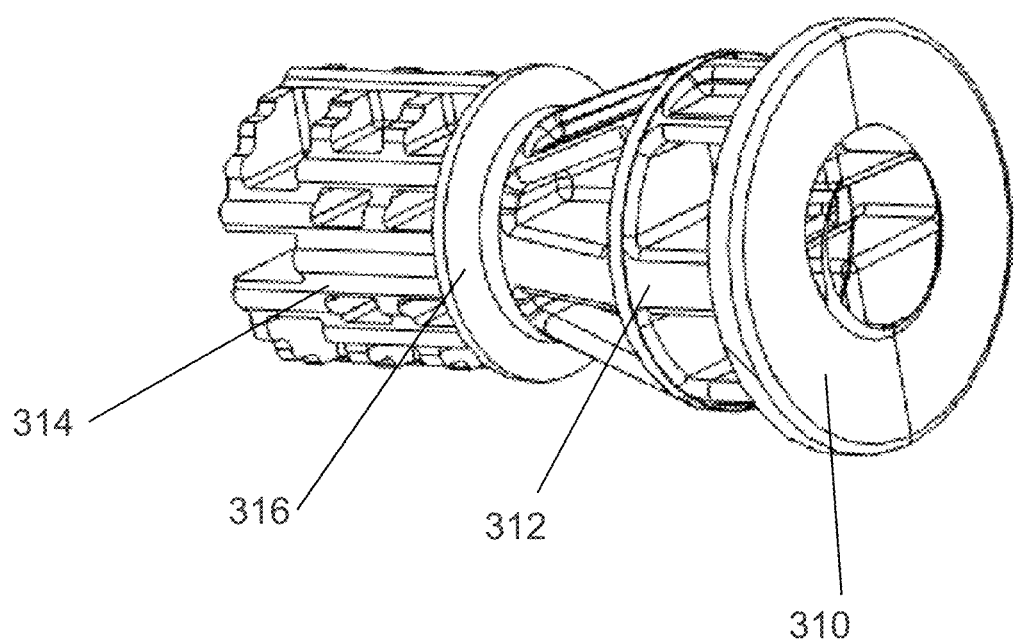
FIG. 10 is a partial perspective view of the drive screw of FIG. 9.
Figure 11:
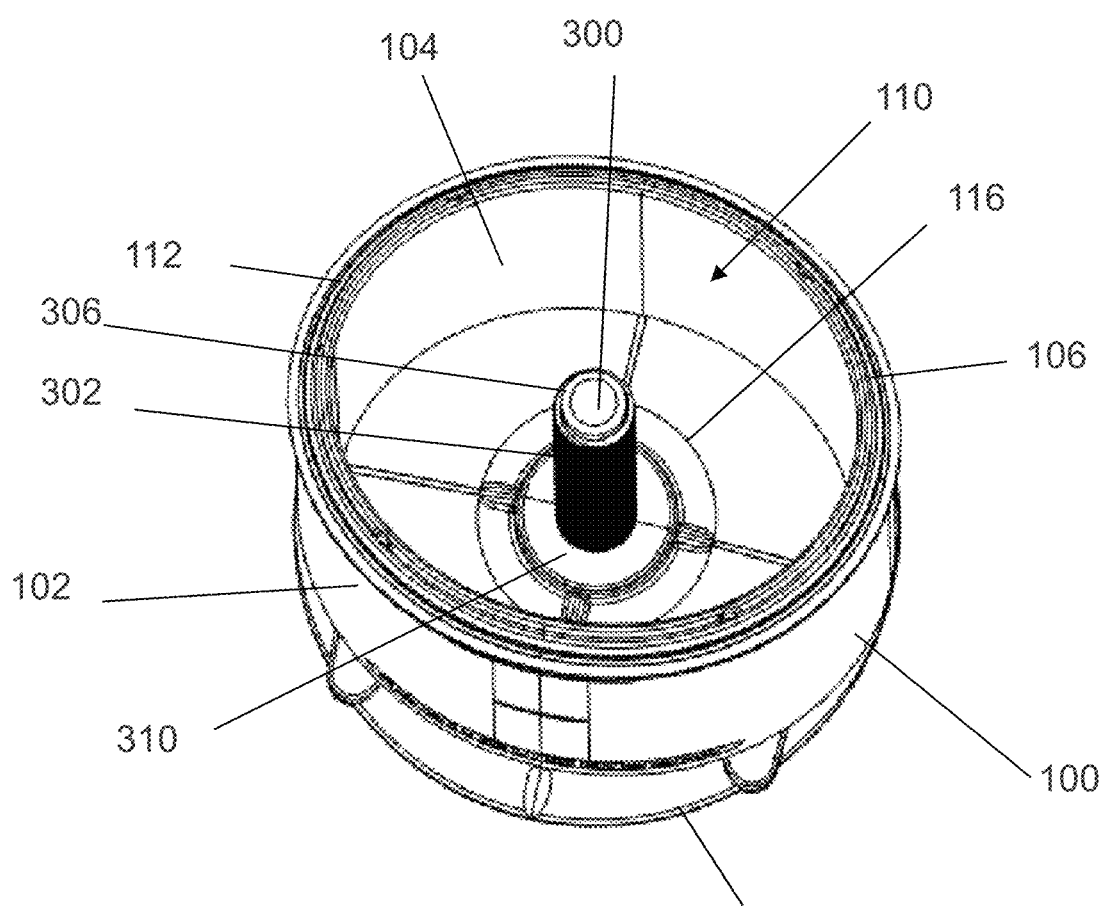
FIG. 11 is a perspective view of the drive screw of FIG. 9 combined with the body of FIG. 2.
Figure 12:
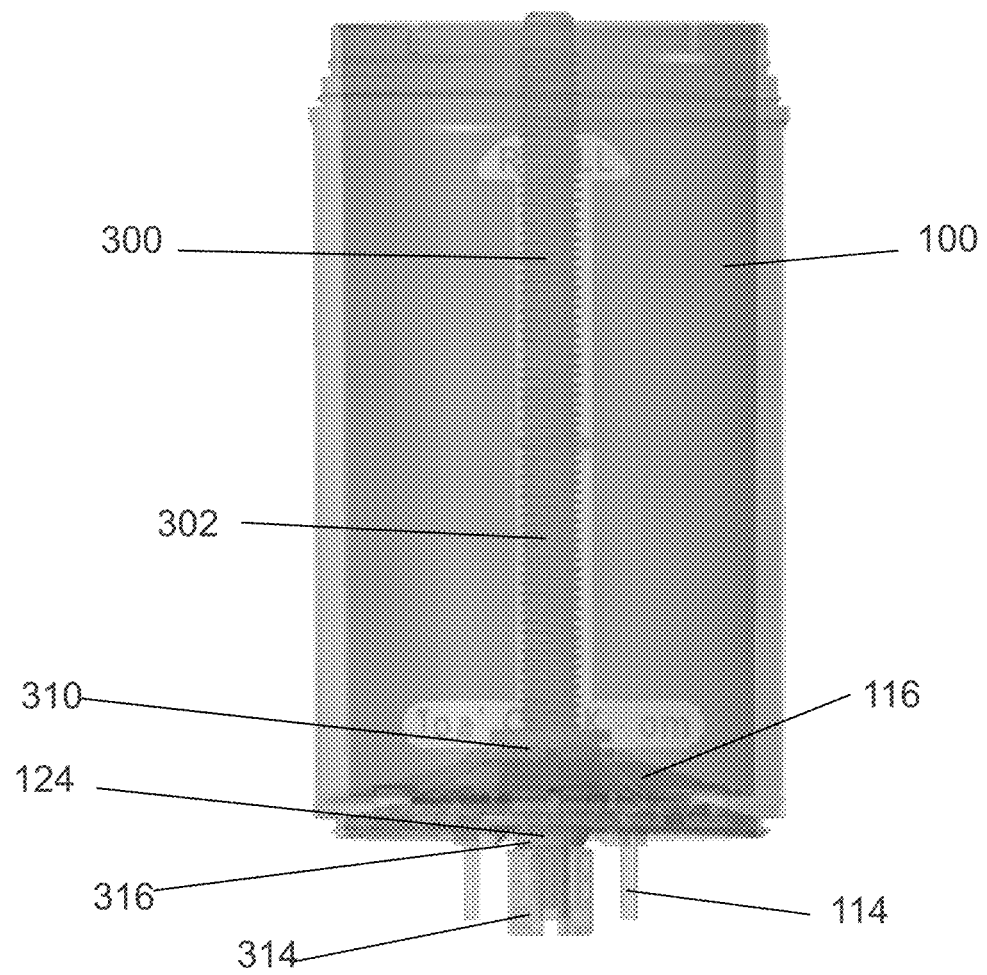
FIG. 12 is a partially transparent front view of the drive screw of FIG. 9 combined with the body of FIG. 2.
Figure 13:
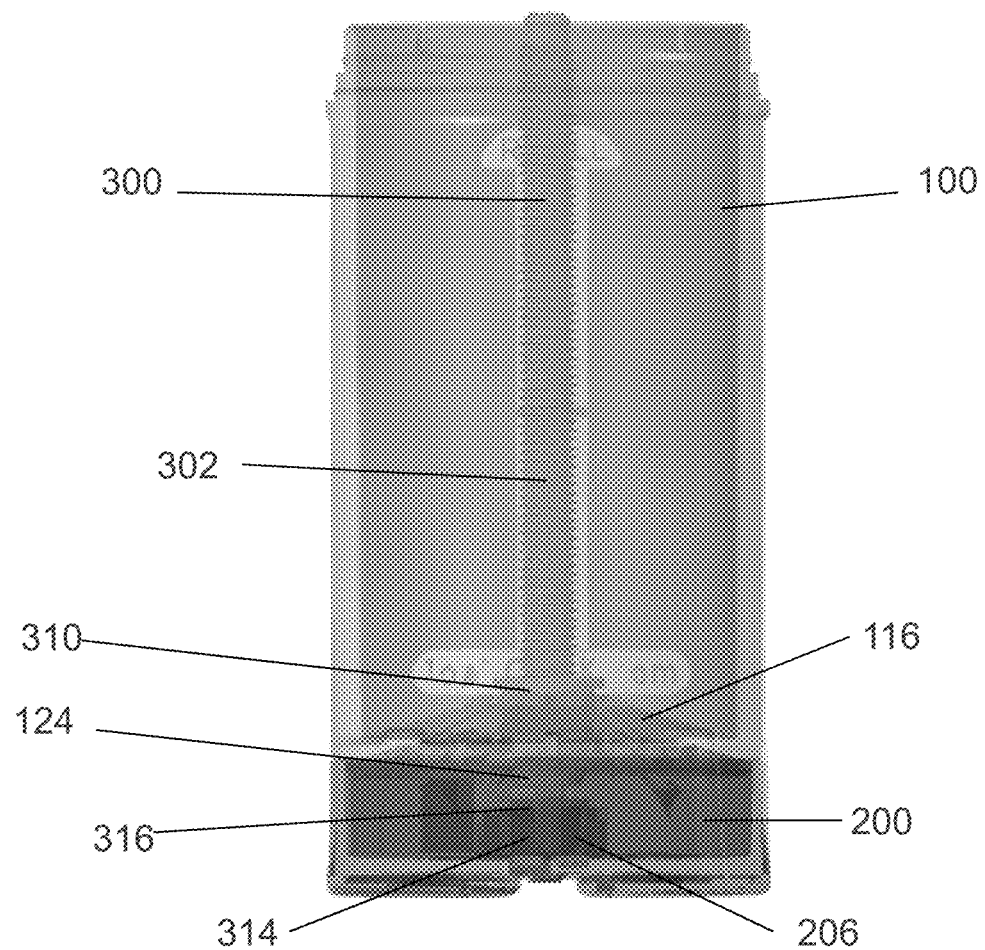
FIG. 13 is a partially transparent front view of the drive screw of FIG. 9 combined with the body of FIG. 2 and the base of FIG. 6.
Figure 14:
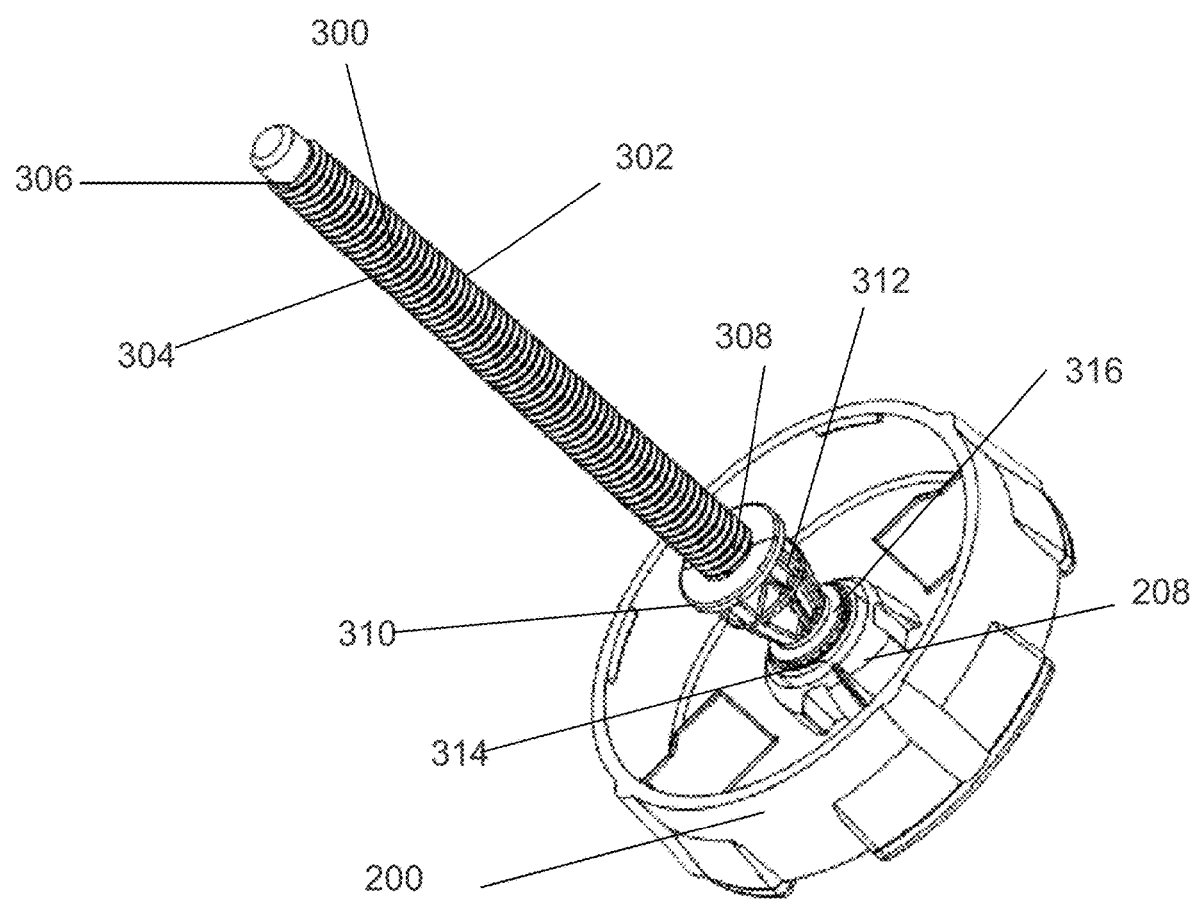
FIG. 14 is a perspective view of the drive screw of FIG. 9 combined with the base of FIG. 6.
Figure 15:
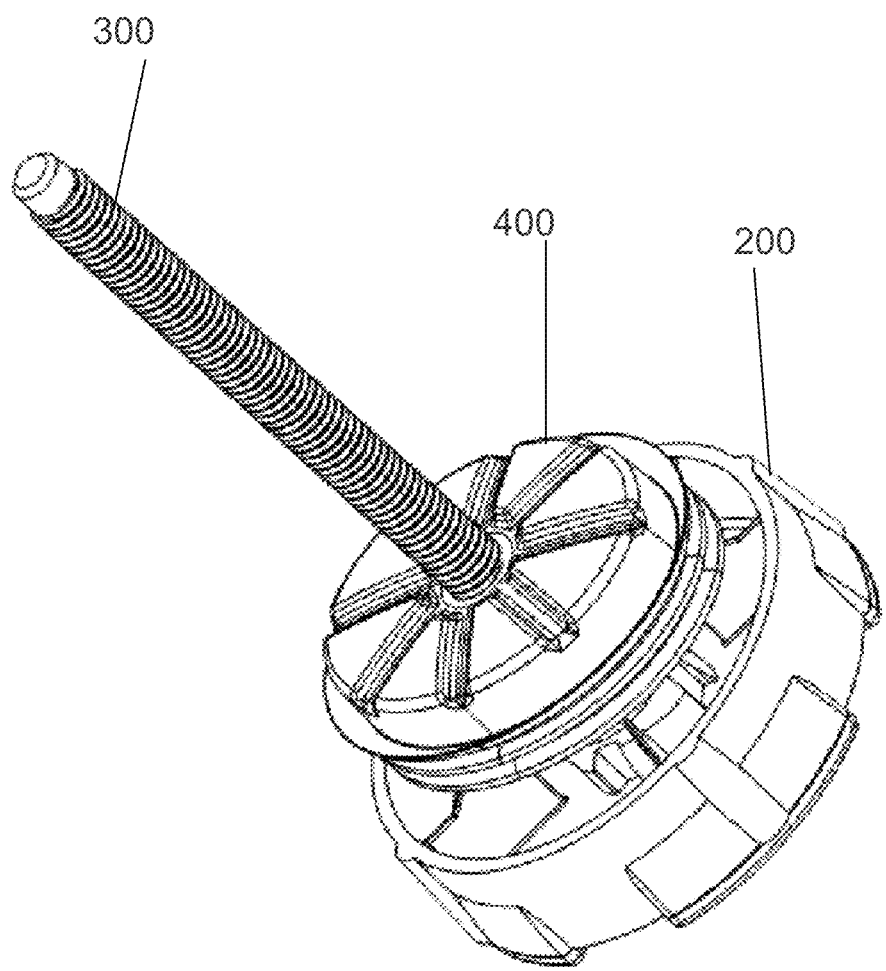
FIG. 15 is a perspective view a plunger of the metering dispenser of FIG. 1 combined with the drive screw of FIG. 9 and the base of FIG. 6.
Figure 16:
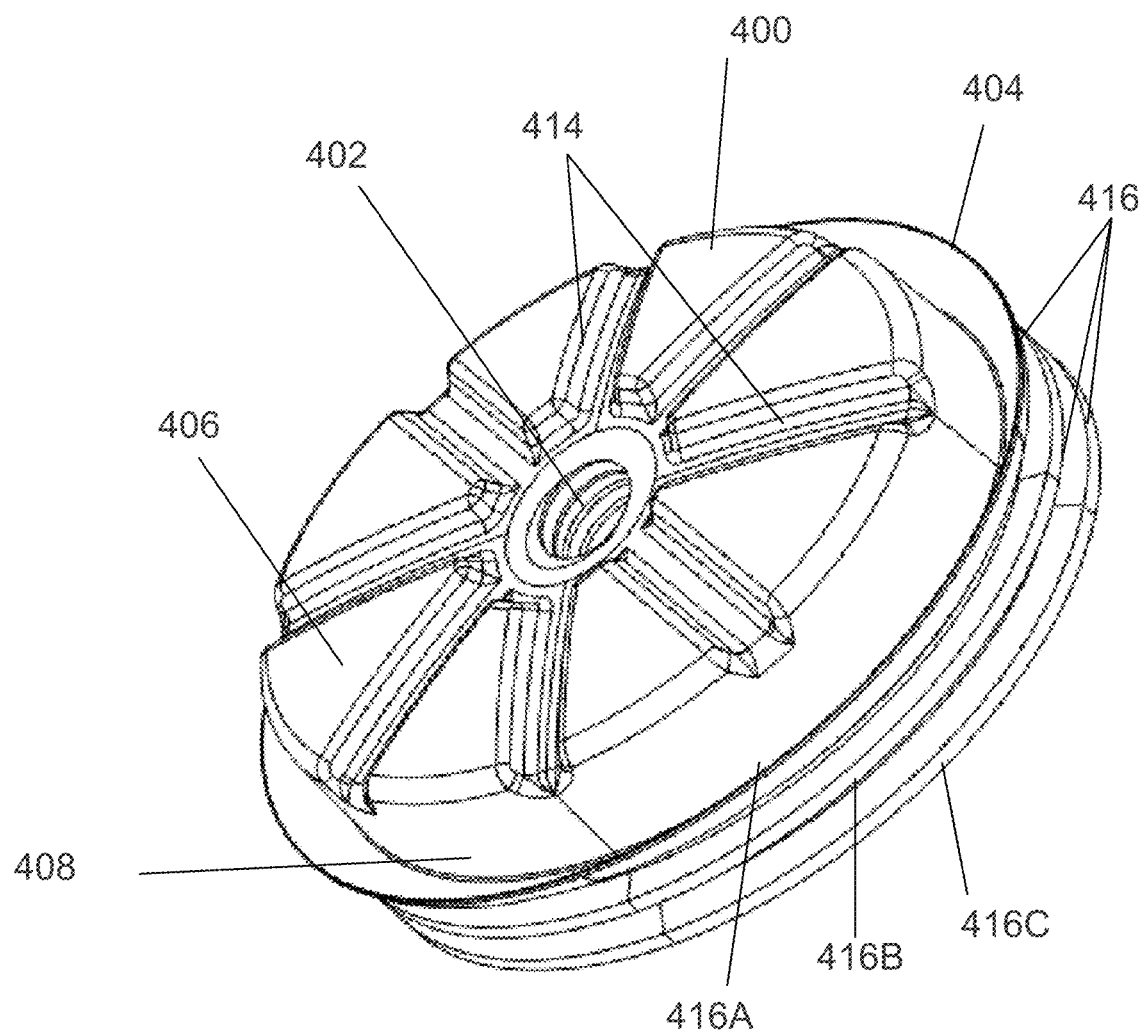
FIG. 16 is a perspective view of the plunger of FIG. 15.
Figure 17A:
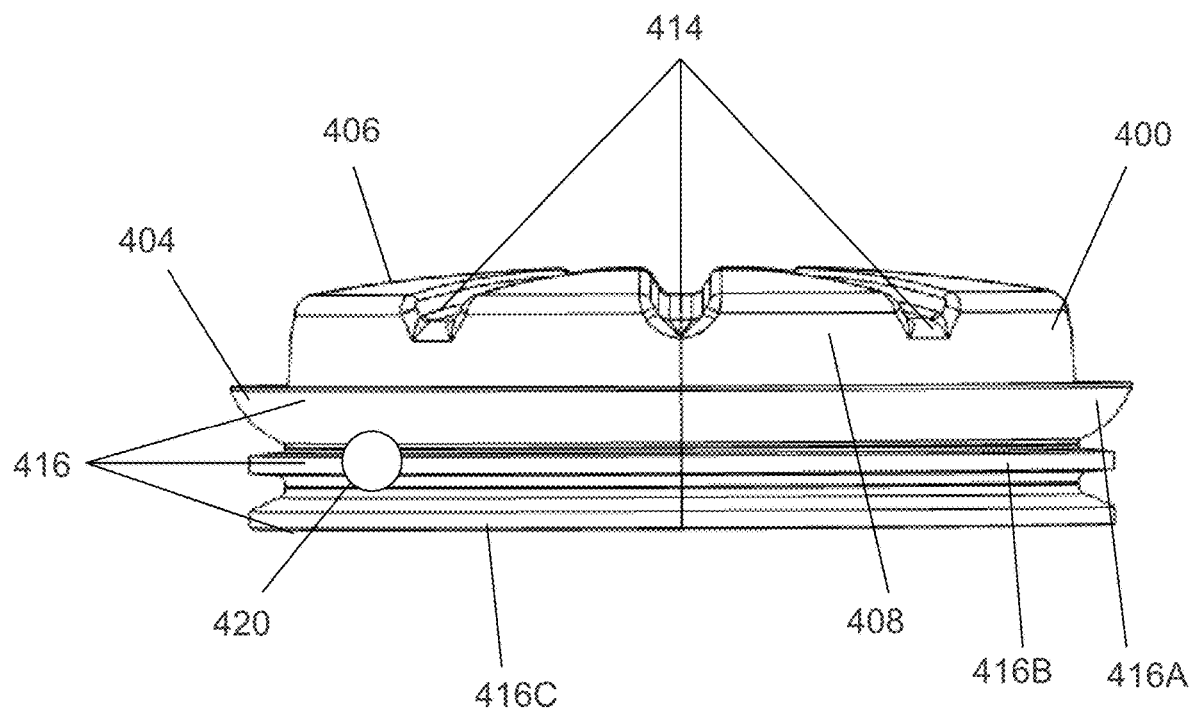
FIG. 17A is a front view of the plunger of FIG. 15.
Figure 17B:
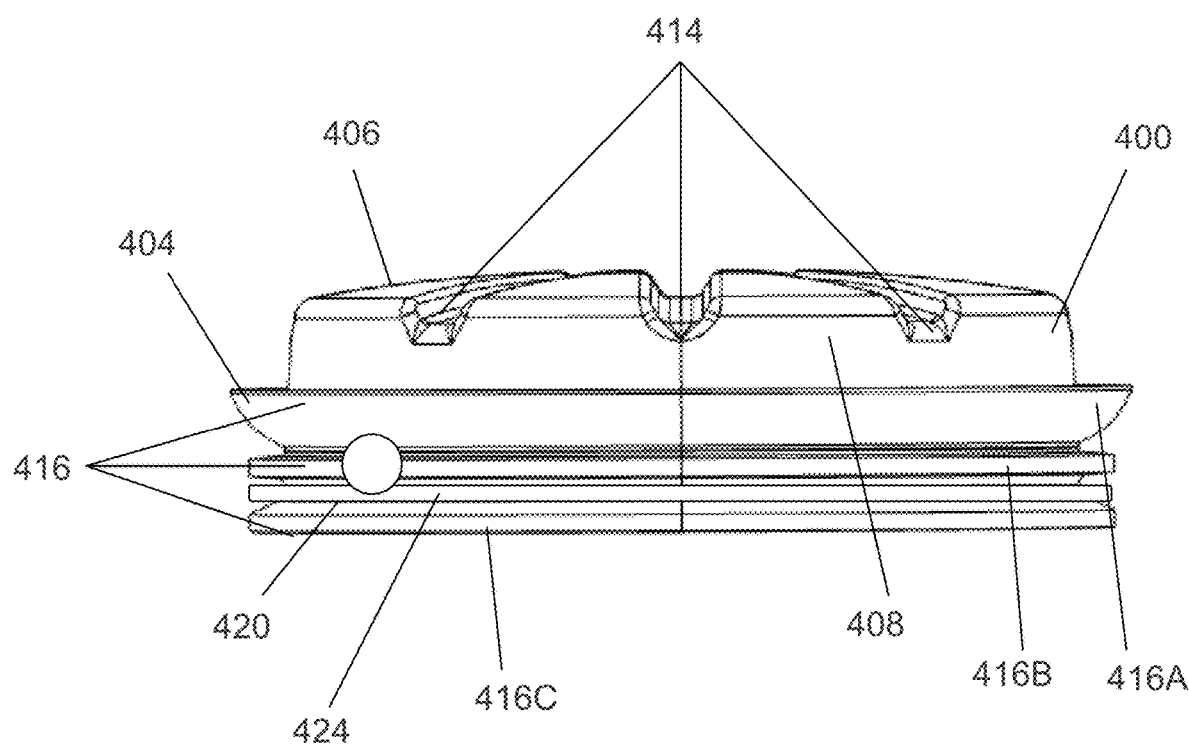
FIG. 17B is a front view of the plunger of FIG. 15 with an O-Ring.
Figure 18:
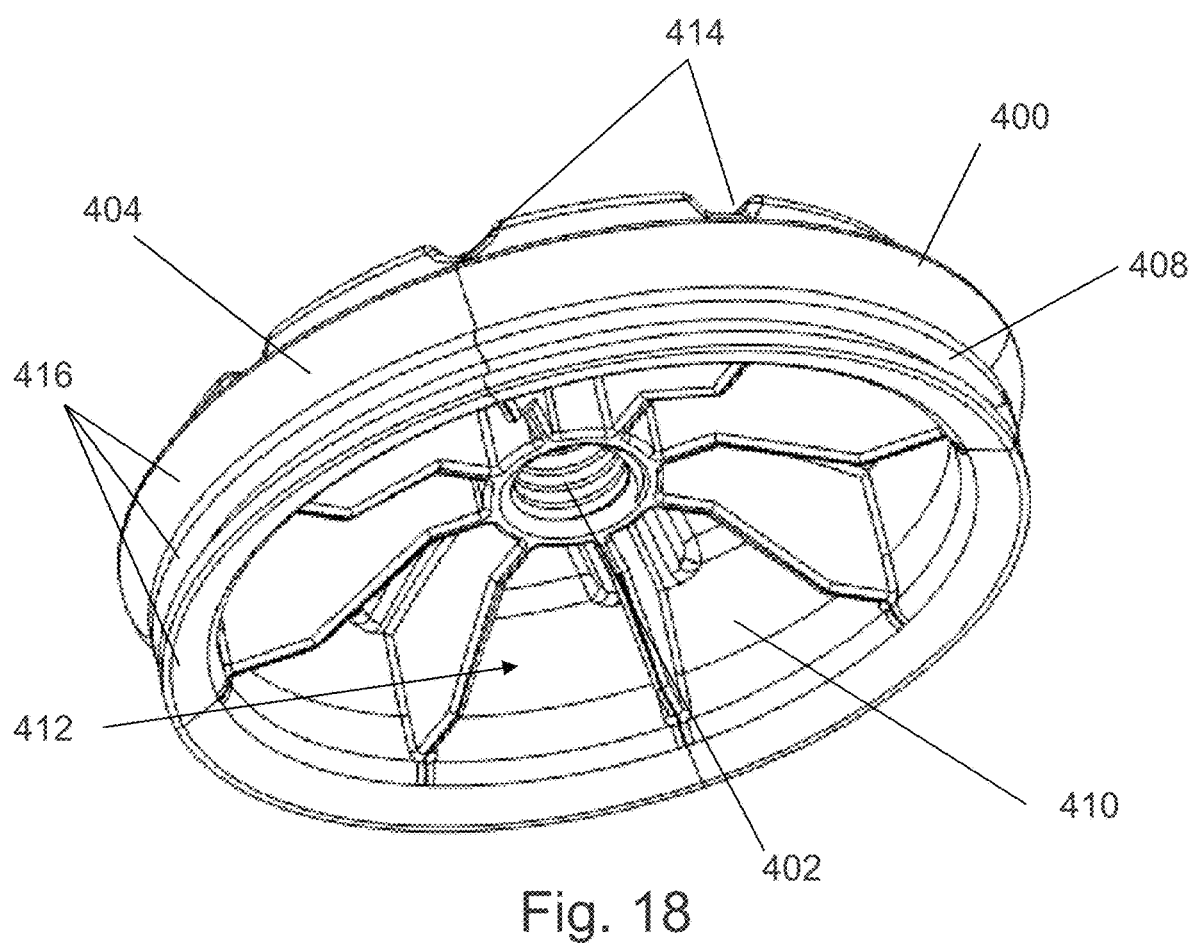
FIG. 18 is a bottom perspective view of the plunger of FIG. 15.
Figure 19:
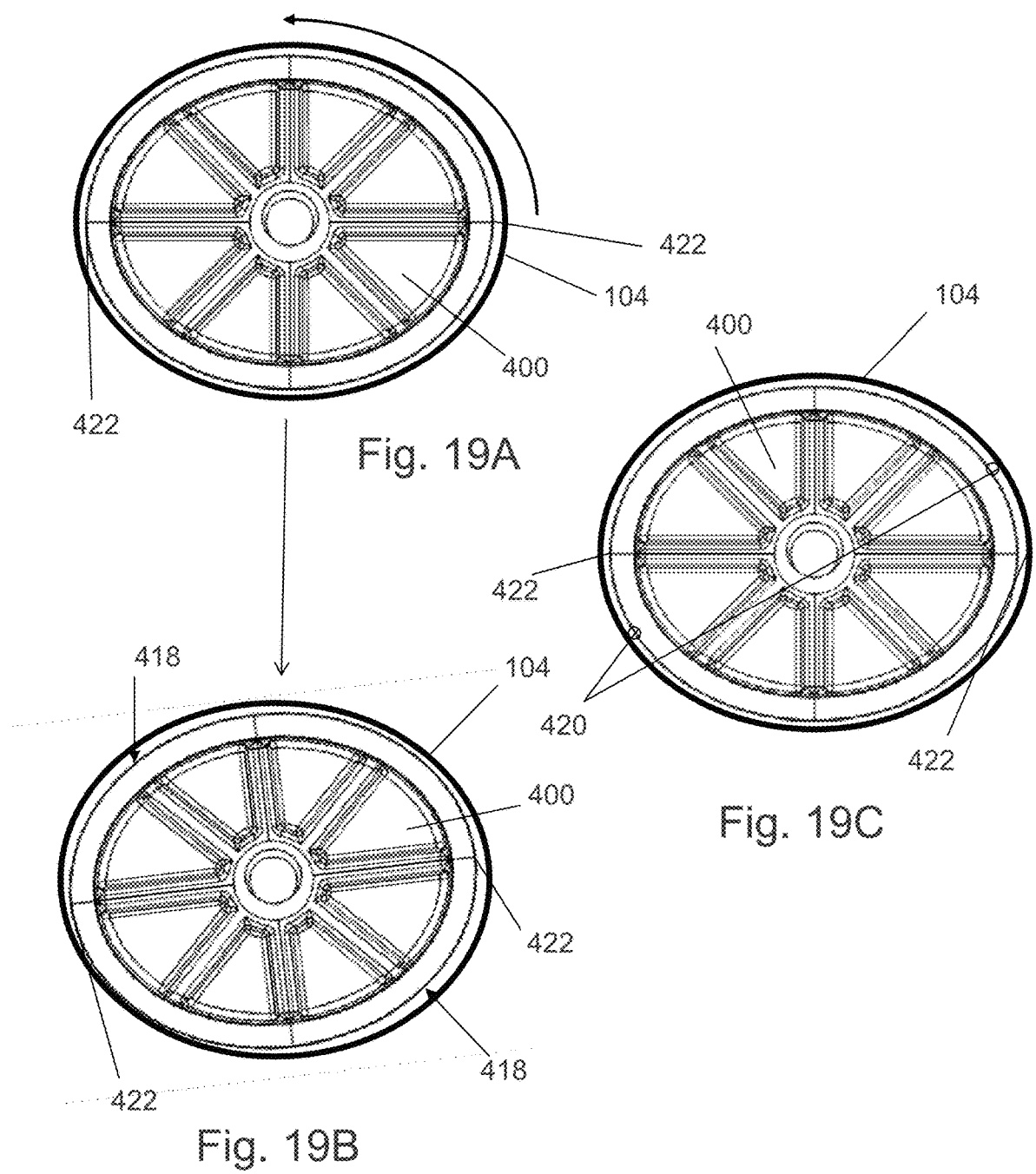
FIGS. 19A and 19B are top views of the plunger of FIG. 15 positioned inside the chamber of FIG. 4 before and after a turning force is applied to the plunger.
FIG. 19C is a top view of the plunger of FIG. 15 positioned inside the chamber of FIG. 4 with anchors to prevent rotation of the plunger within the chamber.
Figure 20:
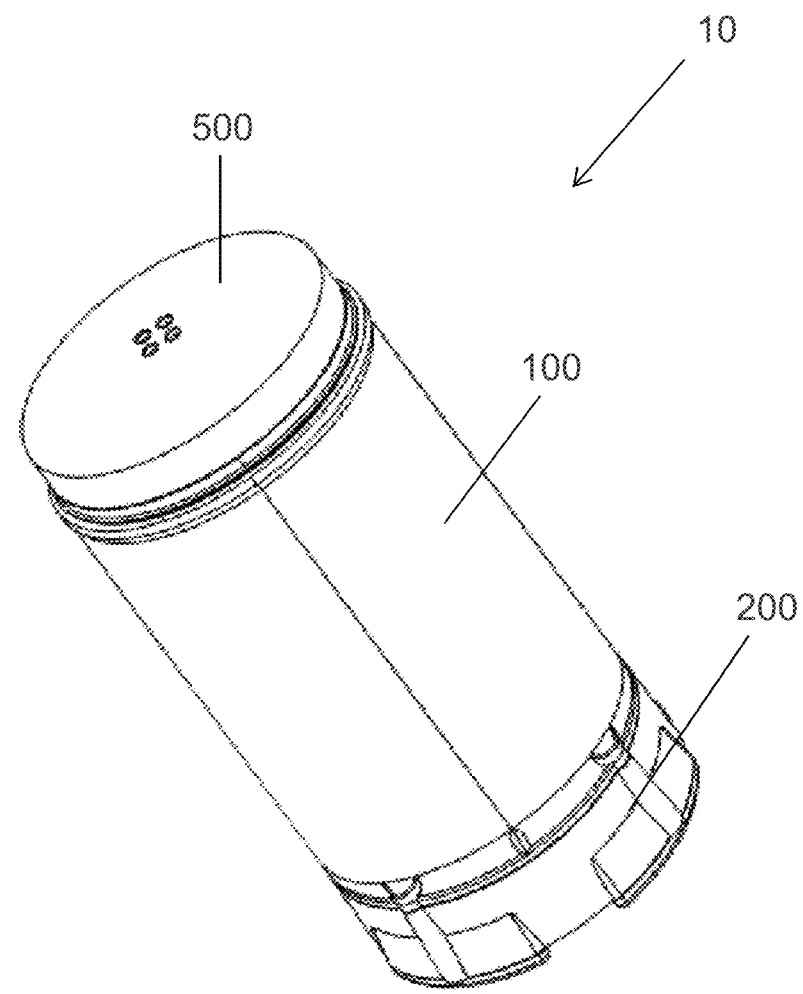
FIG. 20 is a perspective view of the metering dispenser of FIG. 1 with a cap removed so that an administering tool is visible.
Figure 21:
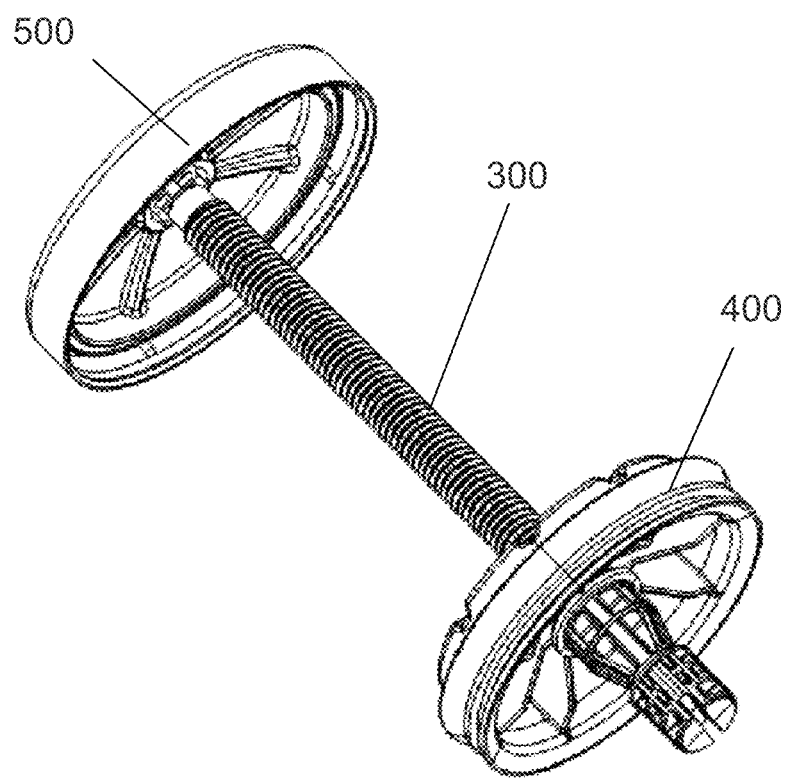
FIG. 21 is a perspective view of the administering tool of FIG. 20 combined with the drive screw of FIG. 9 and the plunger of FIG. 15.
Figure 22:
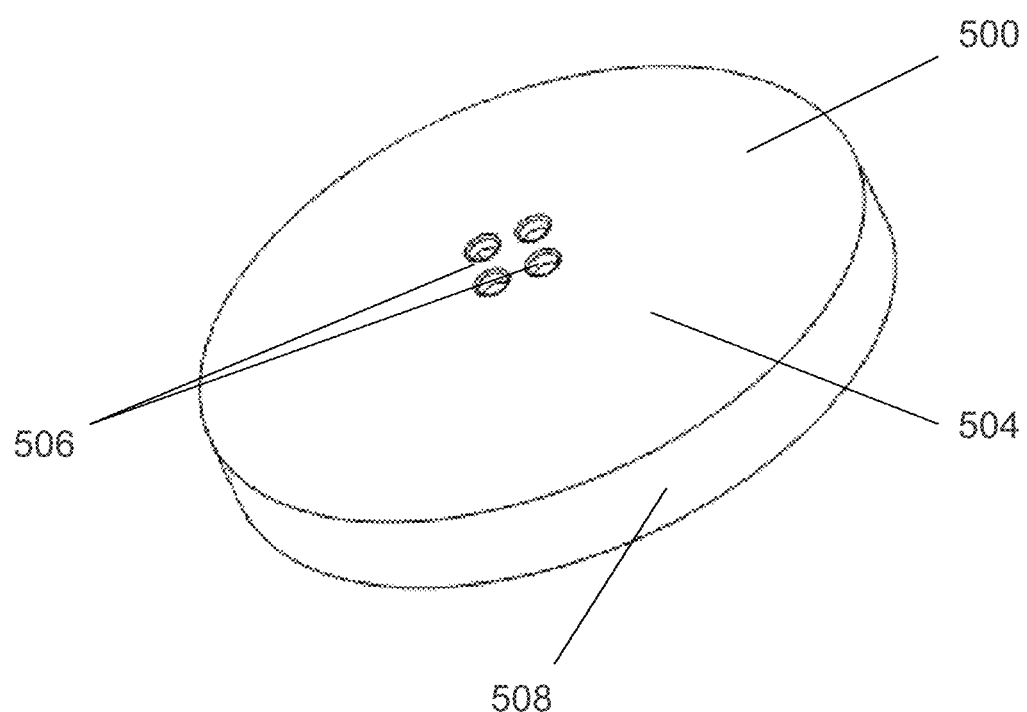
FIG. 22 is a perspective view of the administering tool of FIG. 20.
Figure 23:
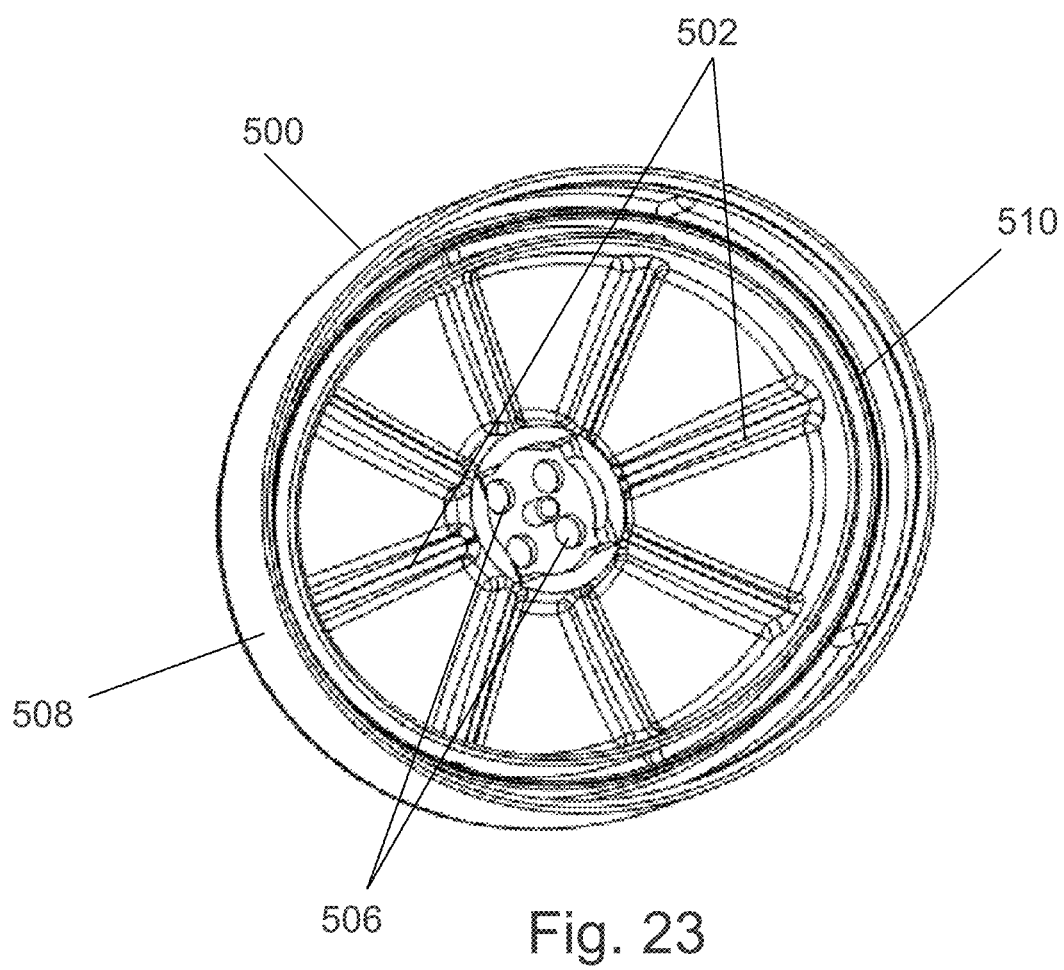
FIG. 23 is a bottom perspective view of the administering tool of FIG. 20.
Figure 46:
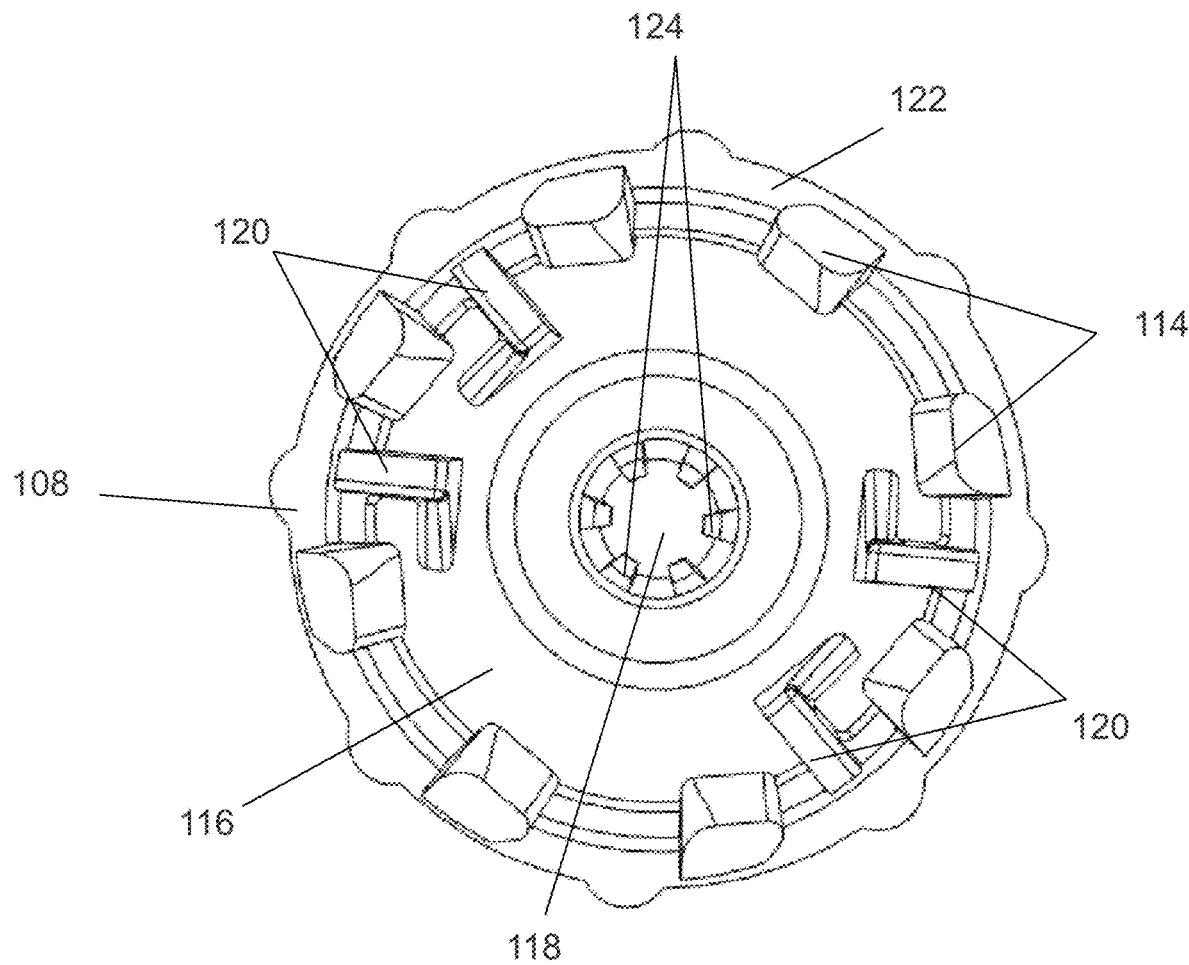
FIG. 46 is a bottom view of the body of FIG. 45.

For example, the cam 208 may be shaped to fit within the tabs 114 (as shown in FIGS. 6-8) or around the tabs 114 (as shown in FIGS. 46-47) so that the tabs 114 ride along the cam 208 as the base 200 rotates. The cam 208 may include at least one low point 222 that is shaped so that the cam 208 does not exert sufficient radial force on the tab 114 that is positioned within the low point 222, which allows the tab 114 to remain in a non-bent or relaxed position.

In certain embodiments, as shown in FIGS. 6-8, the cam 208 comprises the same number of low points 222 as tabs 114. In other embodiments, as shown in FIGS. 46-47, the cam 208 may comprise fewer low points 222, but which are wide enough to accommodate more than one tab 114 at any given time. The low points 222 are positioned so that all tabs 114 are positioned within a low point 222 when the cam 208 is in a home or "click" position. As a result, in these embodiments, in one complete rotation, the cam 208 comprises as many home or "click" positions as there are tabs 114. For example, in embodiments that comprise four tabs 114, the cam 208 may have four home or "click" positions within one complete rotation of the cam 208. In other embodiments that comprise more than four tabs 114 (such as the embodiments illustrated in FIGS. 44-45), the cam 208 may have as many home or "click" positions within one complete rotation of the cam 208 as there are tabs 114. In certain embodiments, the engagement between the tabs 114 and the cam 208 results in home positions at predetermined angular positions around one complete rotation of the cam 208.

At least one of the low points 222 may comprise a saw-toothed shape, wherein a leading edge 224 has a somewhat gradually inclining sloped shape that facilitates movement of the tab 114 in the direction of the leading edge 224, and wherein a trailing edge 226 has a squared or otherwise steep slope that resists movement of the tab 114 in the direction of the trailing edge 226. As a result, the tab 114 locks with the trailing edge 226 of the low point 222 to prevent rotation of the base 200 in the direction of the trailing edge 226 when at least one tab 114 is positioned within the low point 222 having the saw-toothed shape.

In certain embodiments, at least one cam lobe 228 is positioned between two of the low points 222. Some or all of the cam lobes 228 may have the same contoured surface or each cam lobe 228 may have a different contoured surface, depending on the purpose for each cam lobe 228.

For example, as the cam 208 rotates from a home or "click" position, each tab 114 that is positioned proximate a cam lobe 228 may be moved up the leading edge 224 of the low point 222 and onto the cam lobe 228 (unless the low point 222 does not include a leading edge 224). In some cases, particularly where the purpose of the cam lobe 228 is to radially bend the tab 114 away from the relaxed position in the low point 222, the cam lobe 228 may have a minimally declining sloped shape to ensure that the tab 114 is sufficiently radially bent so as to emit an audible "click" when the tab 114 travels from the cam lobe 228 and down the trailing edge 226 of the next low point 222 (unless the next low point 222 does not include a trailing edge 226).

In other embodiments, at least one of the cam lobes 228 may be shaped to provide a gradually declining sloped shape that meets with a leading edge 224 of a low point 222. In these embodiments, such a low point 222 may not comprise a trailing edge 226 (or the trailing edge 226 is shaped to follow substantially the same gradually declining sloped shape of the cam lobe 228). As a result, these low points 222 are not configured to prevent the base 200 rotating in the direction of the trailing edge 226 when at least one tab 114 is positioned within a low point 222 that is configured in this manner.

In yet other embodiments, at least one of the low points 222 may not comprise a leading edge 224 (or the leading edge 224 is shaped so as to follow the same slope of the leading cam lobe 228). In these embodiments, the low point 222 meets with the cam lobe 228 without the leading edge 224 transition therebetween.

In certain embodiments, a plurality of protrusions 230 may be coupled to the inner perimeter 234 of the sidewall 204 (as shown in FIGS. 6-8) or to an circumferential outer surface 218 of the cam 208 (as shown in FIGS. 46-47). At least one of the plurality of protrusions 230 may be positioned to encounter at least one of the projections 120 located on the body plate 116 of the body 100, as the base 200 is returning to one of the home or "click" positions. The protrusion 230 is bent by the projection 120 as the protrusion 230 travels over the projection 120. The protrusion 230 and the projection 120 are positioned so that the protrusion 230 clears the projection 120 and emits an audible sound or "click" when the protrusion 230 returns to an unbent position when the base 200 reaches the next home or "click" position. Thus, in certain embodiments, the interaction between at least one of the protrusions 230 and at least one of the projections 120 may provide the audible sound or "click" response, while the interaction between at least one of the tabs 114 and the cam 208 merely provide the anti-reverse rotation feature. In other embodiments, the interaction between at least one of the protrusions 230 and at least one of the projections 120 may provide a back-up audible sound or "click" to the audible sound or "click" that is also produced by the interaction between at least one of the tabs 114 and the cam 208.

In certain embodiments, the bottom portion 202 of the base 200 may optionally include one or more feet 232 extending outwardly from the bottom portion 202 to assist in stabilizing the dispenser 10 when in a standing position and to facilitate gripping of the base 200 by a user.

As briefly mentioned above, the base 200 couples to the drive screw 300. The drive screw 300 also couples to the body 100.

In certain embodiments, as best illustrated in FIGS. 9-15, the drive screw 300 comprises an elongated shaft 302 having at least one external thread 304, a first end 306, and a second end 308. An unthreaded portion 303 may be between the at least one external thread 304 and the first end 306. In certain embodiments, a first side of a screw plate 310 is coupled to the second end 308. A first end of a coupling body 312 is then coupled to a second side of the screw plate 310, and the cog 314 is then coupled to a second end of the coupling body 312. The cog 314 may further comprise a lip 316 that is positioned between the coupling body 312 and the cog 314.

In certain embodiments, the drive screw 300 is integrally formed as a single piece. In these embodiments, the cog 314 may be formed with a split spine to allow ease of removal from a mold without resulting in damaged teeth that could otherwise prevent the cog 314 from properly fitting with the bushing 206.

In certain embodiments, at least one tapering finger 124 may be positioned around an outer side of a lip 126 of the aperture 118 in the body plate 116 of the body 100. These tapering fingers 124 may be arranged so as to project in a direction away from the chamber 110.

The drive screw 300 is inserted into the body 100 so that the cog 314 passes through the aperture 118 in the body plate 116. The tapering fingers 124 may be shaped so that insertion of the cog 314 exerts pressure against the tapering fingers 124, thereby causing the opening formed by the tapering fingers 124 to slightly expand to allow the cog 314 to pass therethrough. Once the cog 314 passes through the tapering fingers 124, the pressure against the tapering fingers 124 is released, and the tapering fingers 124 are then arranged along the coupling body 312 so that tips of the tapering fingers 124 contact the lip 316 of the cog 314. The combination of the tapering fingers 124, the shape of the cog 314, and the body plate 116 form a radial engagement structure that maintains the position of the drive screw 300 within the body 100.

At this point, the second side of the screw plate 310 located at the first end of the coupling body 312 is positioned adjacent an inner side of the body plate 116 of the body 100 so that the screw plate 310 overlaps an inner side of the lip 126 of the aperture 118. The body plate 116 is positioned to prevent the drive screw 300 from passing any further through the aperture 118. In certain embodiments, such as where the flowable composition 20 is a positive viscosity liquid, a seal may be formed between the plates 116, 310 to prevent leakage as needed.

Because the combined length of the thickness of the aperture 118 and the tapering fingers 124 approximates a longitudinal length of the coupling body 312, the coupling body 312 is locked into place by the contact between the plates 116, 310 on the inside of the chamber 110 and the contact between the tapering fingers 124 and the lip 316 of the cog 314.

Because of the arrangement of the tapering fingers 124 on the outside of the chamber 110, the tapering fingers 124 may only be compressed by a force that pushes the cog 314 toward the chamber 110. Application of force to the cog 314 in a direction away from the chamber 110 will not compress the tapering fingers 124 and will therefore be prevented through the rigid mating of the plates 116, 310.

Once the cog 314 is positioned outside the tapering fingers 124, the cog 314 is inserted within the bushing 206 of the base 200. This insertion also positions the tabs 114 arranged on the body plate 116 of the body 100 along the surface of the cam 208 on the base 200, and may also position the projections 120 arranged on the body plate 116 of the body 100 into rotational alignment with the protrusions 230 on the base 200. The lip 212 of the base 200 is then coupled to the external lower rim 122 of the body 100.

As discussed above, the base 200 is configured so that rotation between home or "click" positions along the cam 208 applies an outward radial force to at least one of the tabs 114. In certain instances, if there is any flexibility in the coupling between the body 100 and the base 200, the force applied by the cam 208 to the at least one tab 114 may alternatively and/or additionally apply a longitudinal force to the at least one tab 114, thereby causing the body 100 to move away from the base 200. Such a movement may also result in a longitudinal movement of the plunger 400 within the chamber 110, which may cause leaks or other inaccuracies in metered metering, which is discussed in detail below.

To ensure that the force applied by the cam 208 to the at least one tab 114 does not result in longitudinal movement of the chamber 110 relative to the plunger, the tapering fingers 124 are oriented outward and outside of the chamber, thus eliminating the ability of the chamber 110 to move relative to the plunger 400 in a direction away from the base 200.

To the extent that the force applied by the cam 208 nevertheless results in application of a longitudinal force being applied to the at least one tab 114, the cog 314 may not be longitudinally coupled to the bushing 206, which allows the base 200 to longitudinally travel along a length of the cog 314 as needed. As a result, the cog 314 may be inserted into the bushing 206 and circumferentially coupled to the bushing 206 via the interlocking teeth on the cog 314 and the bushing 206.

In certain embodiments, as best illustrated in FIGS. 15-19, the plunger 400 comprises a centrally located threaded aperture 402 that is configured to couple to the elongated shaft 302 of the drive screw 300. As discussed above, the plunger 400 is shaped to snugly fit within the chamber 110 without freely rotating within the chamber 110 when the base 200 is turned. In certain embodiments, the chamber 110 may be formed with a longitudinal draft that results in some variation in size from top to bottom, with the bottom typically being slightly smaller in cross-sectional area than the top. Also, there may be some variation in sizes among chambers 110 and plungers 400. Therefore, the plunger 400 is configured with a flexible design that provides a fluid seal along the entire length of the chamber 110 and between variations ranging from approximately 0.01% to approximately 25% in cross-sectional area along the longitudinal draft of the chamber 110.

The Table below summarizes variation measurement amount various chamber sizes that were tested with the plunger 400 design. The testing confirmed that there was a fluid seal between the plunger 400 and the chamber 110 as the plunger traveled along the longitudinal draft of the chamber 110.

|  | TC7 | TC15M | TC35 | TC140 |
|---|---|---|---|---|
| Cross-sectional area at top of chamber (in$^2$) | 0.377 | 0.584 | 1.069 | 2.819 |
| Cross-sectional area at bottom of chamber (in$^2$) | 0.322 | 0.523 | 0.966 | 2.578 |
| % Variation | 16.90% | 11.70% | 10.59% | 9.36% |

In these embodiments, the plungers 400 may be formed to have a greater degree of flexibility that allows the plunger 400 to bend or compress as needed to form a fluid seal inside smaller cross-section areas, and to flex or expand as needed to form a fluid seal inside larger cross-section areas. In certain embodiments, the plunger 400 comprises an annular fluid member 404 that comprises a flexible design configured to flexibly bend, compress, flex, and/or expand as needed to allow the plunger 400 to maintain a fluid seal over variations ranging from approximately 0.01% to approximately 25% in cross-sectional area along the longitudinal draft of the chamber 110.

To provide flexibility within the body of the plunger 400 itself, the plunger may have a curved or domed top surface 406 and a sidewall 408 that forms an inner wall 410 defining an interior space 412. In certain embodiments, the top surface 406 may at least one channel 414, which is arranged to mate with at least one reinforcing rib 502 in the administering tool 500 to prevent residual flowable compositions 20 from being trapped between the plunger 400 and the administering tool 500.

The fluid member 404 may comprise at least one annular lip 416, may further comprise at least two annular lips 416, and may include up three or more annular lips 416 as needed to create a fluid seal between the plunger 400 and the inner wall 104 as the plunger 400 travels along the elongated shaft 302 through the chamber 110. In these embodiments, an upper lip 416A may be configured to flex in a direction toward the first end 106 of the body 100 along the inner wall 104 of the chamber 110 to provide the fluid seal, and a lower lip 416C may be configured to flex in a direction toward the second end 108 of the body 100 along the inner wall 104 of the chamber 110 to provide stability and/or anti-rotational support. A middle lip 416B may be configured to be arranged substantially perpendicular to the inner wall 104 of the chamber 110 and/or may be configured to flex in the direction of either the first end 106 or the second end 108 of the body 100 as needed to also provide stability and/or anti-rotational support.

In certain embodiments, as illustrated in FIGS. 19A-19B, the plunger 400 and/or the chamber 110 may not be perfectly shaped to interlock in a manner that prevents all rotational movement of the plunger 400 within the chamber 110. As a result, small gaps 418 may form in certain spaces between the plunger 400 and the inner wall 104 of the chamber 110. To prevent such minor rotational movements, as illustrated in FIG. 19C, at least one anchor 420 may be positioned on at least one leading or lagging rotational point on the plunger 400. For example, in the embodiments where the plunger 400 is oval-shaped, the anchor 420 may be positioned just to the leading rotational side or the lagging rotation side of at least one apex 422 of the plunger 400 so that the anchor 420 will encounter the inner wall 104 when a rotational force is applied to the plunger 400 by the drive screw 300 and prevent the plunger 400 from radial movement within the chamber 110. The anchor 420 may have a diameter of 0.005-0.010 inches. In particular, the anchor 420 acts like a take-up spring to further prevent rotation, which keeps the upper lip 416A from distorting.

In further embodiments, an O-ring 424 may be positioned proximate at least one of the annular lips 416 to assist with and/or to provide a fluid seal between the plunger 400 and the chamber 110.

In certain embodiments, as best illustrated in FIGS. 22, 26, 28, 32, and 44, the administering tool 500 may comprise a curved or domed top surface 504 having at least one hole 506 therein and a sidewall 508. The sidewall 508 may include an inner groove 510 which can be coupled to the external upper rim 112 on the body 100. In these embodiments, the inner groove 510 and the external upper rim 112 may be configured to couple via a snap-fit, screw, latch, or other suitable mechanical fastening design. As discussed above, the administering tool 500 may comprise a plurality of reinforcing ribs 502 positioned on an underside of the top surface 504. In other embodiments, such as where the flowable composition 20 is a positive viscosity liquid, the administering tool 500 may be a nozzle or other device to pour the liquid into a cup or directly into a mouth of a patient.

Figure 24:
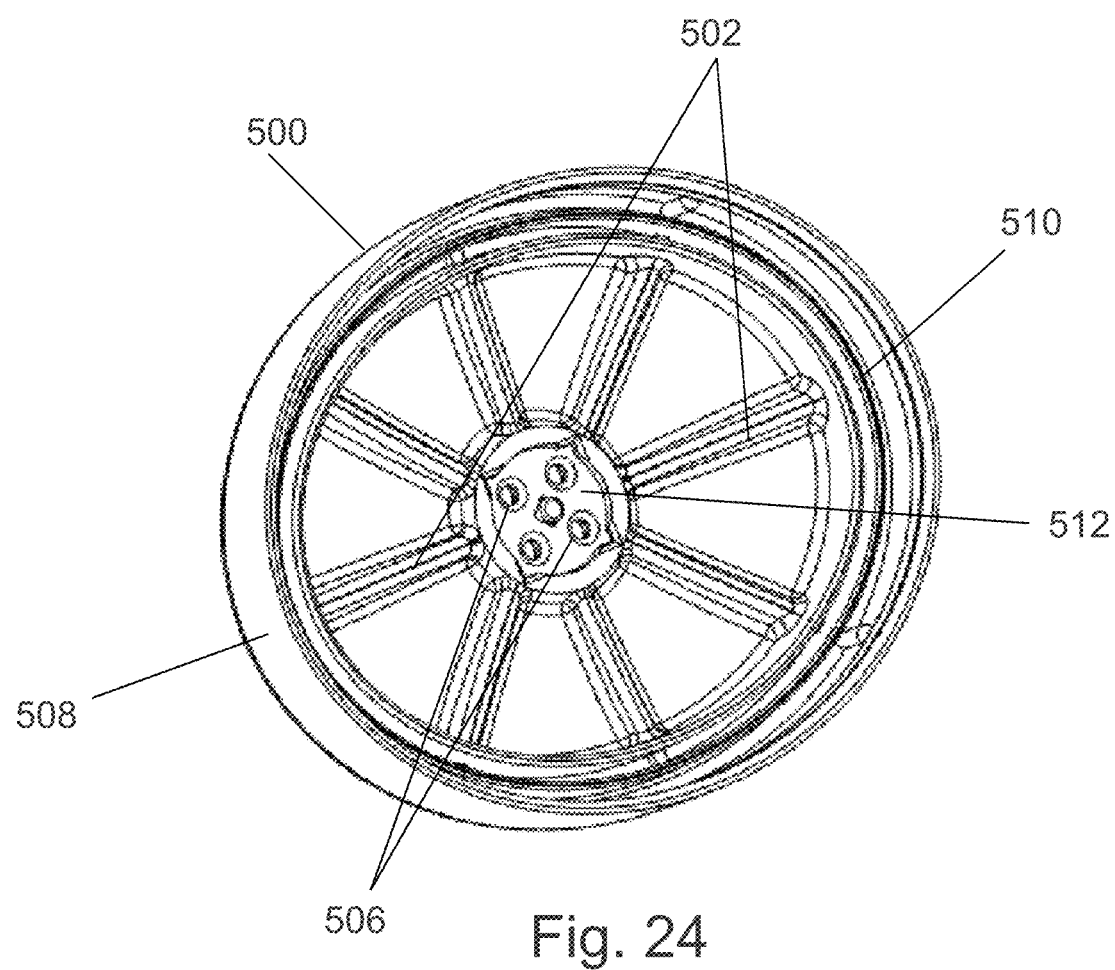
FIG. 24 is another bottom perspective view of the administering tool of FIG. 20 with a restrictor plate.

In certain embodiments, as best illustrated in FIG. 24, a restrictor plate 512 may be incorporated into the administering tool 500 to change the size and/or number of holes 506 to accommodate flowable compositions 20 of differing viscosities. For example, a highly viscous composition (such as a topical cream) may require more holes and/or larger holes to pass through the administering tool 500, whereas a less viscous composition (such as cough syrup) may require fewer holes and/or smaller holes to prevent the composition from spraying out of the administering tool 500 when the base 200 is rotated.

In certain embodiments, flowable compositions 20 having a higher viscosity and/or a stickier composition may experience a greater pressure than less viscous and/or less sticky flowable compositions as the plunger 400 is pressed upward. The higher pressure build-up may cause the administering tool 500 to disengage from the body 100 before the plunger 400 has reached the end of the threads 304 of the drive screw 300. For example, when a flowable composition 20 having a viscosity and stickiness of creamy peanut butter is placed in the dispenser 10, the pressure build-up from the flowable composition 20 will force the administering tool 500 to disengage from the body 100 when the plunger 400 is still approximately 5-6 clicks from reaching the administering tool 500.

To alleviate this side effect, in certain embodiments, the drive screw 300 may be replaced with a drive screw 300A, as shown in FIG. 49. In these embodiments, the top 1-3 threads 304 have been mechanically fused to form a blocked section 318, which prevents the plunger 400 from traveling above this point on the drive screw 300A. As a result, the plunger 400 is unable to continue to press against the flowable composition 20, and the pressure does not build to the point that the administering tool 500 is removed from the body 100. This design leaves approximately 2 mL of residual flowable composition 20 between the plunger 400 and the administering tool 500 for the flowable compositions 20 having a higher viscosity and/or a stickier composition. However, this same design may be utilized with less viscous and/or less sticky flowable compositions 20 and there is minimal or no residual composition remaining between the plunger 400 and the administering tool 500.

Figure 25:
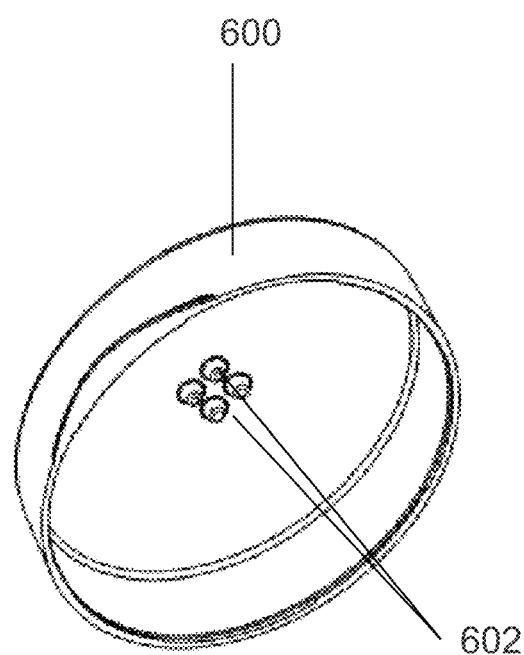
FIG. 25 is a bottom perspective view of a cap of the metering dispenser of FIG. 1.
Figure 26:
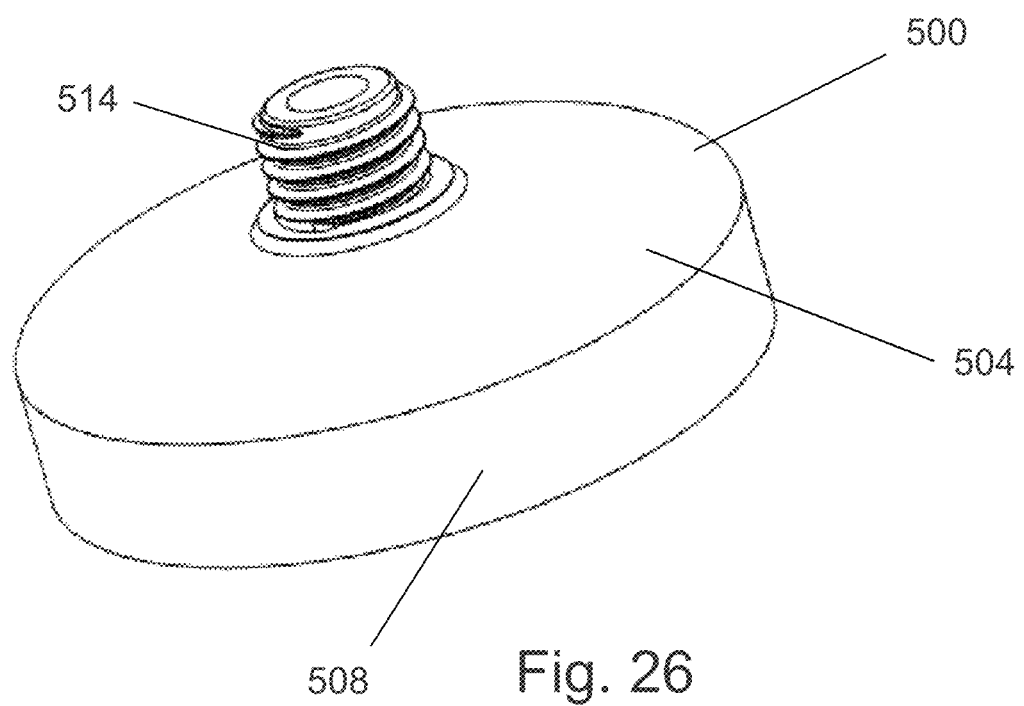
FIG. 26 is a perspective view of the administering tool of FIG. 20 with a threaded nozzle.
Figure 27:
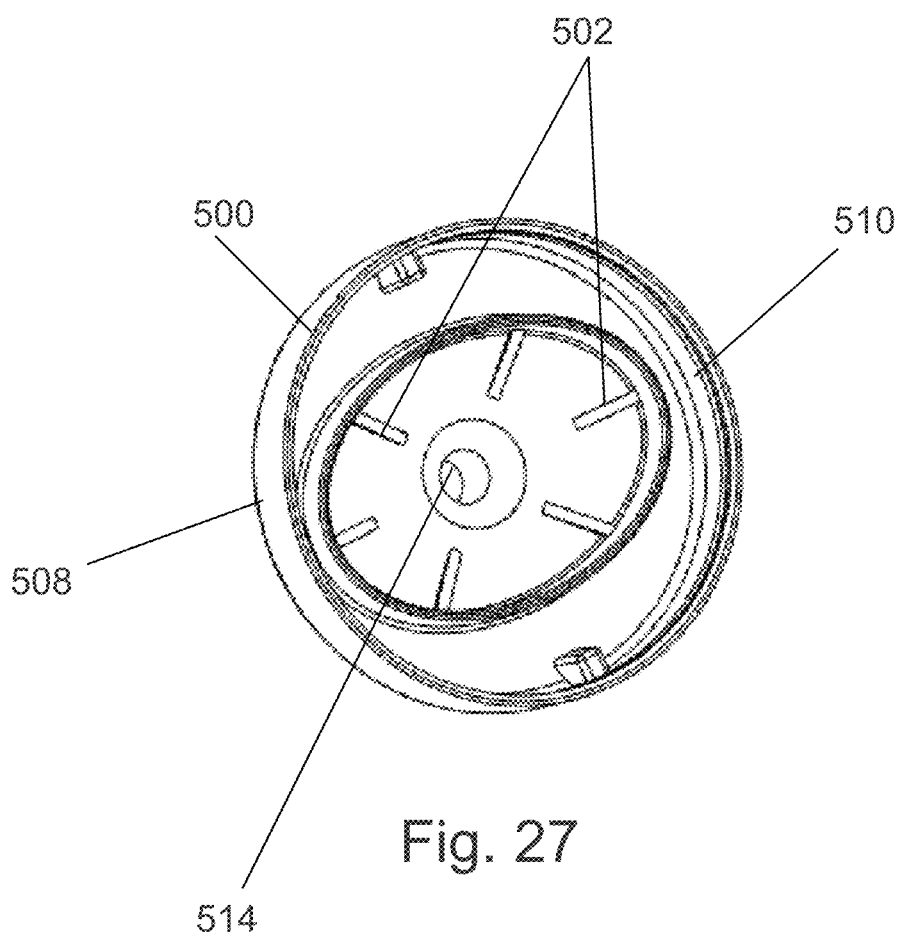
FIG. 27 is a bottom perspective view of the administering tool of FIG. 26.

In certain embodiments, as shown in FIG. 25, the cap 600 is sized to snugly fit over the administering tool 500 to prevent contamination of the pad and to reduce evaporation of the flowable composition 20.

Figure 28:
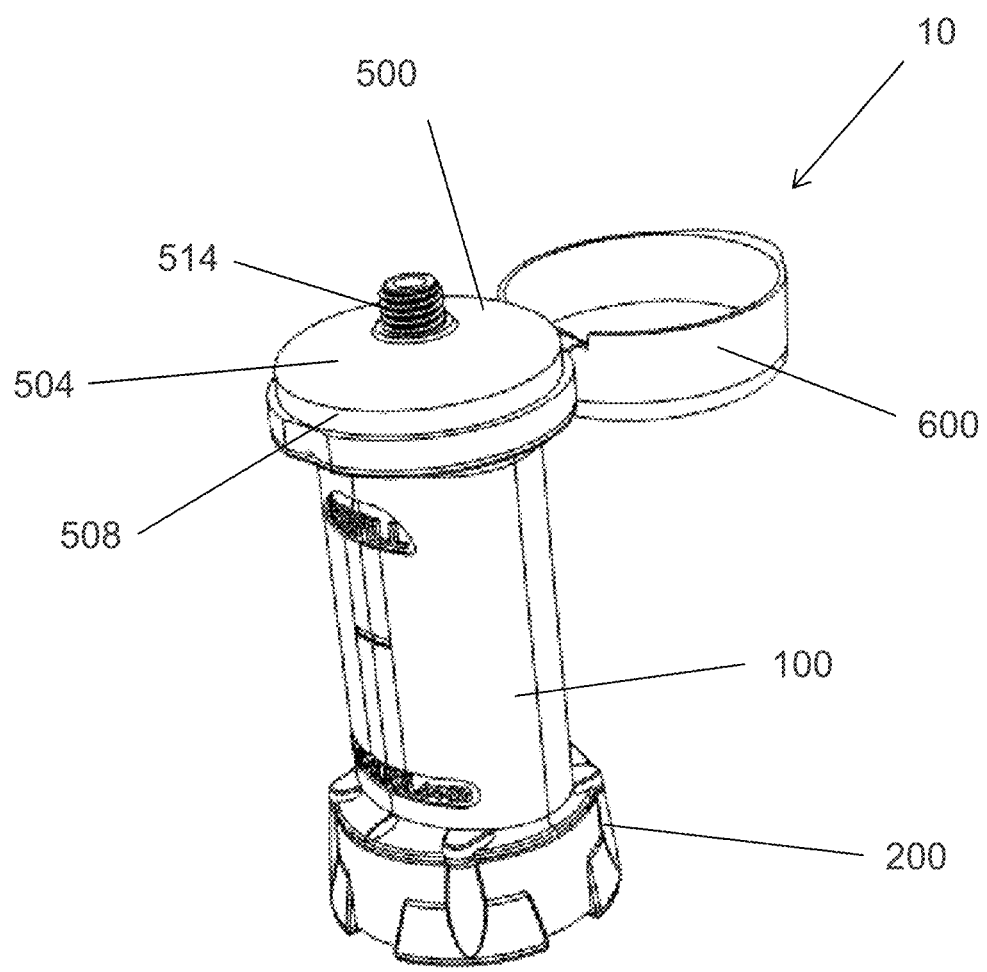
FIG. 28 is a perspective view of the metering dispenser of FIG. 1 with the administering tool of FIG. 26 and a flip-top cap in an open position, according to certain embodiments of the present invention.
Figure 29:
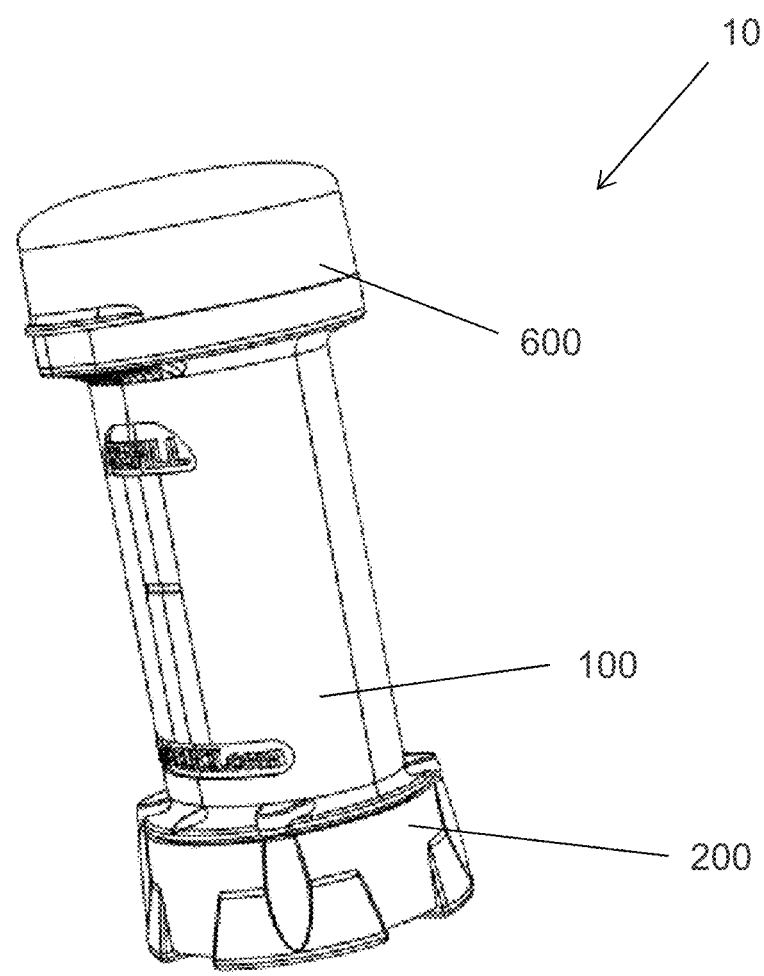
FIG. 29 is a perspective view of the metering dispenser of FIG. 1 with the administering tool of FIG. 26 and a flip-top cap in a closed position, according to certain embodiments of the present invention.

In additional embodiments, as best illustrated in FIGS. 26-29, the administering tool 500 may be configured to include a threaded nozzle 514, which may be used in place of the at least one hole 506 and/or may be an extension thereof. The nozzle 514 may be configured to couple to vaginal, rectal, and/or oral dispensing applicators. Such a design allows these applicators to be loaded with the flowable composition 20 in a much cleaner and precise manner. In these embodiments, the cap 600 may be configured as a flip-top design that snaps over the administering tool 500, as shown in FIGS. 28-29.

Figure 30:
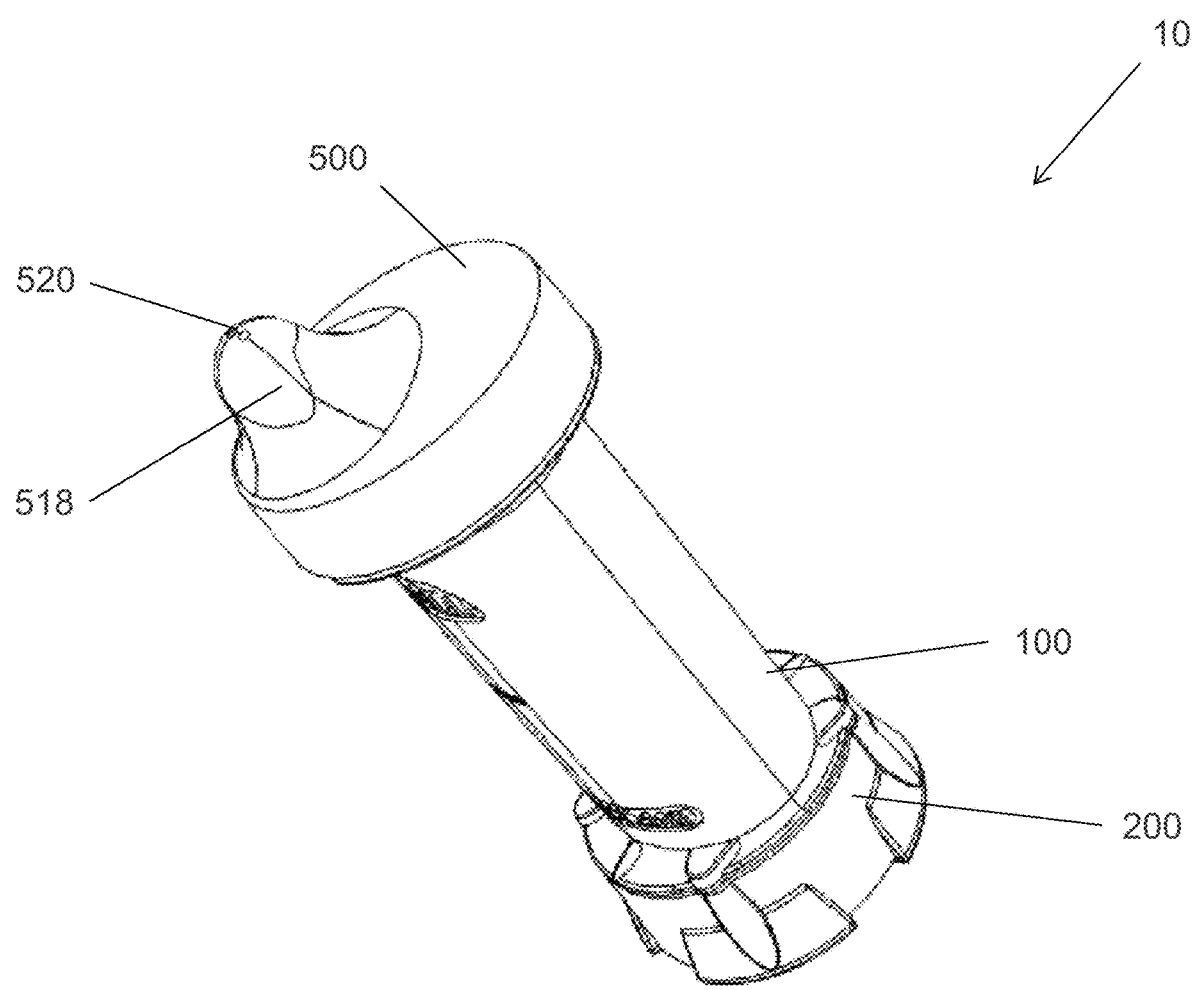
FIG. 30 is a perspective view of the metering dispenser of FIG. 1 with a spout incorporated into the administering tool, according to certain embodiments of the present invention.

In certain embodiments, such as those embodiments shown in FIG. 30, the administering tool 500 may include a spout 518 with holes 520 that is configured to allow a child or person to ingest the flowable composition 20 directly from the administering tool 500. These embodiments of the administering tool 500 may be useful in cases where the flowable composition 20 is a positive viscosity liquid that is orally ingested.

Figure 31:
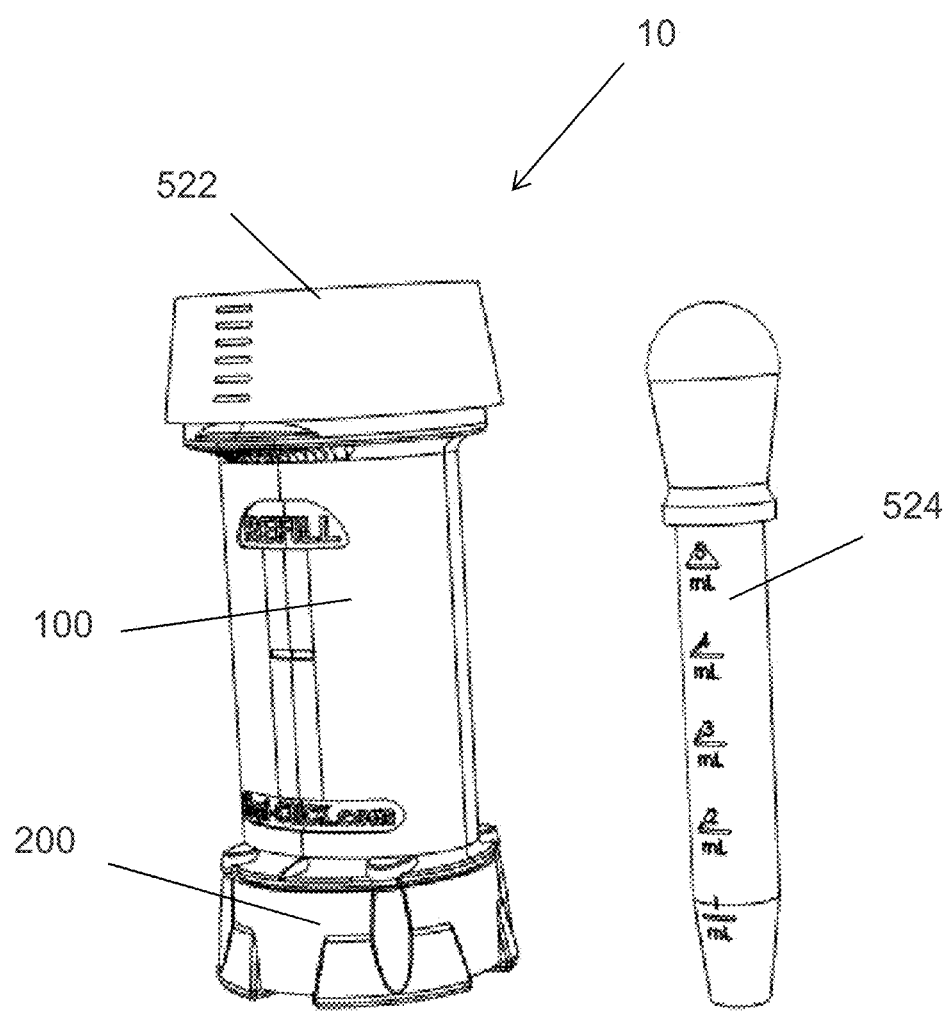
FIG. 31 is a perspective view of the metering dispenser of FIG. 1 with a collection device incorporated into the administering tool and a dropper, according to certain embodiments of the present invention.

In additional embodiments, such as those embodiments shown in FIG. 31, the administering tool 500 may include a cup or other collection device 522 that couples to the top of the administering tool 500 and collects the flowable composition 20 when it is dispensed. The flowable composition 20 collected in the collection device 522 may be ingested directly from the collection device 522 or may be transferred from the collection device 522 to a recipient via a dropper 524.

Once the dispenser 10 is assembled but prior to coupling of the administering tool 500, the chamber 110 is filled with the appropriate measured amount of flowable composition 20. The base 200 is turned so that the drive screw 300 turns and advances the plunger 400 and flowable composition 20 toward the first end 106 of the body 100. The administering tool 500 is then snapped onto the top of body 100. The base 200 is turned and the plunger 400 is advanced until there is essentially no air inside the chamber 110 between the flowable composition 20 and the administering tool 500. The cap 600 is placed on the administering tool 500 and the dispenser 10 is ready for use.

The user removes the cap 600 and turns the base 200 the appropriate amount of clicks (typically as directed on the instructions given to the user by the dispensing physician or pharmacy). As the base 200 is turned, the tabs 114 flex and move over the cam 208 as described above, and/or at least one protrusion 230 moves toward at least one projection 120. As the at least one tab 114 reaches the trailing edge of the low point 222 and/or the at least one protrusion 230 passes over the at least one projection 120, at least one audible sound or "click" is heard when the base 200 reaches a home or "click" position. Also, the user may sense a vibration when the base 200 reaches a home or "click" position.

With each click, a predetermined amount of flowable composition 20 is forced by the rising plunger 400 to be dispensed through the holes 506 and/or nozzle 514 of the administering tool 500. In the embodiments where the flowable composition 20 is an emulsion, cream, or other semi-solid composition, the dispensed flowable composition 20 may form a bead or pool over the central area of the top surface 504 of the administering tool 500. The user applies the flowable composition 20 to the skin by rubbing the administering tool 500 on the skin. The flowable composition 20 at least partially spreads out over the top surface 504 and is rubbed into the skin.

Figure 32:
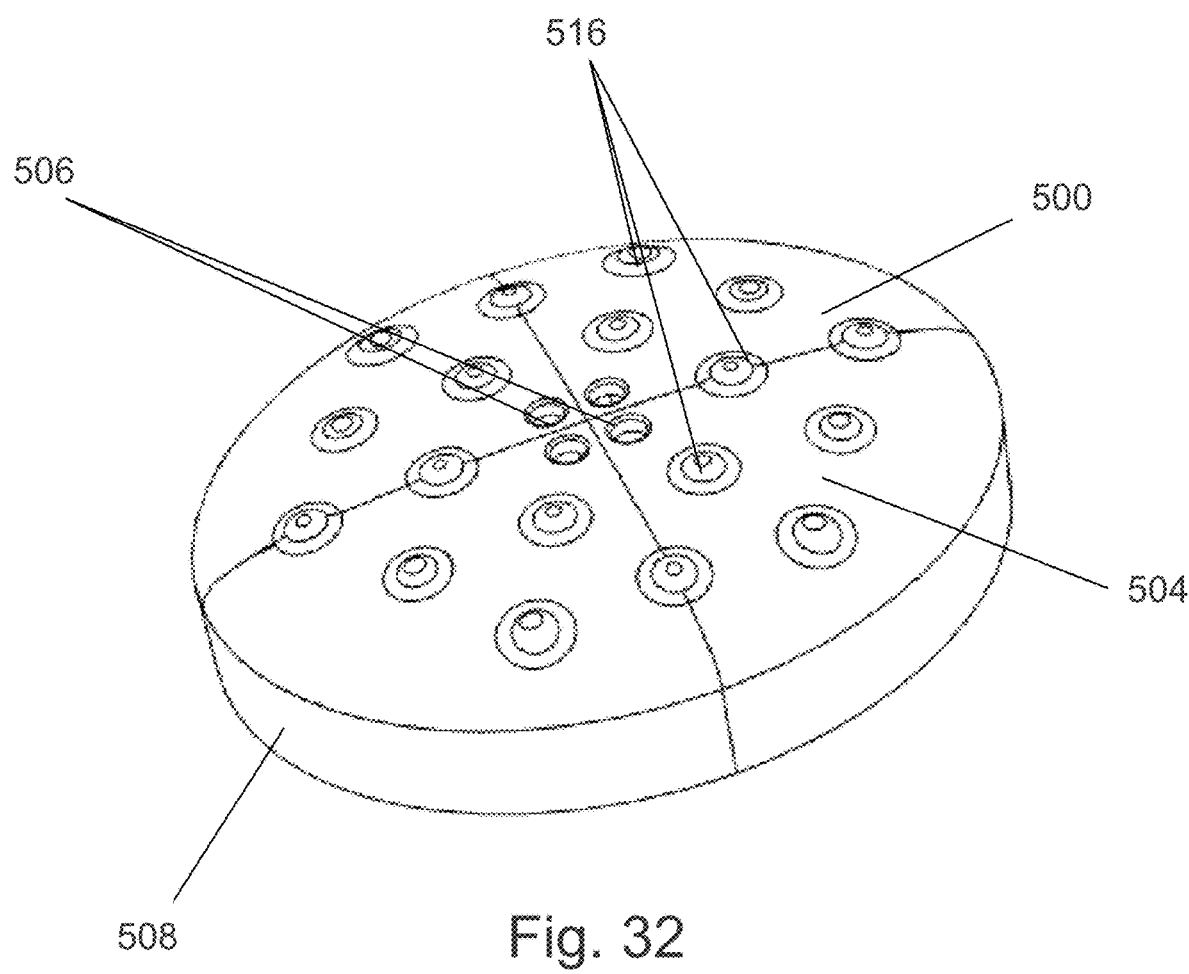
FIG. 32 is a perspective view of the administering tool of FIG. 20 with a plurality of protrusions.

In certain embodiments where the flowable composition 20 is applied to the skin, as illustrated in FIG. 32, the top surface 504 of the administering tool 500 may further include a plurality of protrusions 516, which may increase blood flow to the skin surface to accelerate absorption of the flowable composition 20. An increased rate of absorption may be beneficial in cases where patients do not rub the necessary 1-2 minutes as needed to ensure that the flowable composition 20 is dry and absorbed. The protrusions 516 may have any suitable shape include rounded, elliptical, or other suitable shapes.

The tactile and/or audible sound or click heard as the base 200 in turn provides feedback as to how much flowable composition 20 is dispensed. For example, the prescription might be for 1 cc of flowable composition 20 per dose to be applied to the skin. If each click is 0.25 cc, for example, then the prescription might instruct the user to turn the base 200 to hear four clicks so as to dispense 1 cc of flowable composition 20. The design of the present invention substantially prevents reverse rotation of the base 200 with respect to the body 100 so that flowable composition 20 is not inadvertently sucked back into the dispenser 10, which may reduce the effective dosage dispensed and may contaminate the flowable composition 20 in the chamber 110. The click also provides positive feedback when the right amount of flowable composition 20 has been dispensed per turn.

Optionally, as best illustrated in FIG. 25, the cap 600 may have downward projecting protrusions 602 which are receivable within the holes 506 of the administering tool 500. The protrusions 602 substantially seal the holes 506 when the cap 600 is in place, thereby reducing the risk of contamination of the flowable composition 20 and preventing clogging of the holes 506. Preferably, the cap 600 has a registering means to align with the administering tool 500 to make alignment of the protrusions 602 and the holes 506 easier.

In certain embodiments, the dispenser 10 of the present invention may optionally include a vibration mechanism whereby the dispenser 10 and, in particular, the administering tool 500 area vibrates when activated so as to improve transfer of the flowable composition 20 to the skin. The vibration mechanism may be one of several possible mechanisms known to those skilled in the art.

The dispenser of the present invention may also include an indicator mechanism either to show the approximate number of remaining doses or to show when the chamber 110 is near empty, both so that the user can have advance awareness that a refill may be needed.

Figure 33:
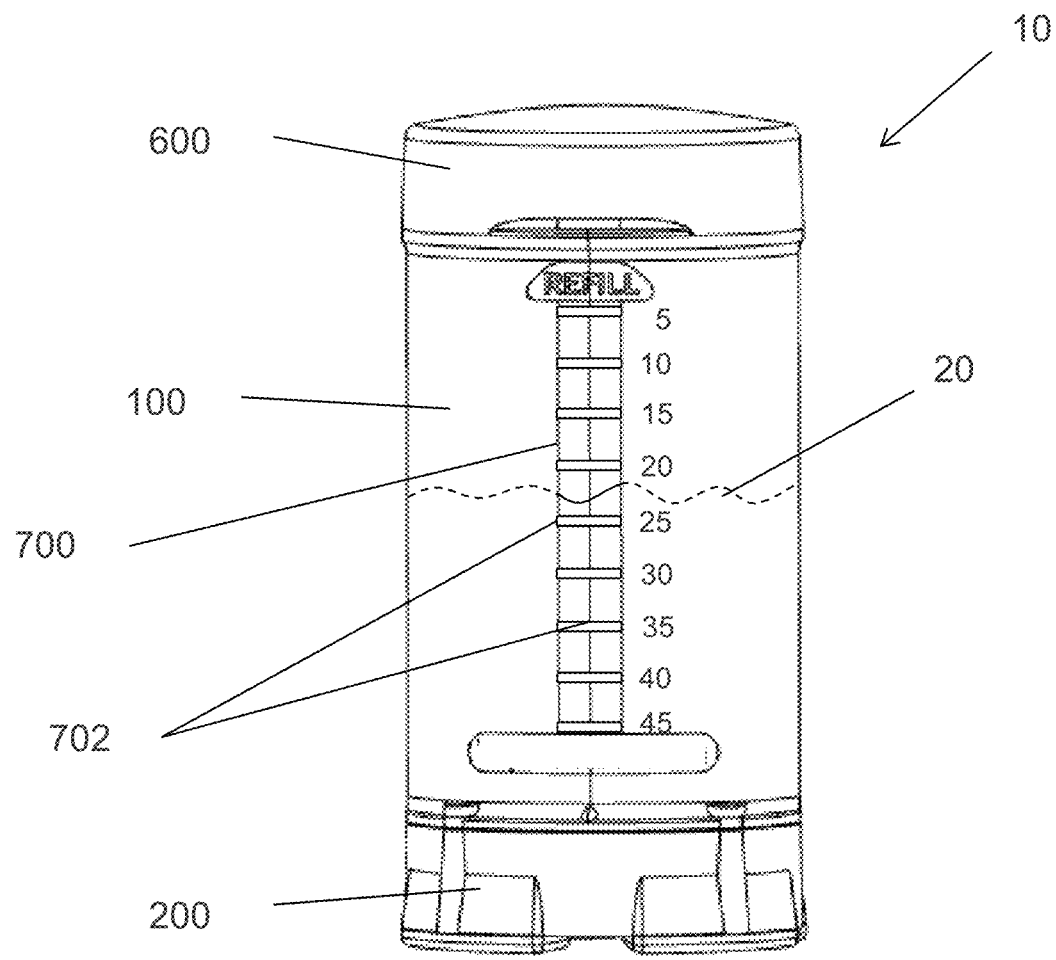
FIG. 33 is a perspective view of the metering dispenser of FIG. 1 with a ruler and marks along the body.

In certain embodiments of an indicator, shown in FIG. 33, a dispenser 10 may have a ruler 700 with set of marks 702 along the side of the body 100, with each mark being correlated to a particular quantity of flowable composition 20 remaining in the dispenser 10. In these embodiments, the body 100, or at least a portion thereof (such as an elongated window extending from near the first end 106 to near the second end 108) is preferably clear or translucent.

Figure 34:
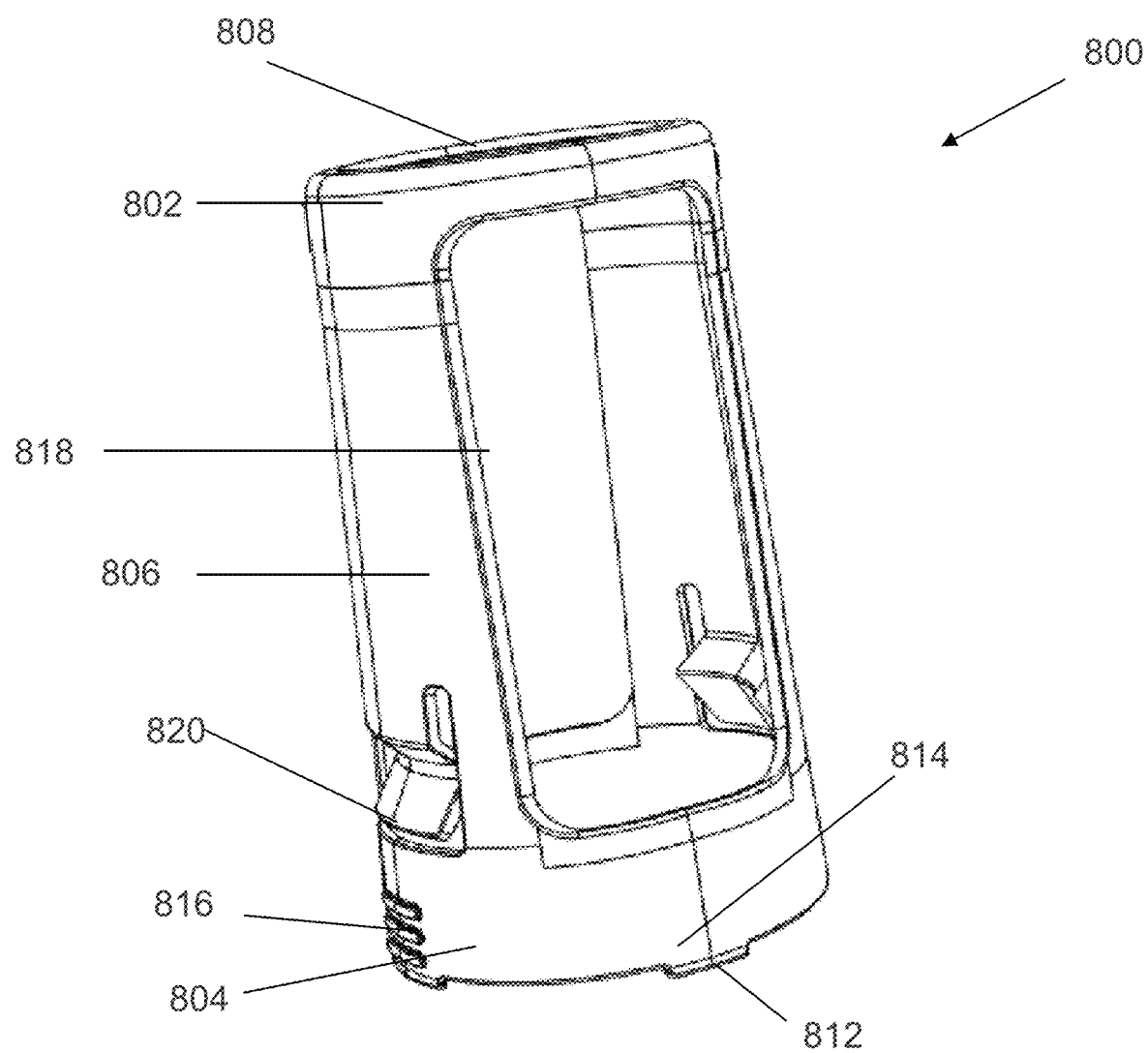
FIG. 34 is a perspective view of a child resistant receptacle, according to certain embodiments of the present invention, for use with the metering dispenser of FIG. 1.
Figure 35:
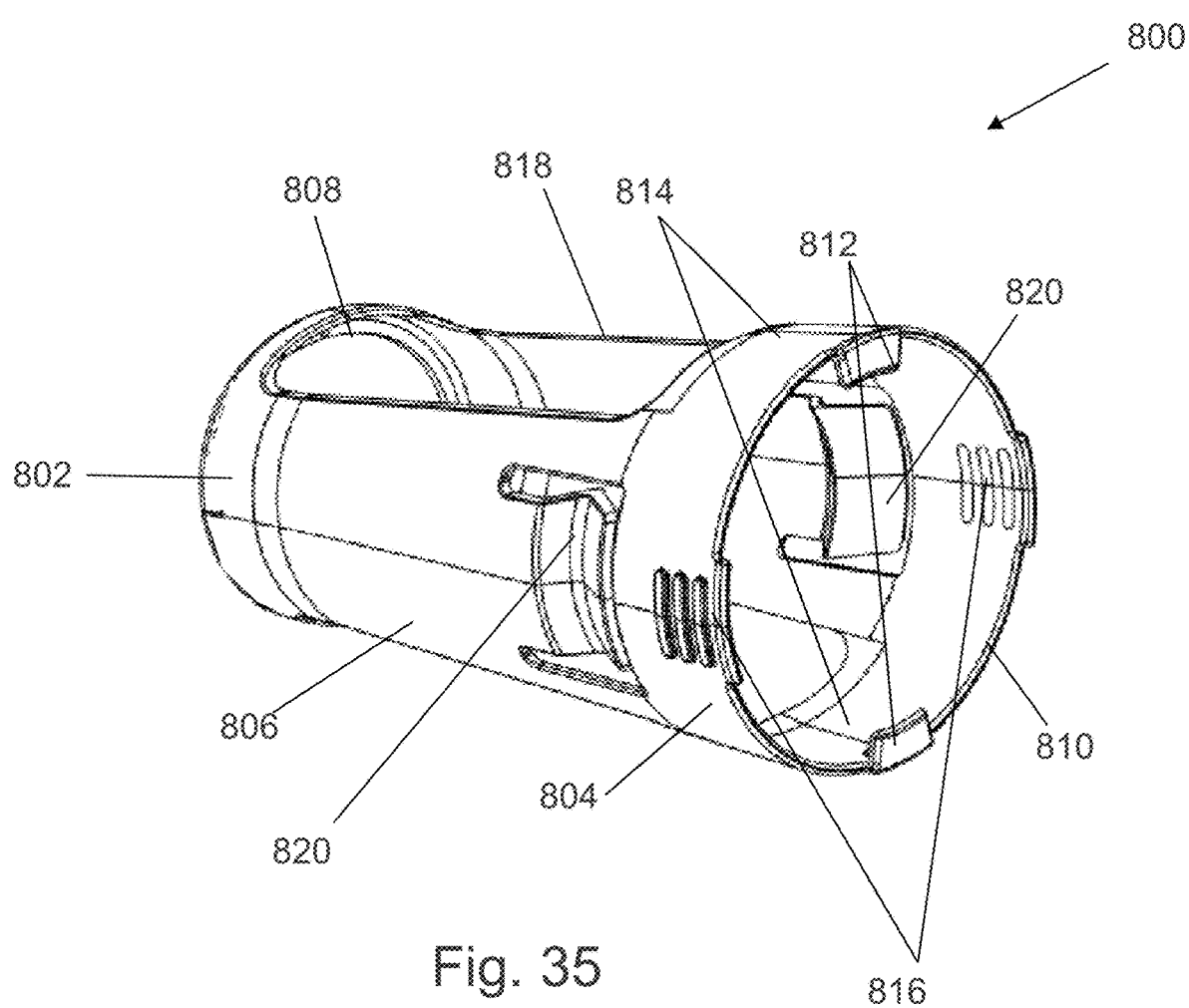
FIG. 35 is a side perspective view of the child resistant receptacle of FIG. 34.
Figure 36:
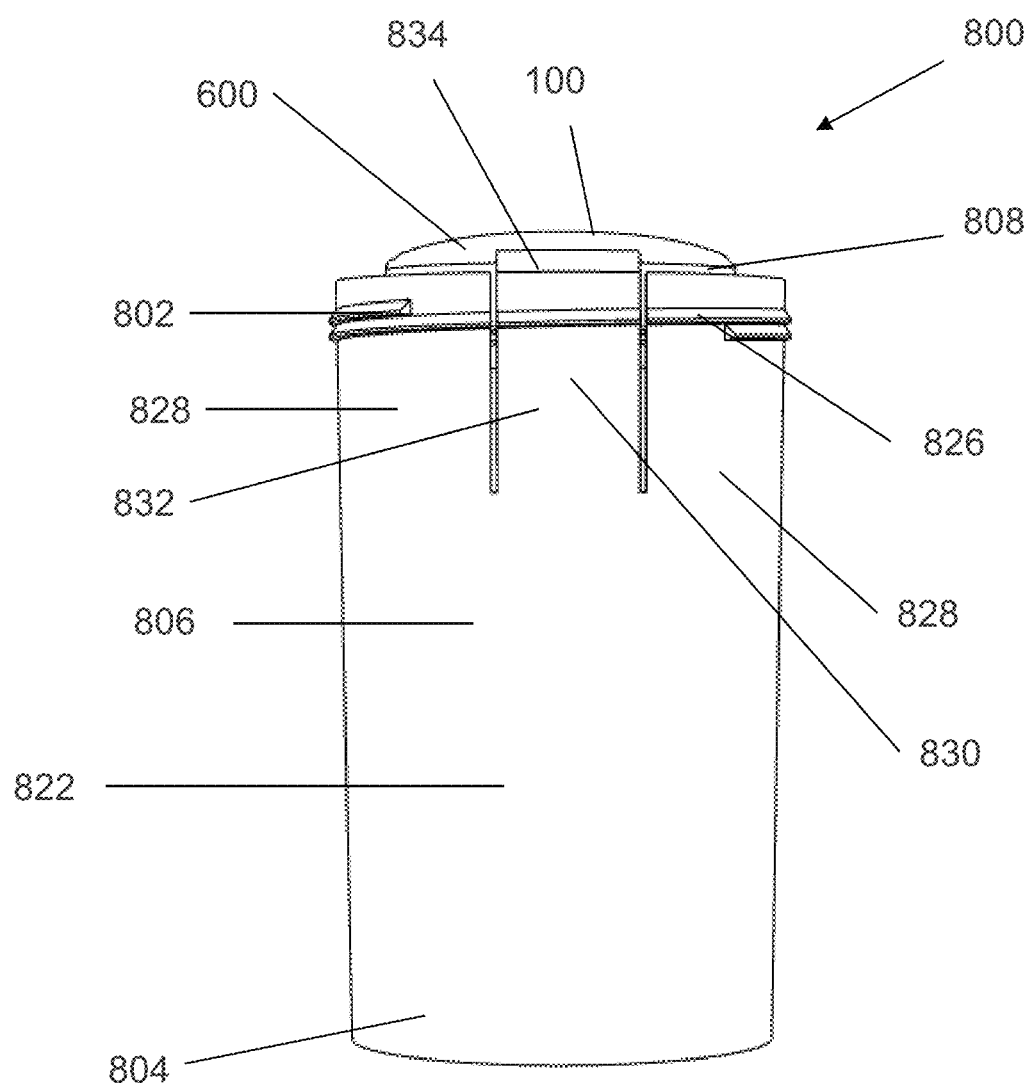
FIG. 36 is a side view of a child resistant receptacle with a cap removed, according to certain embodiments of the present invention, for use with the metering dispenser of FIG. 1.
Figure 37:
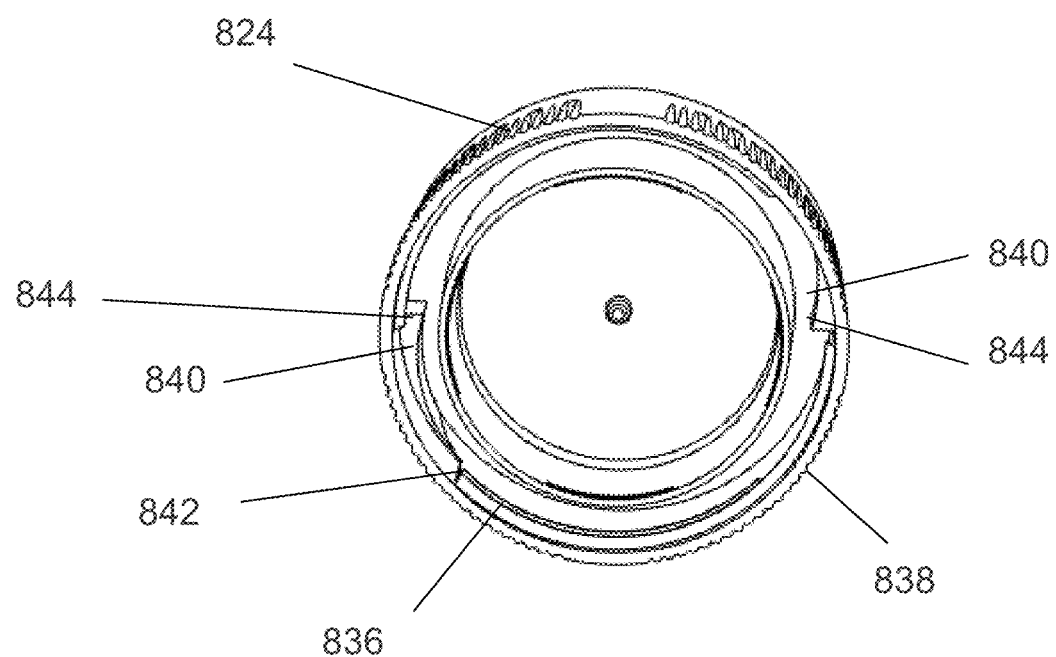
FIG. 37 is an internal perspective view of a cap for use with the child resistant receptacle of FIG. 36.
Figure 38:
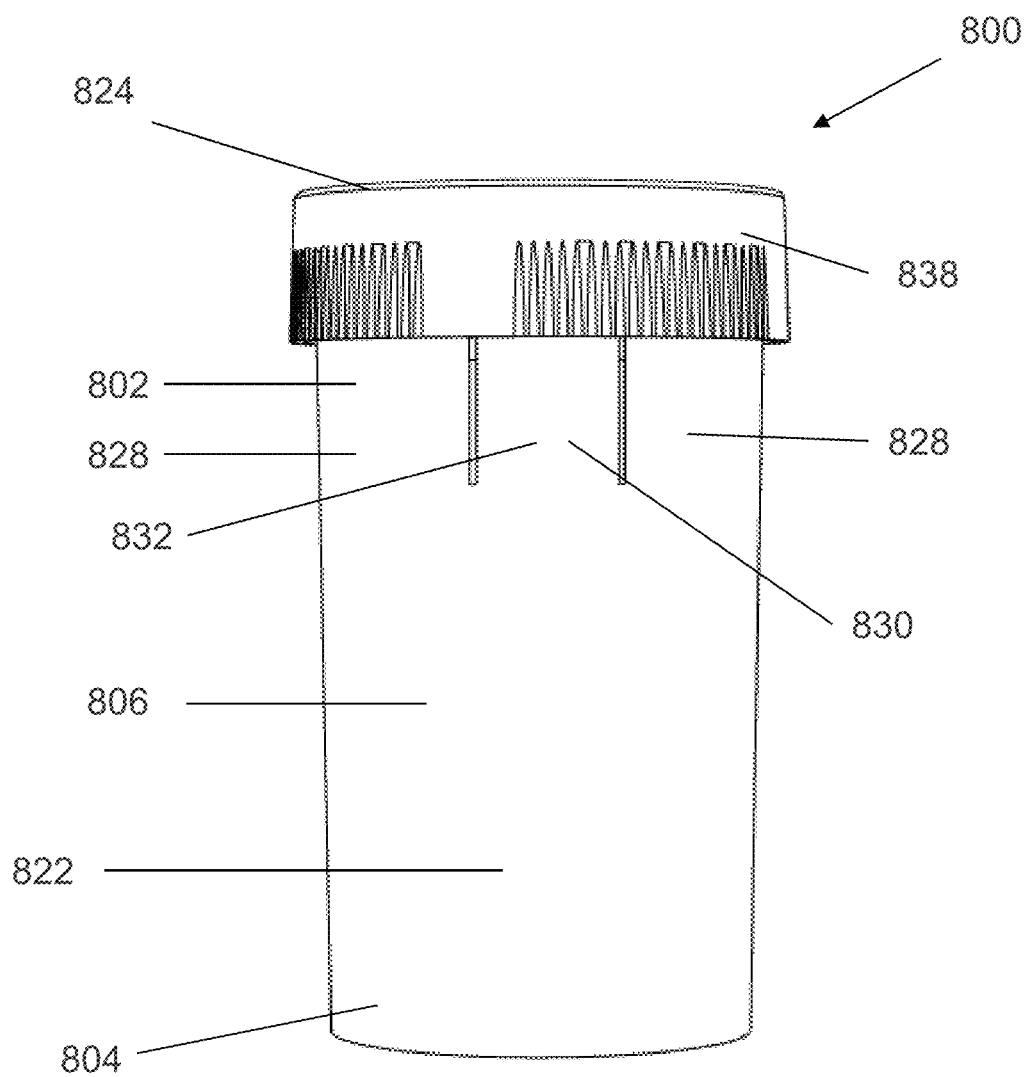
FIG. 38 is a side view of the child resistant receptacle of FIG. 36 with the cap installed.
Figure 39:
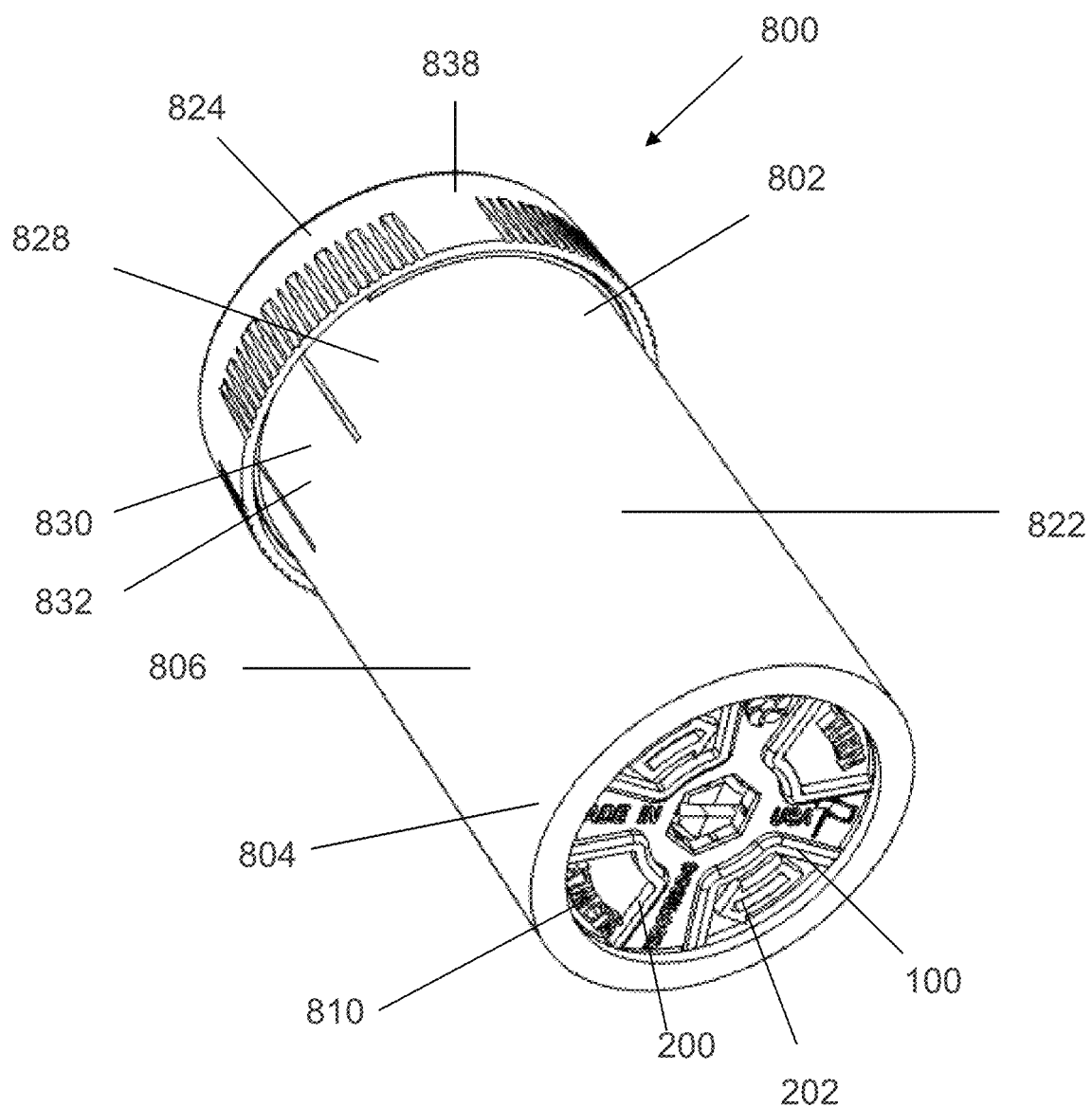
FIG. 39 is a perspective view of the child resistant receptacle of FIG. 36 with the cap installed.
Figure 40:
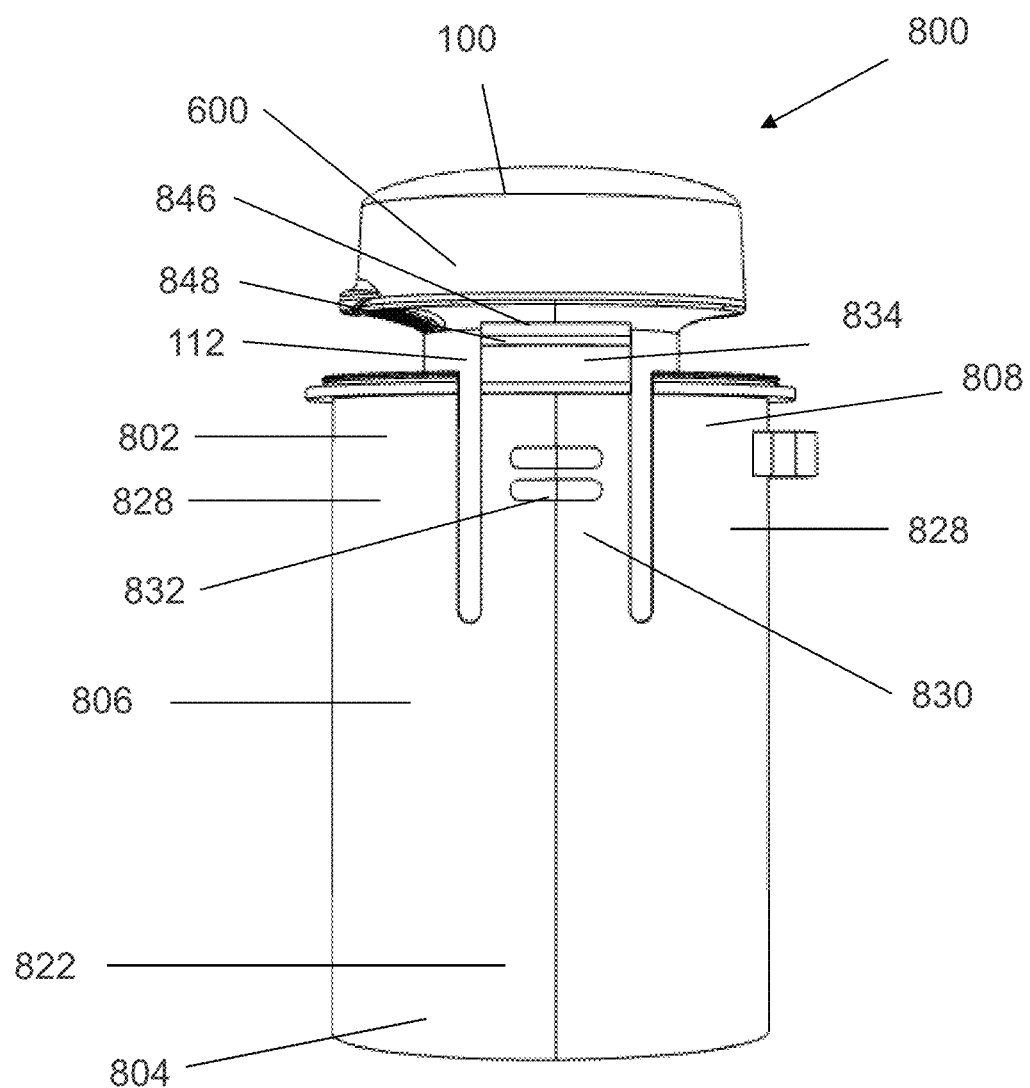
FIG. 40 is a side view of a child resistant receptacle with a cap removed, according to certain embodiments of the present invention, for use with the metering dispenser of FIG. 1.
Figure 41:
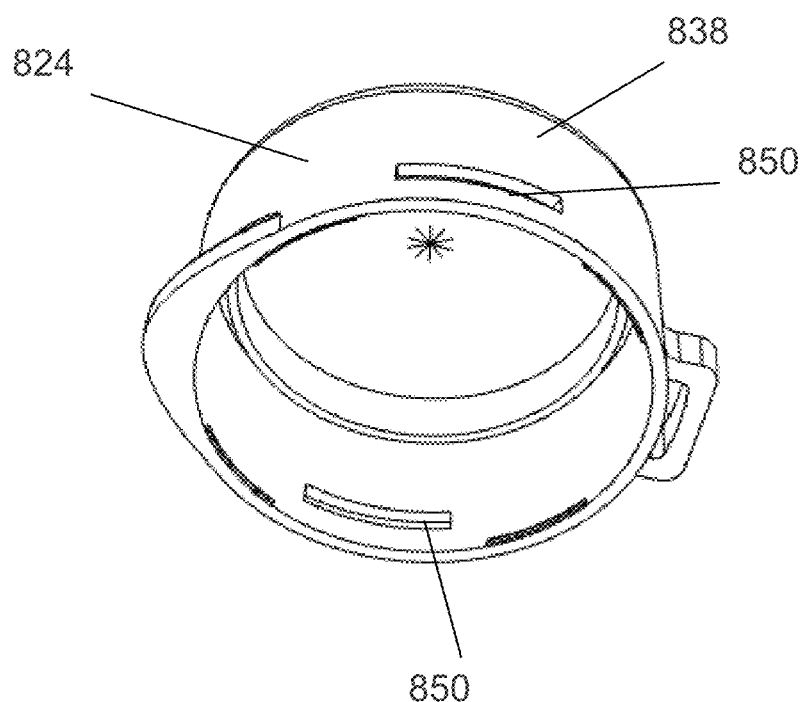
FIG. 41 is an internal perspective view of a cap for use with the child resistant receptacle of FIG. 40.
Figure 42:
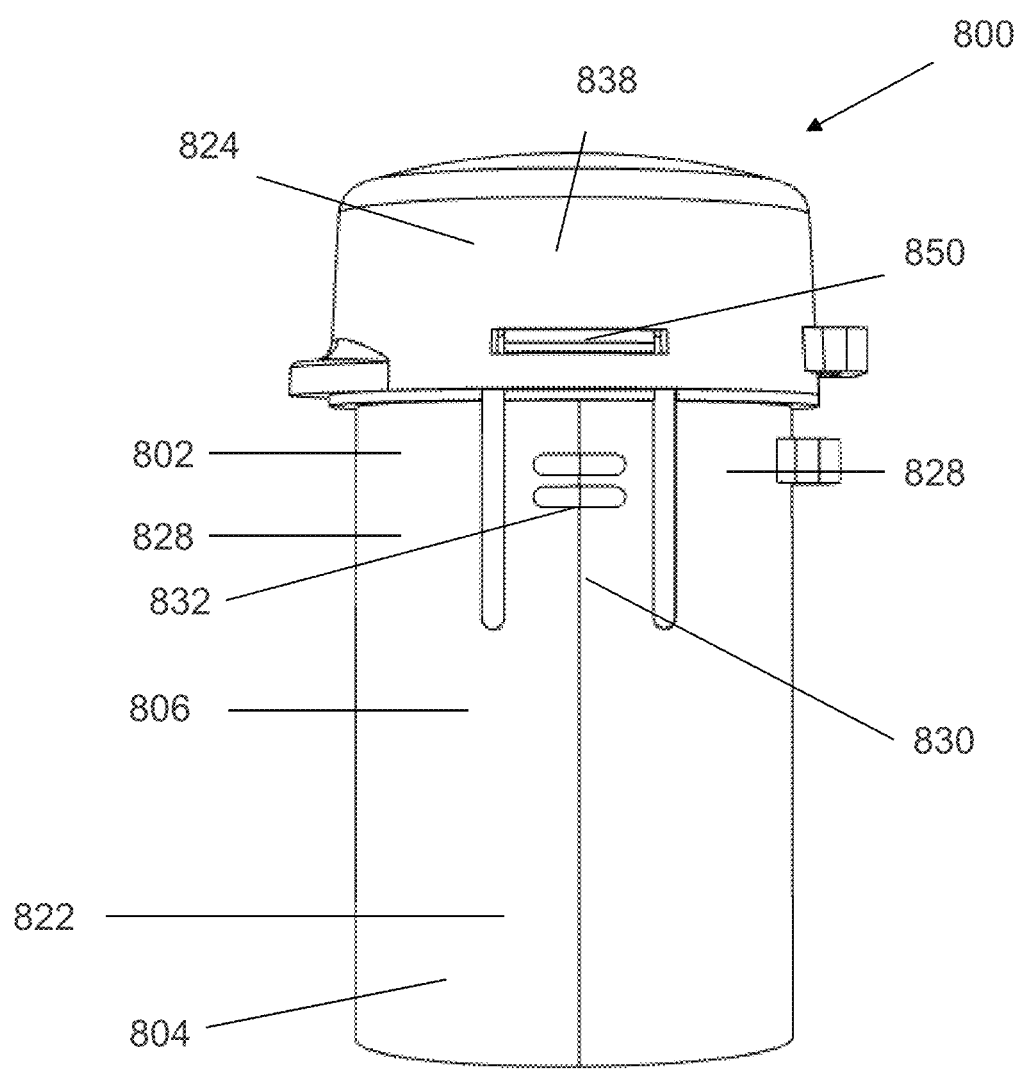
FIG. 42 is a side view of the child resistant receptacle of FIG. 40 with the cap installed.
Figure 43:
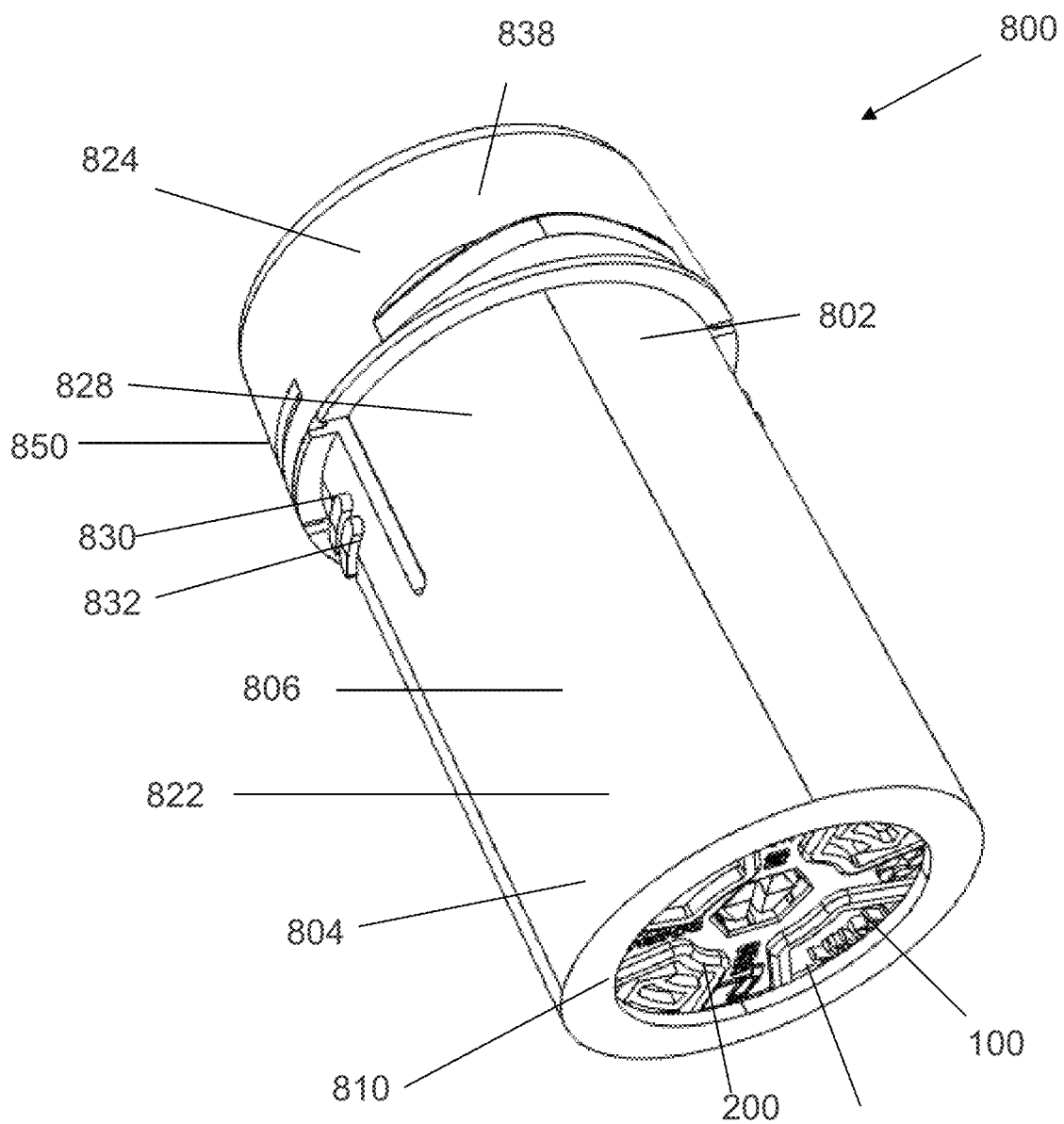
FIG. 43 is a perspective view of the child resistant receptacle of FIG. 40 with the cap installed.
Figure 44:
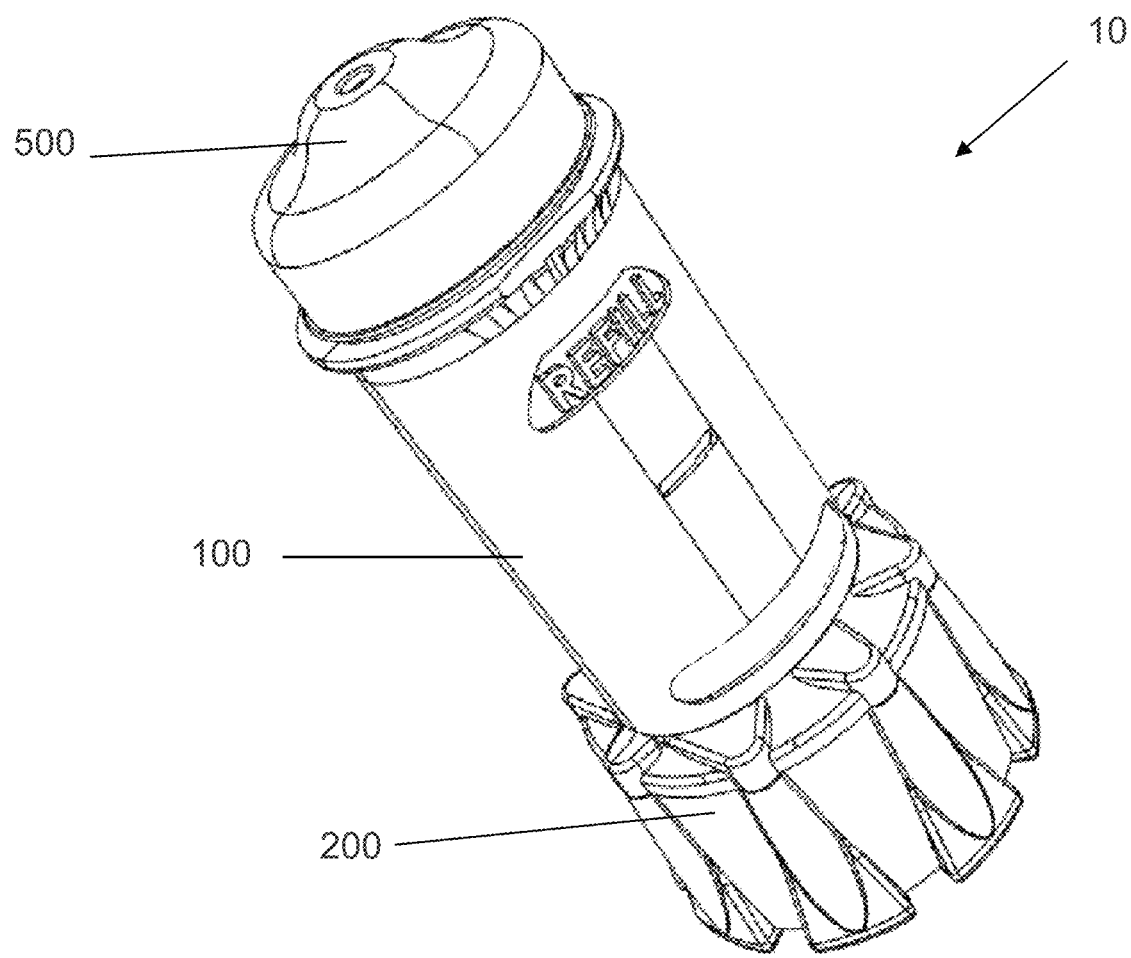
FIG. 44 is a perspective view of a metering dispenser, according to certain embodiments of the present invention.
Figure 45:
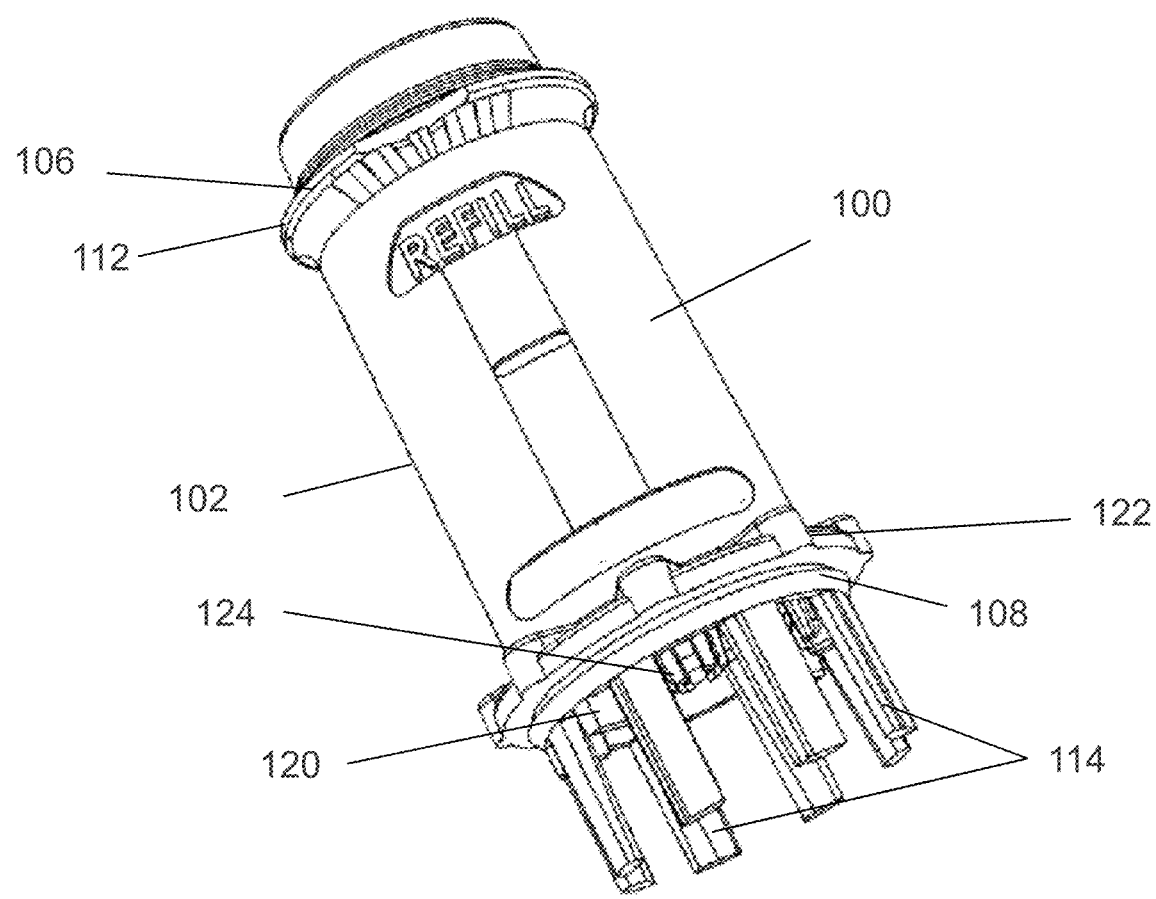
FIG. 45 is a perspective view of a body of the metering dispenser of FIG. 44.

In the present invention, a child resistant receptacle 800 may be incorporated with the dispenser 10 to prevent children from accessing the flowable composition 20. In certain embodiments, as best illustrated in FIGS. 34-35, the child resistant receptacle 800 comprises an upper end 802, a lower end 804, and a sidewall 806 that connects the two ends 802, 804. The sidewall 806 is configured to substantially surround the outer wall 102 of the body 100, the sidewall 204 of the base 200, and the sidewall 508 of the administering tool 500 (which may be covered by the cap 600).

In the embodiments shown in FIGS. 34-35, when the child resistant receptacle 800 is positioned over the dispenser 10, the sidewall 806 is longitudinally shaped so that the upper end 802 is positioned proximate the top surface 504 of the administering tool 500 (which may be covered by the cap 600), wherein the upper end 802 may have a cross-sectional shape that snugly fits over the top surface 504 of the administering tool 500 and/or the cap 600. In certain embodiments, the upper end 802 may comprise an opening 808 that is smaller than the cross-sectional shape of the administering tool 500 and/or the cap 600 to prevent the dispenser 10 from sliding through the opening 808, while at the same time providing an access point to press the dispenser 10 down through the lower end 804 when the lower end 804 is deformed, which is discussed in more detail below. In certain embodiments, the opening 808 may be configured to accommodate the administering tool 500 that includes the nozzle 514. The opening 808 may also save on material costs to manufacture the child resistant receptacle 800.

When the child resistant receptacle 800 is positioned over the dispenser 10, the sidewall 806 is also longitudinally shaped so that the lower end 804 is positioned proximate the bottom portion 202 of the base 200. The lower end 804 may have an oval or parabolic cross-sectional shape, wherein the narrower dimension of the lower end 804 is configured to fit snugly against portions of the sidewall 204 of the base 200.

The lower end 804 may further comprise an opening 810 that comprises substantially the same dimensions as the lower end 804.

To secure the child resistant receptacle 800 to the dispenser 10, a pair of lips 812 may be positioned on opposing sides 814 of the opening 810 along the narrower dimension of the opening 810. Because the narrower dimension of the opening 810 is configured to fit snugly against portions of the sidewall 204 of the base 200, the lips 812 therefore extend below the bottom portion 202 of the base 200, thereby preventing the dispenser 10 from passing through the opening 810.

The child resistant receptacle 800 may be formed of materials including but not limited to polymer, plastic, composite, or other formable or moldable material, which provide some elasticity to allow at least the lower end 804 to be slightly deformed when an external pressure is applied to opposing sides 816 of the opening 810 along the wider dimension of the opening 810. When deformed, the opposing sides 816 are pressed against portions of the sidewall 204 of the base 200, which in turn causes the opposing sides 814 of the opening 810 to move away from the sidewall 204 of the base 200, thus also causing the pair of lips 812 to also move away from the bottom portion 202 of the base 200. In this deformed shape, the dispenser 10 may then slide out of the opening 810, which is also shaped to allow the body 100, the administering tool 500, and/or the cap 600 to slide therethrough.

To reinsert the dispenser 10 into the child resistant receptacle 800, an external pressure is again applied to opposing sides 816 of the opening 810 along the wider dimension of the opening 810 to deform the shape of the opening 810 until the opposing sides 814 of the opening 810 have been sufficiently spread apart to move the pair of lips 812 out of the way so that the dispenser 10 may be inserted through the opening 810. The external pressure is applied to opposing sides 816 to maintain the opening 810 in the deformed position until the dispenser 10 has been inserted completely inside the child resistant receptacle 800 and the bottom portion 202 is above the lips 812. The external pressure is then released, and the opening 810 returns to the original shape, which causes the opposing sides 814 of the opening 810 to move back toward and contact portions of the sidewall 204 of the base 200, thus also causing the pair of lips 812 to be positioned below the bottom portion 202 of the base 200.

In certain embodiments, portions of the sidewall 806 may include apertures 818, which may provide access points to press the dispenser 10 down through the lower end 804 when the lower end 804 is deformed, as described above. The apertures 818 may also save on material costs to manufacture the child resistant receptacle 800.

The sidewall 806 may also comprise a pair of grippers 820 located on opposing sides of the sidewall 806. The grippers 820 may be included to provide some additional force against the body 100, especially where the body 100 may comprise an oval or elliptical shape, and the grippers 820 are configured to be located proximate the wider dimension of the body 100. In other embodiments, the grippers 820 may be located proximate the narrower dimension of the body 100. The grippers 820 are also configured with an elastic design that allow the grippers 820 to bend out of the way during insertion/removal of the dispenser 10 as needed, but return to their relaxed position once the dispenser 10 has been inserted or removed.

In further embodiments, as best illustrated in FIGS. 36-39, the child resistant receptacle 800 comprises a lower portion 822 and a cap 824. The lower portion 822 comprises the upper end 802 and the lower end 804, and the sidewall 806 that connects the two ends 802, 804. The sidewall 806 is configured to substantially surround the outer wall 102 of the body 100, the sidewall 204 of the base 200, and the sidewall 508 of the administering tool 500 (which may be covered by the cap 600).

In the embodiments shown in FIGS. 36-39, when the dispenser 10 is positioned within the lower portion 822, the sidewall 806 is longitudinally shaped so that the upper end 802 is positioned proximate the top surface 504 of the administering tool 500 (which may be covered by the cap 600). The lower end 804 may have a cross-sectional shape that snugly fits over the bottom portion 202 of the base 200. In certain embodiments, the lower end 804 may comprise the opening 810, which may be smaller than the cross-sectional shape of the bottom portion 202 of the base 200 to prevent the dispenser 10 from sliding through the opening 810, while at the same time providing an access point to press the dispenser 10 up through the upper end 802 when the cap 824 is removed, which is discussed in more detail below. The opening 810 may also save on material costs to manufacture the child resistant receptacle 800.

The upper end 802 may further comprise the opening 808, which may be larger than the largest cross-sectional shape of the dispenser 10 (or at least the largest cross-section shape of the dispenser 10 that is configured to fit inside the lower portion 822) to allow the dispenser 10 to be inserted into the lower portion 822 through the opening 808.

To secure the child resistant receptacle 800 to the dispenser 10, the cap 824 is secured to the upper end 802 of the lower portion 822. The upper end 802 of the lower portion 822 comprises external helical threads 826 that extend around the circumference of the upper end 802. The upper end 802 is also circumferentially segmented such that it includes a pair of diametrically opposed rigid sections 828 and a pair of diametrically opposed identical levers 830 positioned between the rigid sections 828. The levers 830 are configured to bend inwardly when pressure is applied to an outer surface 832 of the levers 830. In certain embodiments, the levers 830 comprise a locking tab 834 that extends from a top surface of the lever 830.

The cap 824 comprises internal helical threads 836 that extend around the internal circumference of a sidewall 838 of the cap 824. The sidewall 838 also includes a pair of diametrically opposed locking members 840 positioned above the internal helical threads 836. Each locking member 840 comprises a leading edge 842 and a trailing edge 844. The leading edge 842 has a somewhat gradually inclining sloped shape that facilitates movement of the locking tab 834 in the direction of the leading edge 842, and wherein the trailing edge 844 has a squared or otherwise steep slope that resists movement of the locking tab 834 in the direction of the trailing edge 844.

The child resistant receptacle 800 may be formed of materials including but not limited to polymer, plastic, composite, or other formable or moldable material. In some embodiments, the materials for the lower portion 822 may provide some elasticity to allow at least the lever 830 to be slightly deformed when an external pressure is applied and/or that have the resiliency to form a living hinge between the lever 830 and the sidewall 806.

To attach the child resistant receptacle 800 to the dispenser 10, the dispenser 10 is inserted through the opening 808 in the upper end 802 of the lower portion 822. The cap 824 is then positioned over the upper end 802 and turned so that the complementary helical threads 826, 836 engage with one another. As the cap 824 is turned, the locking tabs 834 are guided over the locking members 840 by the leading edge 842, wherein the tapered design gradually presses the levers 830 inward as the cap 824 is turned. Once the lever 830 has cleared the trailing edge 844 of the locking member 840, the lever 830 snaps back to its original position. The shape of the trailing edge 844 engages a side of the locking tab 834 to prevent the cap 824 from turning in the opposite direction.

To remove the dispenser 10 from the child resistant receptacle 800, an external pressure is applied to the levers 830, which presses the levers 830 inward so that they are no longer engaged by the trailing edges 844 of the locking members 840. The cap 824 can then be turned in the opposite direction, thus disengaging the complementary helical threads 826, 836 from one another. The cap 824 can then be removed so that the dispenser 10 can be removed through the opening 808 in the lower portion 822.

In still further embodiments, as best illustrated in FIGS. 40-43, the child resistant receptacle 800 again comprises a lower portion 822 and a cap 824. The lower portion 822 comprises the upper end 802 and the lower end 804, and the sidewall 806 that connects the two ends 802, 804. The sidewall 806 is configured to substantially surround the outer wall 102 of the body 100, the sidewall 204 of the base 200. In some embodiments, the sidewall 806 may also be configured to substantially surround the sidewall 508 of the administering tool 500 (which may be covered by the cap 600).

In the embodiments shown in FIGS. 40-43, when the dispenser 10 is positioned within the lower portion 822, the sidewall 806 is longitudinally shaped so that the upper end 802 is positioned proximate the external upper rim 112.

The lower end 804 may have a cross-sectional shape that snugly fits over the bottom portion 202 of the base 200. In certain embodiments, the lower end 804 may comprise the opening 810, which may be smaller than the cross-sectional shape of the bottom portion 202 of the base 200 to prevent the dispenser 10 from sliding through the opening 810, while at the same time providing an access point to press the dispenser 10 up through the upper end 802 when the cap 824 is removed, which is discussed in more detail below. The opening 810 may also save on material costs to manufacture the child resistant receptacle 800.

The upper end 802 may further comprise the opening 808, which may be larger than the largest cross-sectional shape of the dispenser 10 (or at least the largest cross-section shape of the dispenser 10 that is configured to fit inside the lower portion 822) to allow the dispenser 10 to be inserted into the lower portion 822 through the opening 808.

To secure the child resistant receptacle 800 to the dispenser 10, the cap 824 is secured to the upper end 802 of the lower portion 822. The upper end 802 of the lower portion 822 is circumferentially segmented such that it includes a pair of diametrically opposed rigid sections 828 and a pair of diametrically opposed identical levers 830 positioned between the rigid sections 828. The levers 830 are configured to bend inwardly when pressure is applied to an outer surface 832 of the levers 830. In certain embodiments, the levers 830 comprise a locking tab 834 that extends from a top surface of the lever 830. Each locking tab 834 may comprise a leading edge 846 and a trailing edge 848. The leading edge 846 has a somewhat gradually inclining sloped shape that is configured to allow the cap 824 to slide down over the locking tabs 834, and wherein the trailing edge 848 has a squared or otherwise steep slope that resists movement of the cap 824 in the direction of the trailing edge 848.

The cap 824 comprises a pair of diametrically opposed identical slots 850 that are shaped to receive the portion of the locking tab 834 that extends between the leading edge 846 and the trailing edge 848.

The child resistant receptacle 800 may be formed of materials including but not limited to polymer, plastic, composite, or other formable or moldable material. In some embodiments, the materials for the lower portion 822 may provide some elasticity to allow at least the lever 830 to be slightly deformed when an external pressure is applied and/or that have the resiliency to form a living hinge between the lever 830 and the sidewall 806.

To attach the child resistant receptacle 800 to the dispenser 10, the dispenser 10 is inserted through the opening 808 in the upper end 802 of the lower portion 822. The cap 824 is then positioned over the upper end 802 and pressed down so that the edge of the cap 824 gradually presses the locking tabs 834 inward as the cap 824 passes over the locking tabs 834. As the cap 824 continues to travel down over the locking tabs 834, the locking tabs 834 also travel along the sidewall 838 of the cap 824 until reaching the slots 850. Once the trailing edge 848 of the locking tab 834 has cleared the sidewall 838 of the cap 824 and is positioned in the slot 850, the lever 830 snaps back to its original position. The shape of the trailing edge 848 engages a side of the slot 850 to prevent the cap 824 from being removed from the lower portion 822.

To remove the dispenser 10 from the child resistant receptacle 800, an external pressure is applied to the levers 830, which presses the levers 830 inward so that they are no longer engaged by the slots 850. The cap 824 can then be removed so that the dispenser 10 can be removed through the opening 808 in the lower portion 822.

Different arrangements of the components depicted in the drawings or described above, as well as components and steps not shown or described are possible. Similarly, some features and sub-combinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A metering dispenser comprising:
 a body comprising:
  a first end;
  a second end opposite from the first end;
  a chamber between the first end and the second end;
  a plurality of tabs at the second end extending away from the body; and
  a plurality of projections at the second end extending away from the body,
   wherein a height of the plurality of tabs is less than a height of the plurality of projections; and
 a drive screw comprising an elongated shaft defining an end of the drive screw and extending into the chamber, and wherein the elongated shaft comprises:
  a first portion within the chamber and having at least one external thread; and
  a second portion within the chamber between the first portion and the end of the drive screw, wherein the second portion is unthreaded.

2. The metering dispenser of claim 1, further comprising a base coupled to the body, a plunger that is movable within the chamber, and an administering tool engaged with the first end of the body.

3. The metering dispenser of claim 1, further comprising a plunger positioned within the chamber and coupled to the elongated shaft of the drive screw such that the plunger is movable along the elongated shaft through the chamber when the drive screw is rotated.

4. The metering dispenser of claim 1, wherein the first end of the body defines a chamber opening providing access to the chamber, wherein the second end of the body comprises an end wall that at least partially defines the chamber of the body, and wherein the plurality of projections and the plurality of tabs extend from the end wall outside of the chamber.

5. The metering dispenser of claim 4 wherein the end wall of the second end defines an aperture, wherein the plurality of tabs and the plurality of projections are arranged around the aperture, and wherein the drive screw extends through the aperture.

6. The metering dispenser of claim 1, further comprising a base rotationally coupled to the second end of the body, wherein the plurality of projections are configured to produce a first audible sound based on engagement between the plurality of projections and the base when the base is rotated, and wherein the plurality of tabs are configured to produce a second audible sound based on engagement between the plurality of tabs and the base when the base is rotated.

7. The metering dispenser of claim 6, wherein the end of the drive screw is a first end, wherein the drive screw further comprises a cog defining a second end of the drive screw, and wherein the base is coupled to the cog of the drive screw.

8. A metering dispenser comprising a body, the body comprising:
 a first end;
 a second end opposite from the first end and comprising an end wall;
 a chamber between the first end and the second end, wherein the end wall at least partially defines the chamber;
 a plurality of tabs on the end wall and extending away from the end wall outside of the chamber; and
 a plurality of projections on the end wall and extending away from the end wall outside of the chamber,
  wherein a height of the plurality of tabs is less than a height of the plurality of projections.

9. The metering dispenser of claim 8, further comprising a base rotationally coupled to the second end of the body, wherein the plurality of projections are configured to produce a first audible sound based on engagement between the plurality of projections and the base when the base is rotated, and wherein the plurality of tabs are configured to produce a second audible sound based on engagement between the plurality of tabs and the base when the base is rotated.

10. The metering dispenser of claim 8, further comprising a drive screw, the drive screw comprising a first end, a second end, and an elongated shaft, wherein the elongated shaft comprises the second end of the drive screw, wherein the elongated shaft comprises an outer surface comprising a first portion having at least one external thread and a second portion between the first portion and the second end, and wherein the second portion is unthreaded.

11. The metering dispenser of claim 10, further comprising a plunger positioned within the chamber and coupled to the elongated shaft of the drive screw such that the plunger is movable along the elongated shaft through the chamber when the drive screw is rotated.

12. The metering dispenser of claim 8, wherein the end wall of the second end defines an aperture, and wherein the plurality of tabs and the plurality of projections are arranged around the aperture.

13. The metering dispenser of claim 8, wherein each tab of the plurality of tabs is positioned between two projections of the plurality of projections, and wherein each tab is positioned unequally between the two projections such that a distance between the tab and a first of the two projections is less than a distance between the tab and a second of the two projections.

14. A metering dispenser comprising:
 a body comprising a first end and a second end opposite from the first end, wherein the body defines a chamber between the first end and the second end; and
 a drive screw comprising a first end, a second end, and an elongated shaft, wherein the elongated shaft comprises the second end of the drive screw, and wherein the elongated shaft comprises an outer surface comprising:
  a first portion having at least one external thread; and
  a second portion between the first portion and the second end, wherein the second portion is unthreaded,
 wherein the first end of the body defines a chamber opening providing access to the chamber, wherein the second end of the body comprises an end wall that at least partially defines the chamber of the body, and wherein the body comprises a plurality of tabs and a plurality of projections on the end wall and extending away from the end wall outside the chamber.

15. The metering dispenser of claim 14, wherein the drive screw further comprises a cog, and wherein the cog comprises the first end of the drive screw.

16. The metering dispenser of claim 14, further comprising a plunger positioned within the chamber and coupled to the elongated shaft of the drive screw such that the plunger is movable along the elongated shaft through the chamber when the drive screw is rotated.

17. The metering dispenser of claim 14, wherein a height of the plurality of tabs is less than a height of the plurality of projections.

18. The metering dispenser of claim 14, further comprising a base rotationally coupled to the second end of the body, wherein the plurality of projections are configured to produce a first audible sound based on engagement between the plurality of projections and the base when the base is rotated, and wherein the plurality of tabs are configured to produce a second audible sound based on engagement between the plurality of tabs and the base when the base is rotated.

19. The metering dispenser of claim 14, wherein the end wall of the second end defines an aperture, wherein the plurality of tabs and the plurality of projections are arranged around the aperture, and wherein the drive screw extends through the aperture.

\* \* \* \* \*